United States Patent
Cha et al.

(10) Patent No.: US 12,010,915 B2
(45) Date of Patent: Jun. 11, 2024

(54) ORGANIC LIGHT-EMITTING DIODE HAVING LONG LIFESPAN, LOW VOLTAGE, AND HIGH EFFICIENCY PROPERTY

(71) Applicant: SFC CO., LTD., Cheongju-si (KR)

(72) Inventors: Soon-Wook Cha, Goyang-si (KR); Sang-Woo Park, Seoul (KR); Jung-Ho Yoo, Seosan-si (KR); Ji-Hwan Kim, Anyang-si (KR); Sung Woo Kim, Seoul (KR); Hyeon Jun Jo, Busan (KR); Young-Hwan Park, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 743 days.

(21) Appl. No.: 16/338,717

(22) PCT Filed: Sep. 14, 2017

(86) PCT No.: PCT/KR2017/010090
§ 371 (c)(1),
(2) Date: Apr. 2, 2019

(87) PCT Pub. No.: WO2018/066831
PCT Pub. Date: Apr. 12, 2018

(65) Prior Publication Data
US 2021/0288266 A1    Sep. 16, 2021

(30) Foreign Application Priority Data
Oct. 5, 2016  (KR) .......... 10-2016-0128240

(51) Int. Cl.
| | | |
|---|---|---|
| H01L 51/00 | (2006.01) |
| C07C 211/61 | (2006.01) |
| C07D 307/91 | (2006.01) |
| C09K 11/06 | (2006.01) |
| H10K 85/60 | (2023.01) |
| H10K 50/11 | (2023.01) |

(52) U.S. Cl.
CPC ........ *H10K 85/6574* (2023.02); *C07C 211/61* (2013.01); *C07D 307/91* (2013.01); *C09K 11/06* (2013.01); *H10K 85/615* (2023.02); *H10K 85/626* (2023.02); *H10K 85/633* (2023.02); *C07B 2200/05* (2013.01); *C07C 2603/40* (2017.05); *C07C 2603/52* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 85/622* (2023.02); *H10K 85/623* (2023.02)

(58) Field of Classification Search
CPC ... C07D 307/91; C07C 211/61; C07C 211/57; C07C 211/58; H10K 85/633; H10K 85/653
See application file for complete search history.

(56) References Cited

U.S. PATENT DOCUMENTS

| | | | | |
|---|---|---|---|---|
| 10,468,603 | B2 * | 11/2019 | Cha .................. | H10K 85/633 |
| 10,562,876 | B2 * | 2/2020 | Cha .................. | H01L 51/0073 |
| 10,950,802 | B2 * | 3/2021 | Park .................. | H10K 50/171 |
| 2016/0028015 | A1 | 1/2016 | Kim et al. | |
| 2017/0346009 | A1 * | 11/2017 | Yokoyama ........... | H10K 85/615 |

FOREIGN PATENT DOCUMENTS

| | | | |
|---|---|---|---|
| EP | 3098873 A1 | 11/2016 | |
| EP | 3269790 A1 | 1/2018 | |
| JP | 2011037838 * | 2/2011 | ............ C07F 7/10 |
| JP | 2015065324 A | 4/2015 | |
| JP | WO2016117848 * | 7/2016 | .......... C07B 59/002 |
| KR | 1020080015865 A | 2/2008 | |
| KR | 1020120047706 A | 5/2012 | |
| KR | 2012135501 A * | 12/2012 | ............ C07C 15/28 |
| KR | 20120135501 A | 12/2012 | |
| KR | 1020120135501 A | 12/2012 | |
| KR | 1020150043020 A | 4/2015 | |
| KR | 1020160043505 A | 4/2016 | |
| KR | 1020160090443 A | 8/2016 | |
| KR | 1020160095827 A | 8/2016 | |
| KR | 20160141359 A | 12/2016 | |
| KR | 20160141361 A | 12/2016 | |
| KR | 101900726 B1 | 9/2018 | |

OTHER PUBLICATIONS

JP2011037838 machine translation from Google patents downloaded Jan. 29, 2022.*
The extended European Search Report of EP 17 85 8626, Mar. 17, 2020.
International search report of PCT/KR2017/010090, Dec. 12, 2017, English translation.

* cited by examiner

*Primary Examiner* — Alexander R Pagano
(74) *Attorney, Agent, or Firm* — STIP Law Group, LLC

(57) ABSTRACT

The present disclosure relates to an organic light-emitting diode and, more particularly, to an organic-light-emitting diode comprising: a first electrode; a second electrode facing the first electrode; and a light-emitting layer intercalated between the first electrode and the second electrode, wherein the light-emitting layer comprises at least one of the amine compounds represented by the following Chemical Formula A and at least one of the anthracene compounds represented by the following Chemical Formula B or C. The structures of Chemical Formulas A to C are the same as in the specification.

9 Claims, 1 Drawing Sheet

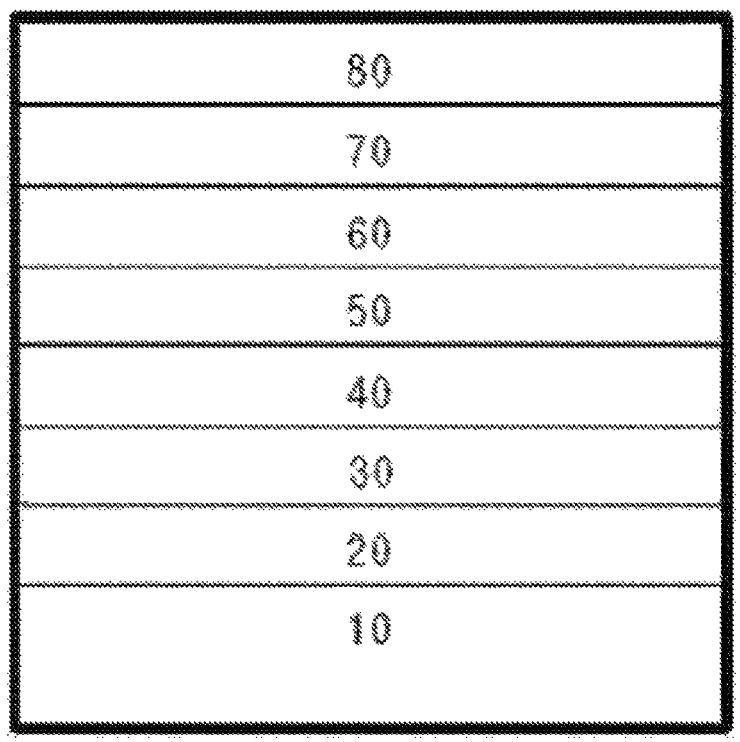

ORGANIC LIGHT-EMITTING DIODE HAVING LONG LIFESPAN, LOW VOLTAGE, AND HIGH EFFICIENCY PROPERTY

CROSS-REFERENCE TO RELATED APPLICATIONS

This application is the U.S. National Phase under 35 U.S.C. § 371 of International Application No. PCT/KR2017/010090 filed on Sep. 14, 2017, which in turn claims the benefit of Korean Application No. 10-2016-0128240, filed on Oct. 5, 2016, the disclosures of which are incorporated by reference into the present application.

TECHNICAL FIELD

The present disclosure relates to an organic light-emitting diode with long lifespan, low driving voltage, and high efficiency and, more particularly, to an organic light-emitting diode wherein host and dopant materials of specific structures are used in a light-emitting layer to ensure long lifespan, low voltage, and high efficiency.

BACKGROUND ART

Organic light-emitting diodes (OLEDs), based on self-luminescence, are used to create digital displays with the advantage of having a wide viewing angle and being able to be made thinner and lighter than liquid crystal displays. In addition, an OLED display exhibits a very fast response time. Accordingly, OLEDs find applications in the full color display field or the illumination field.

Materials used as the organic layers in organic light emitting diodes may be divided into luminescent materials and charge charrier materials on the basis of functions, for example, a hole injection material, a hole transport material, an electron injection material, and an electron transport material.

In addition, the light emitting mechanisms allow the luminescent materials to be classified as fluorescent and phosphorescent materials, which use excitons in singlet and triplet states, respectively.

Meanwhile, when a single material is employed as the luminescent material, intermolecular actions cause the maximum luminescence wavelength to shift toward a longer wavelength, resulting in a reduction in color purity and light emitting efficiency. In this regard, a host-dopant system may be used as a luminescent material so as to increase the color purity and the light emitting efficiency through energy transfer.

This is based on the principle that, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kind of the dopant because the wavelength of the host shifts toward a wavelength range of the dopant.

With regard to related arts of dopant compounds in the light-emitting layer, reference may be made to Korean Patent No. 10-2008-0015865 A (Feb. 20, 2008), which describes an organic light emitting device using an arylamine-coupled indenofluorene derivative, and Korean patent No. 10-2012-0047706 A (May 14, 2012), which describes an organic light emitting device using a compound having dibenzofuran or dibenzothiophene that coexists with fluorescence or carbazole within a single molecule.

As a related art for using a host compound in a light-emitting layer, mention may be made of Korean Patent No. 10-2015-0043020 A (Apr. 22, 2015), which discloses an organic light-emitting diode employing an anthracene derivative as a fluorescent host Despite such related arts, however, there is still a continued need to develop organic light-emitting diodes exhibiting a longer lifespan, a lower voltage, and higher efficiency.

DETAILED DESCRIPTION OF THE INVENTION

Technical Problem

Therefore, the purpose of the present disclosure is to provide a novel organic light-emitting diode with a long lifespan, a low driving voltage, and high efficiency, wherein dopant and host materials of specific structures are employed.

Technical Solution

The present disclosure provides an organic light-emitting diode, comprising: a first electrode; a second electrode facing the first electrode; and a light-emitting layer intercalated between the first electrode and the second electrode, wherein the light-emitting layer comprises at least one of the amine compounds represented by the following Chemical Formula A and at least one of the anthracene compounds represented by the following Chemical Formula B or C:

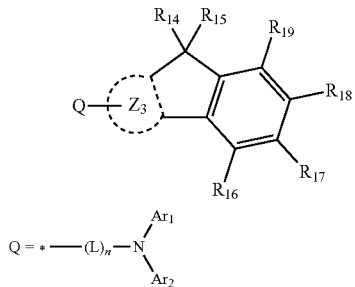

[Chemical Formula A]

wherein, $Z_3$ is any one selected from among a substituted or unsubstituted aromatic hydrocarbon ring of 6 to 30 carbon atoms and a substituted or unsubstituted aromatic heteroring of 2 to 20 carbon atoms bearing O, N, or S as a heteroatom, the substituents $R_{14}$ to $R_{19}$, which are the same or different, are each independently one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted heteroaryl of 2 to 50 carbon atoms bearing as a heteroatom at least one selected from O, N, and S, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a cyano, a nitro, a hydroxyl, and a halogen, with a proviso that one of the substituents $R_{16}$ to $R_{19}$ represents a single bond attached to the linker L in a Q moiety, the substituents $R_{14}$ and $R_{15}$ may be connected to each other to form a ring, adjacent substituents of $R_{16}$ to $R_{19}$ may be connected to each other to form a mono- or a polycyclic aliphatic or aromatic ring which may be a heterocyclic ring bearing a heteroatom selecting from among N, S, and O as a ring member, two adjacent carbon atoms within $Z_3$ form a five-membered ring with the carbon atom having both the substituents $R_{14}$ and $R_{15}$ thereon, thus establishing a fused ring, a carbon atom of the aromatic ring of $Z_3$ which does not participate in forming the five-membered ring is bonded to the linker L in a Q moiety, the linker L represents a single bond or is one selected from among a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

n is an integer of 0 to 2 wherein when n is 2, the linkers L are the same or different, the respective moieties Q's which are bonded to $Z_3$ and to one of $R_{16}$ to $R_{19}$ are the same or different, the substituents $Ar_1$ and $Ar_2$, which are the same or different, are each independently one selected from among a substituted or unsubstituted aryl of 6 to 40 carbon atoms, a substituted or unsubstituted heteroaryl of 2 to 30 carbon atoms, a substituted or unsubstituted alkyl of 1 to 40 carbon atoms, and a substituted or unsubstituted cycloalkyl of 3 to 30 carbon atoms;

[Chemical Formula B]

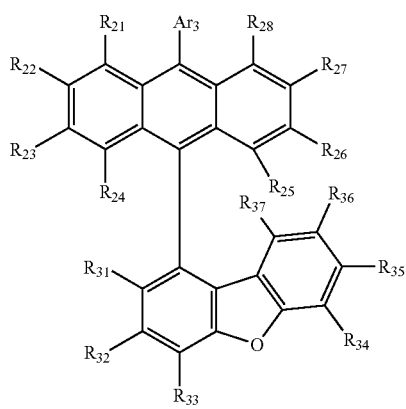

-continued

[Chemical Formula C]

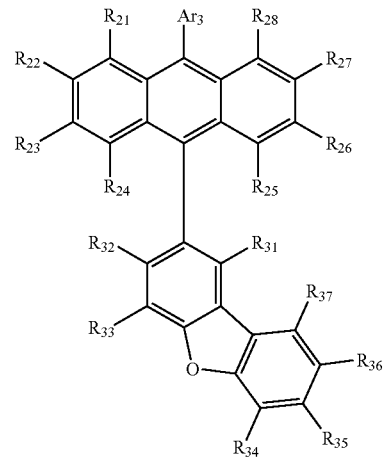

wherein, $R_{21}$ to $R_{28}$ and $R_{31}$ to $R_{37}$, which are the same or different, are each independently one selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, a substituted or unsubstituted silyl of 1 to 30 carbon atoms, a substituted or unsubstituted germanium of 1 to 30 carbon atoms, a substituted or unsubstituted boron of 1 to 30 carbon atoms, a substituted or unsubstituted aluminum of 1 to 30 carbon atoms, a carbonyl, a phosphoryl, an amino, a thiol, a hydroxy, a selenium, a tellurium, an amide, an ether, and an ester, and the substituent $Ar_3$ is one selected from among a substituted or unsubstituted aryl of 6 to 50 carbon atoms and a substituted or unsubstituted heteroaryl of 2 to 50 carbon atoms.

Advantageous Effect

The organic light-emitting diode according to the present disclosure has longer lifespan, lower driving voltage and improved efficiency, compared to conventional organic light-emitting diodes.

BRIEF DESCRIPTION OF THE DRAWINGS

FIG. 1s a schematic view of an organic light-emitting diode according to an embodiment of the present disclosure.

BEST MODE FOR INVENTION

Below, a detailed description will be given of the present disclosure.

In order to accomplish the purpose, the present disclosure addresses an organic light-emitting diode, comprising: a first electrode; a second electrode facing the first electrode; and a light-emitting layer intercalated between the first electrode and the second electrode, wherein the light-emitting layer comprises at least one of the amine compounds represented by the following Chemical Formula A and at least one of the anthracene compounds represented by the following Chemical Formula B or C:

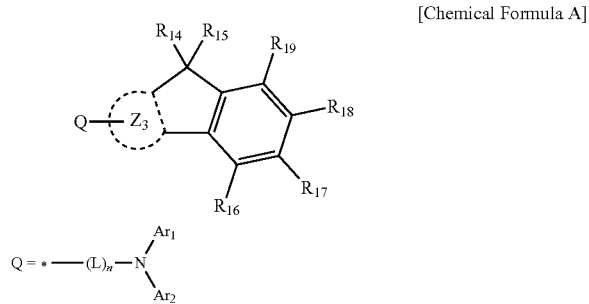

[Chemical Formula A]

wherein, $Z_3$ is any one selected from among a substituted or unsubstituted aromatic hydrocarbon ring of 6 to 30 carbon atoms and a substituted or unsubstituted aromatic heteroring of 2 to 20 carbon atoms bearing O, N, or S as a heteroatom, the substituents $R_{14}$ to $R_{19}$, which are the same or different, are each independently one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted heteroaryl of 2 to 50 carbon atoms bearing as a heteroatom at least one selected from O, N, and S, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a cyano, a nitro, a hydroxyl, and a halogen, with a proviso that one of the substituents $R_{16}$ to $R_{19}$ represents a single bond attached to the linker L in a Q moiety, the substituents $R_{14}$ and $R_{15}$ may be connected to each other to form a ring, adjacent substituents of $R_{16}$ to $R_{19}$ may be connected to each other to form a mono- or a polycyclic aliphatic or aromatic ring which may be a heterocyclic ring bearing a heteroatom selecting from among N, S, and O as a ring member, two adjacent carbon atoms within $Z_3$ form a five-membered ring with the carbon atom having both the substituents $R_{14}$ and $R_{15}$ thereon, thus establishing a fused ring, a carbon atom of the aromatic ring of $Z_3$ which does not participate in forming the five-membered ring is bonded to the linker L in a Q moiety, the linker L represents a single bond or is one selected from among a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

n is an integer of 0 to 2 wherein when n is 2, the linkers L are the same or different, the respective moieties Q's which are bonded to $Z_3$ and to one of $R_{16}$ to $R_{19}$ are the same or different, the substituents $Ar_1$ and $Ar_2$, which are the same or different, are each independently one selected from among a substituted or unsubstituted aryl of 6 to 40 carbon atoms, a substituted or unsubstituted heteroaryl of 2 to 30 carbon atoms, a substituted or unsubstituted alkyl of 1 to 40 carbon atoms, and a substituted or unsubstituted cycloalkyl of 3 to 30 carbon atoms;

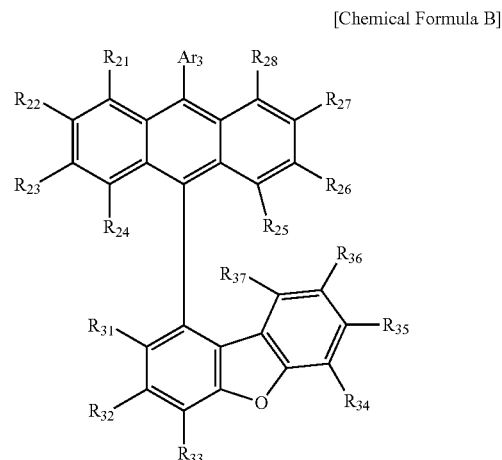

[Chemical Formula B]

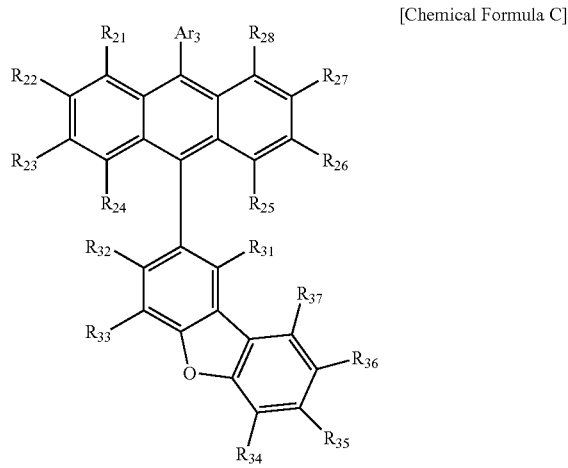

[Chemical Formula C]

wherein, $R_{21}$ to $R_{28}$ and $R_{31}$ to $R_{37}$, which are the same or different, are each independently one selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, a substituted or unsubstituted silyl of 1 to 30 carbon atoms, a substituted or unsubstituted germanium of 1 to 30 carbon atoms, a substituted or unsubstituted boron of 1 to 30 carbon atoms, a substituted or unsubstituted aluminum of 1 to 30 carbon atoms, a carbonyl, a phosphoryl, an amino, a thiol, a hydroxy, a selenium, a tellurium, an amide, an ether, and an ester, and the substituent $Ar_3$ is one selected from among a substituted or unsubstituted aryl of 6 to 50 carbon atoms and a substituted or unsubstituted heteroaryl of 2 to 50 carbon atoms.

wherein the term 'substituted' in the expression 'substituted or unsubstituted' means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 1 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms, such as "a substituted or unsubstituted alkyl of 1 to 30 carbon atoms", "a substituted or unsubstituted aryl of 6 to 50 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" as a substituent used in the compounds of the present disclosure means an organic radical derived from an aromatic hydrocarbon by removing one hydrogen atom and encompasses a 5- to 7-membered and preferably a 5- or 6-membered monocyclic ring or fused ring system. In addition, the aromatic system may further include a fused ring that is formed by adjacent substituents, if present, on the aryl radical.

Concrete examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, but are not limited thereto.

At least one hydrogen atom on the aryl radical may be substituted by a deuterium atom, a halogen atom, a hydroxy, a nitro, a cyano, a silyl, an amino ($—NH_2$, $—NH(R)$, $—N(R')(R'')$ wherein R' and R'' are each independently an alkyl of 1 to 10 carbon atoms, in this case called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms.

The substituent heteroaryl used in the compound of the present disclosure refers to a cyclic aromatic system of 2 to 24 carbon atoms bearing one to three heteroatoms selected from among N, O, P, Si, S, Ge, Se, and Te. In the aromatic system, two or more rings may be fused. One or more hydrogen atoms on the heteroaryl may be substituted by the same substituents as on the aryl.

As used herein, the term "heteroaromatic ring" refers to an aromatic hydrocarbon ring bearing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy used in the compounds of the present disclosure include methoxy, ethoxy, propoxy, isobutyloxy, sec-butyloxy, iso-amyloxy, hexyloxy. At least one hydrogen atom of the alkoxy may be substituted by the same substituent as in the aryl.

Representative among the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms in the silyl may be substituted by the same substituent as in the aryl.

The light-emitting layer in the organic light-emitting diode according to the present disclosure comprises a host and a dopant wherein the anthracene compound represented by Chemical Formula B or Chemical Formula C may be used as the host and the amine compound represented by Chemical Formula A may be used as the dopant. That is, the organic light-emitting diode that employs the fluorenyl-containing diamine compound represented by Chemical Formula A as a dopant and the dibenzofuran-substituted anthracene compound represented by Chemical Formula B or C as a host in a light-emitting layer has the effect of exhibiting a longer lifespan, a lower driving voltage, and more improved efficiency, compared to conventional organic light-emitting diodes.

In Chemical Formula A, $Z_3$ may be a substituted or unsubstituted aromatic hydrocarbon ring of 6 to 30 carbon atoms. In this regard, the substituted or unsubstituted aromatic hydrocarbon ring of 6 to 30 carbon atoms may be one selected from among the following Structural Formula 10 to Structural Formula 21:

[Structural Formula 10]

[Structural Formula 11]

[Structural Formula 12]

[Structural Formula 13]

[Structural Formula 14]

[Structural Formula 15]

[Structural Formula 16]

[Structural Formula 17]

[Structural Formula 18]

[Structural Formula 19]

[Structural Formula 20]

[Structural Formula 21]

wherein

"-*" denotes a bonding site for forming a 5-membered ring containing the carbon atom connected to both $R_{14}$ and $R_{15}$, R's are as defined above for $R_{14}$ to $R_{19}$, and m is an integer of 1 to 8 wherein when m is 2 or more or when R is two or more, individual R's may be the same or different.

According to an embodiment of the present disclosure, the linker L in Chemical Formula A may be a single bond or one selected from among the following Structural Formulas 1 to 9:

[Structural Formula 1]

[Structural Formula 2]

[Structural Formula 3]

[Structural Formula 4]

[Structural Formula 5]

-continued

[Structural Formula 6]

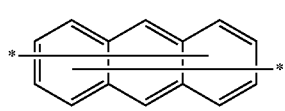

[Structural Formula 7]

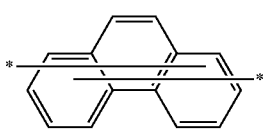

[Structural Formula 8]

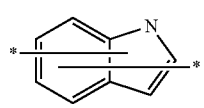

[Structural Formula 9]

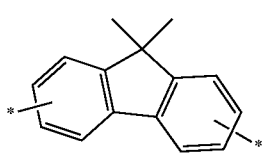

In Structural Formulas 1 to 9, each of the unsubstituted carbon atoms of the aromatic ring moiety is bound with a hydrogen atom or a deuterium atom.

According to an embodiment of the present disclosure, $R_{14}$ and $R_{15}$ in Chemical Formula A, which are the same or different, may each be independently a substituted or unsubstituted aryl of 6 to 30 carbon atoms and may be connected to each other to form a ring.

According to an embodiment of the present disclosure, $Ar_1$ and $Ar_2$, which are the same or different, may each be independently a substituted or unsubstituted aryl of 6 to 30 carbon atoms.

According to an embodiment of the present disclosure, examples of the amine compound represented by Chemical Formula A include the compounds represented by the following Chemical Formulas 1 to 60, but are not limited thereto:

<Chemical Formula 1>

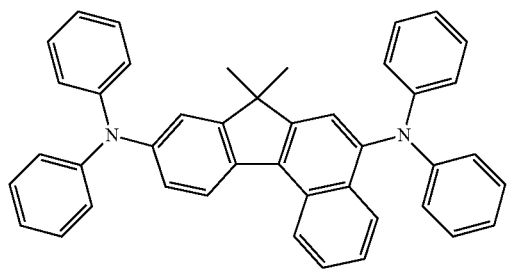

<Chemical Formula 2>

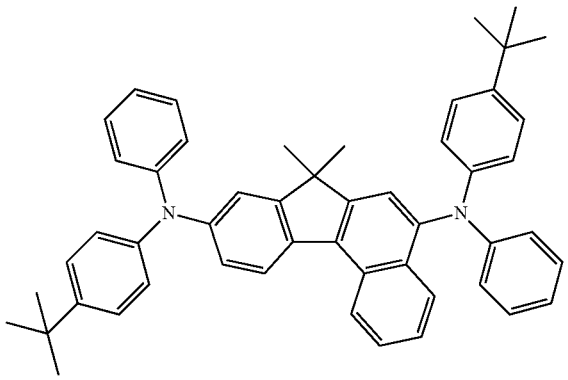

<Chemical Formula 3>

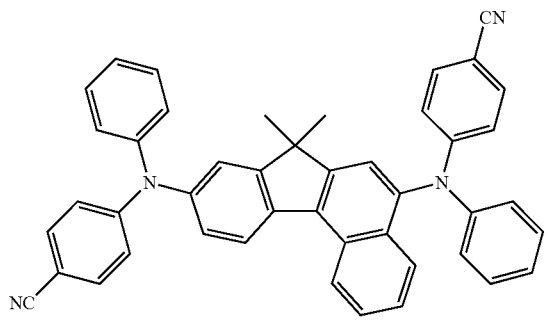

<Chemical Formula 4>

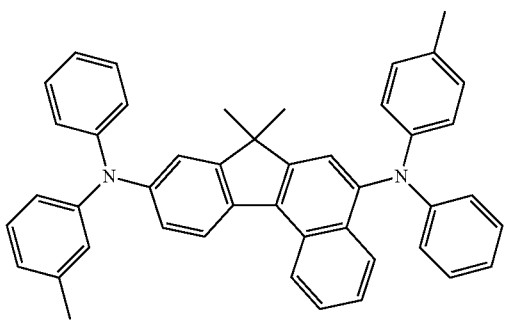

-continued
<Chemical Formula 5>
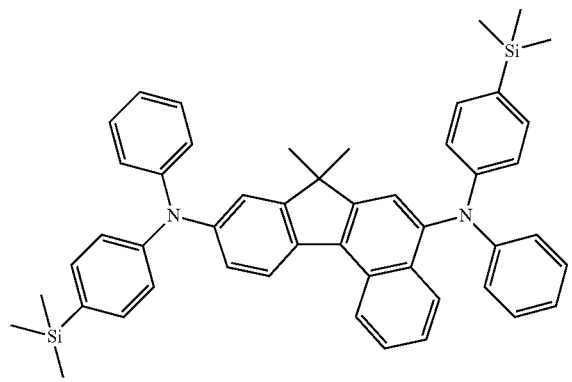
<Chemical Formula 6>
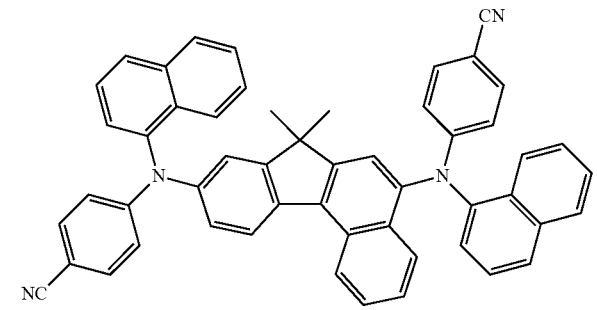
<Chemical Formula 7>
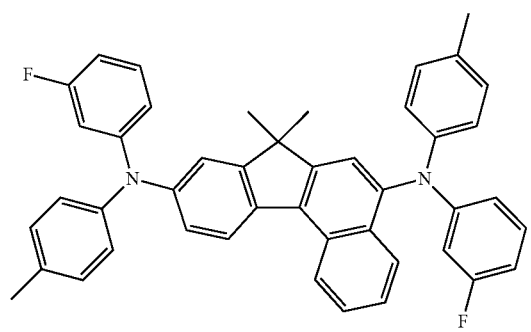
<Chemical Formula 8>
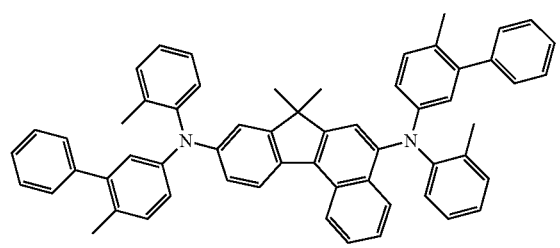
<Chemical Formula 9>
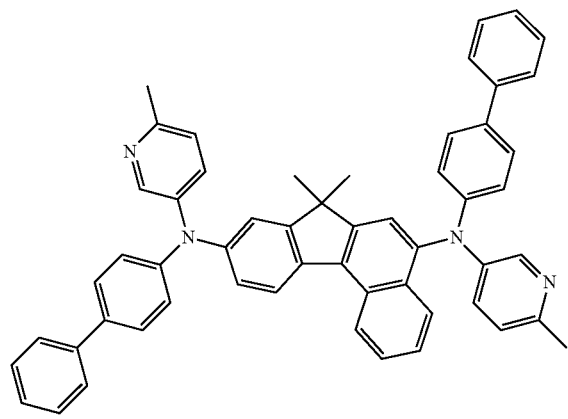
<Chemical Formula 10>
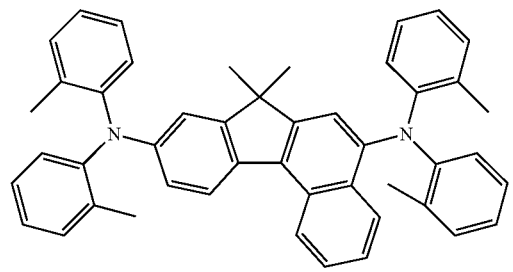
<Chemical Formula 11>
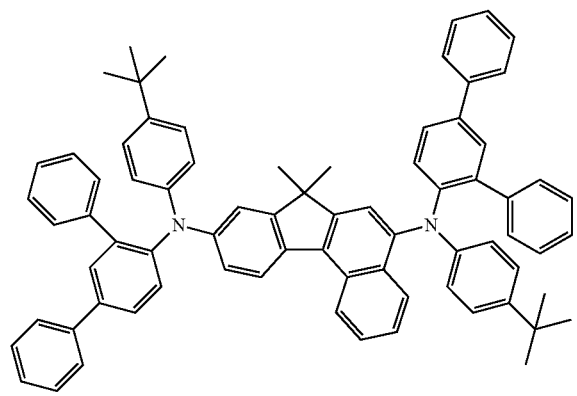
<Chemical Formula 12>
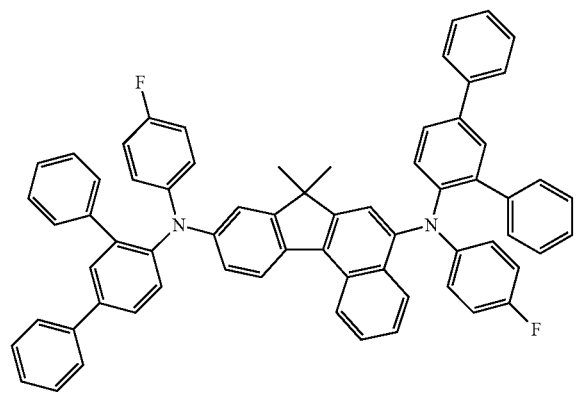

<Chemical Formula 13>
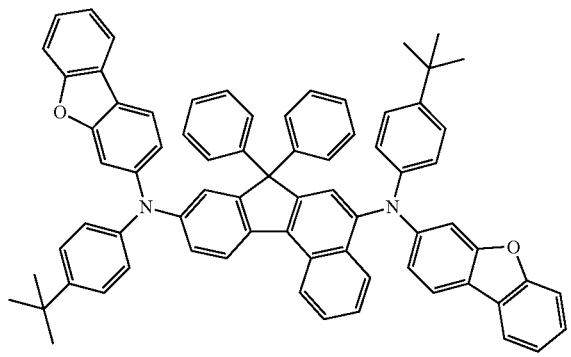
<Chemical Formula 14>
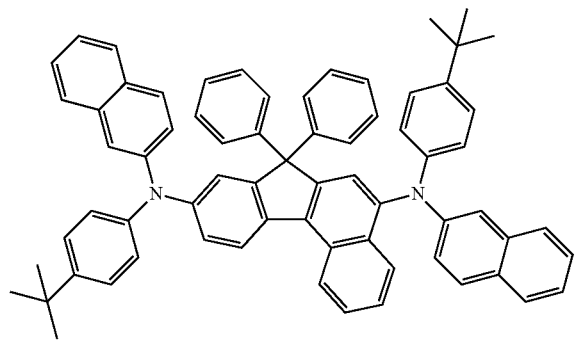
<Chemical Formula 15>
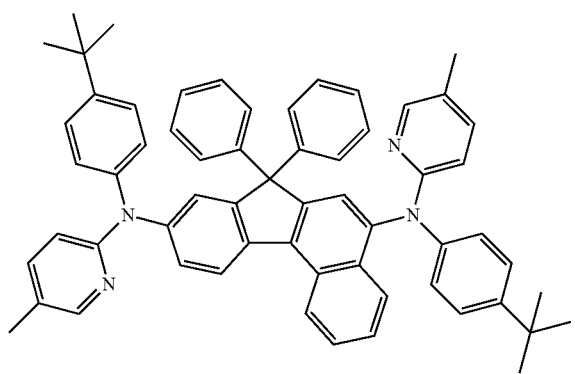
<Chemical Formula 16>
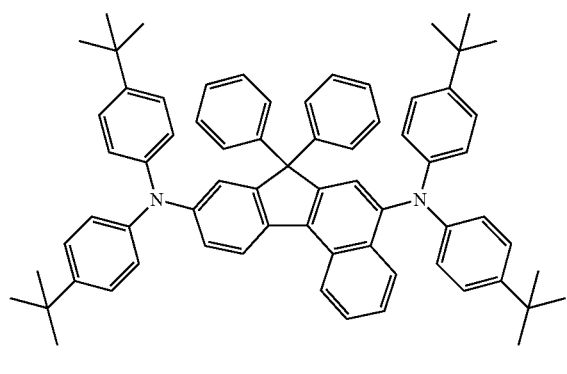
<Chemical Formula 17>
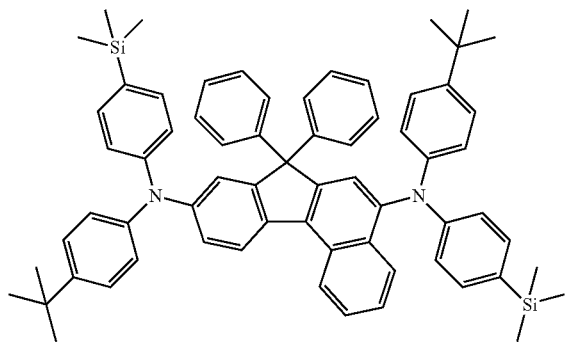
<Chemical Formula 18>
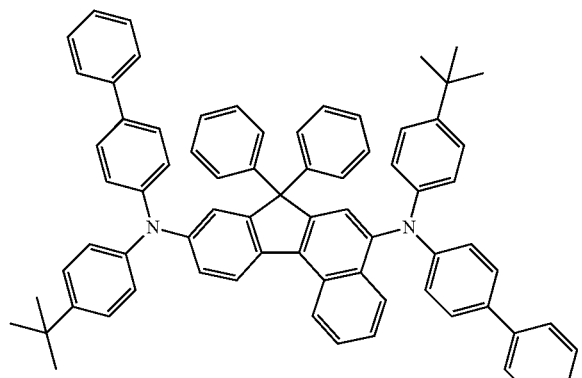
<Chemical Formula 19>
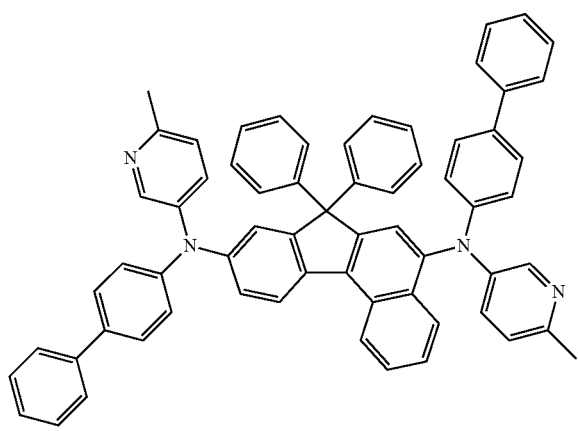

<Chemical Formula 20>
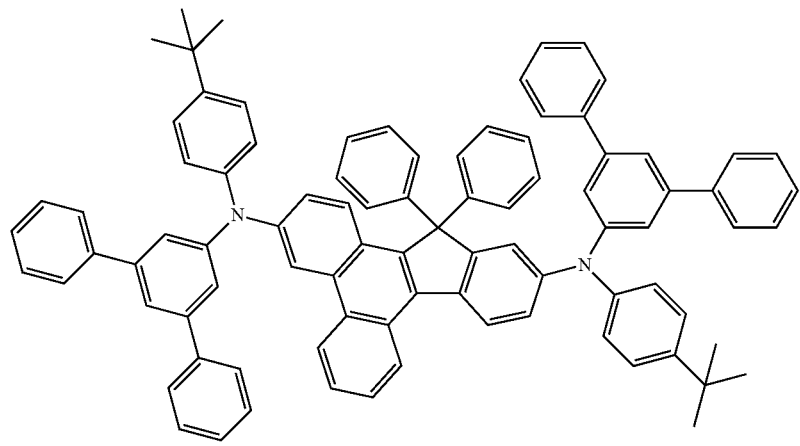
<Chemical Formula 21>
<Chemical Formula 22>
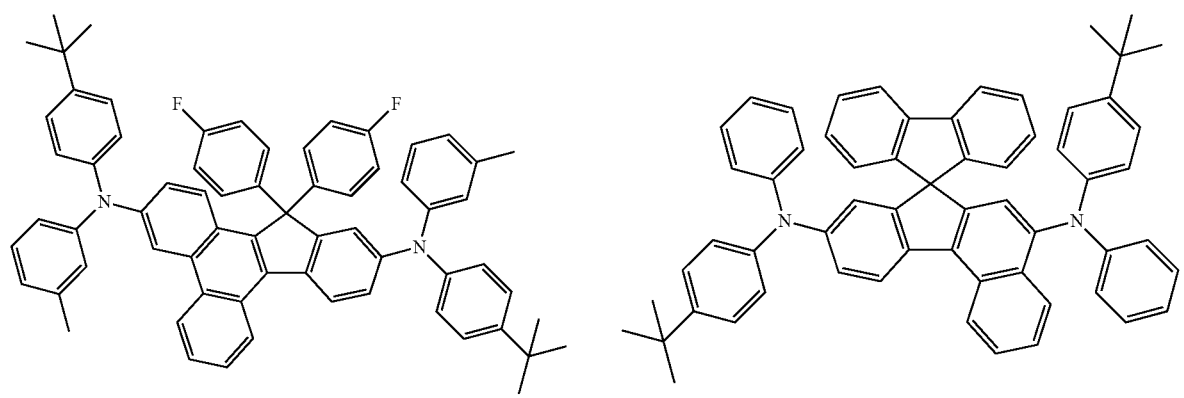
<Chemical Formula 23>
<Chemical Formula 24>
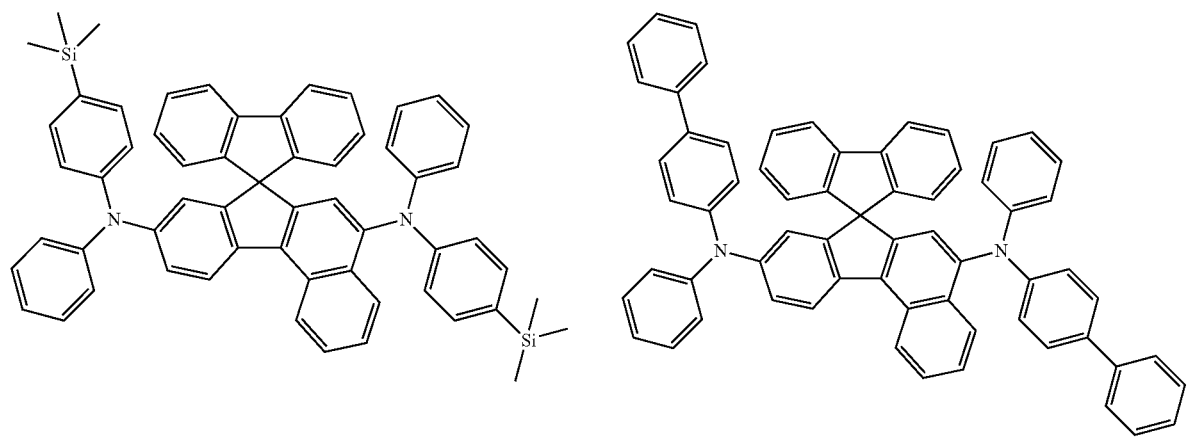

-continued
<Chemical Formula 25>
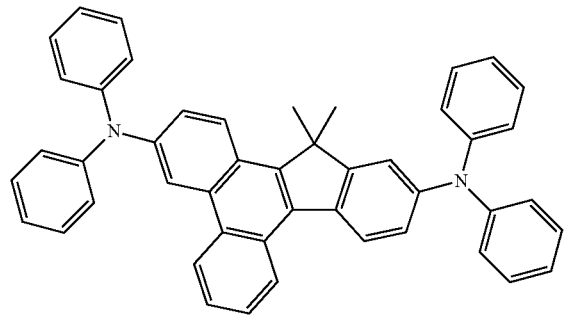
<Chemical Formula 26>
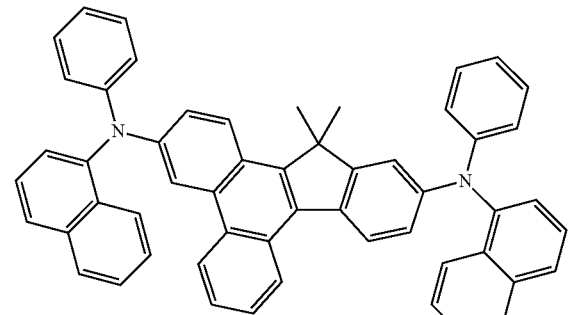
<Chemical Formula 27>
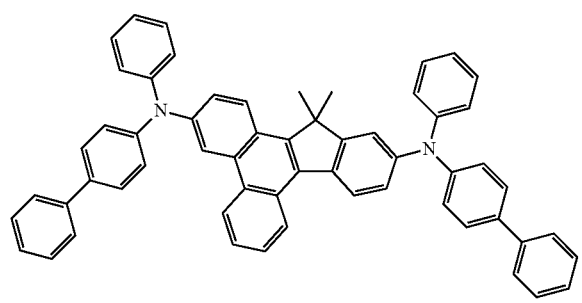
<Chemical Formula 28>
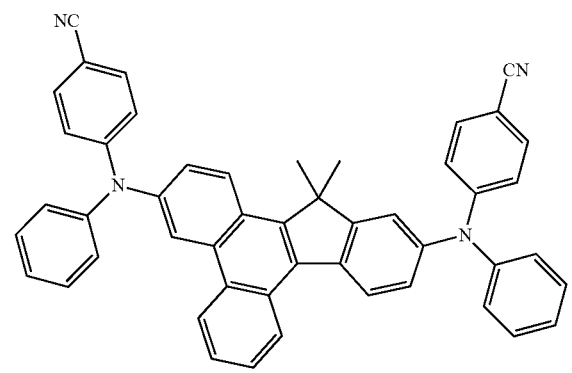
<Chemical Formula 29>
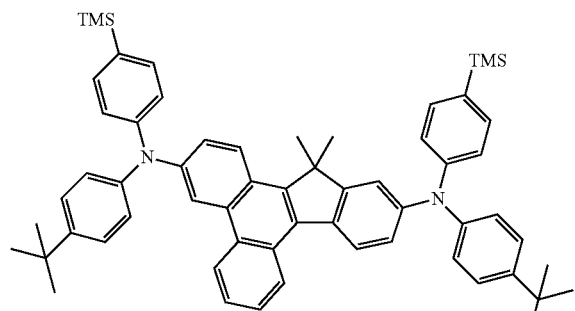
<Chemical Formula 30>
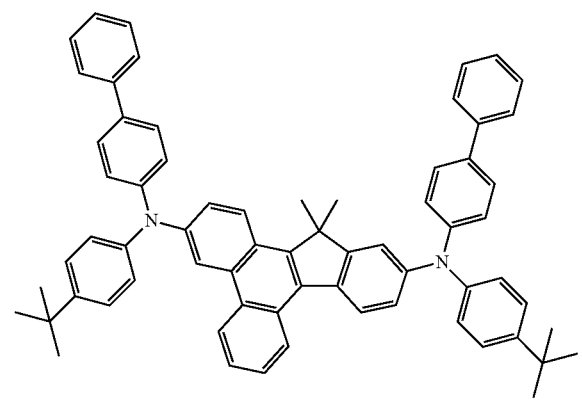
<Chemical Formula 31>
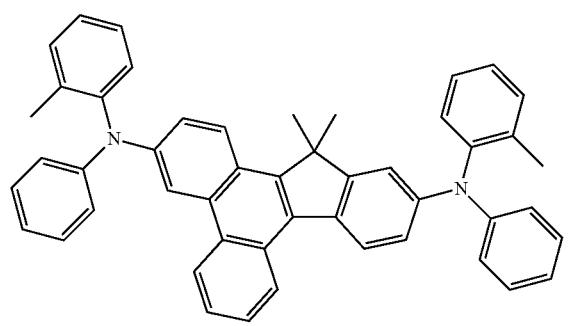
<Chemical Formula 32>
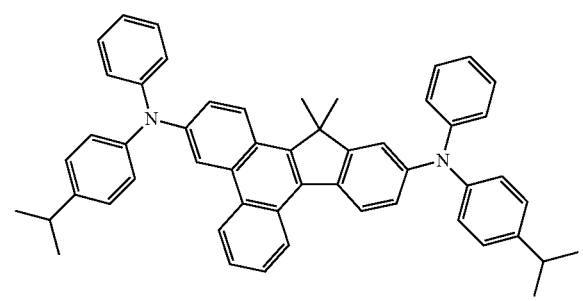

-continued
<Chemical Formula 33>
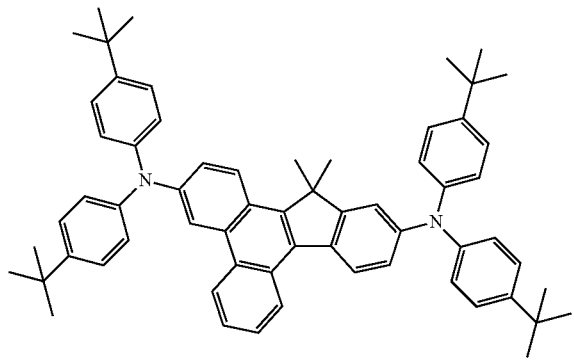
<Chemical Formula 34>
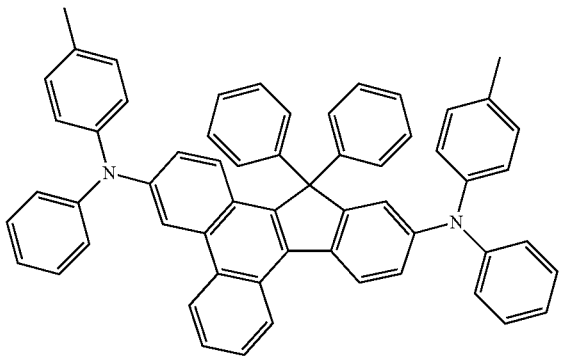
<Chemical Formula 35>
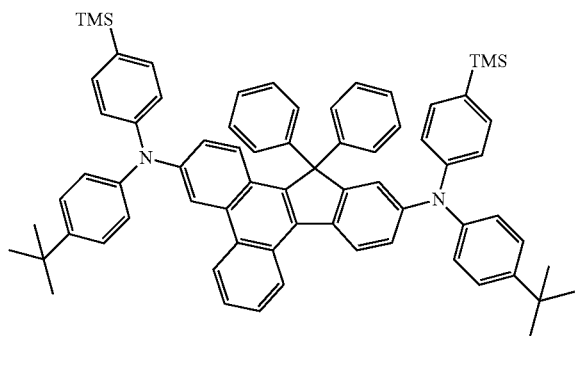
<Chemical Formula 36>
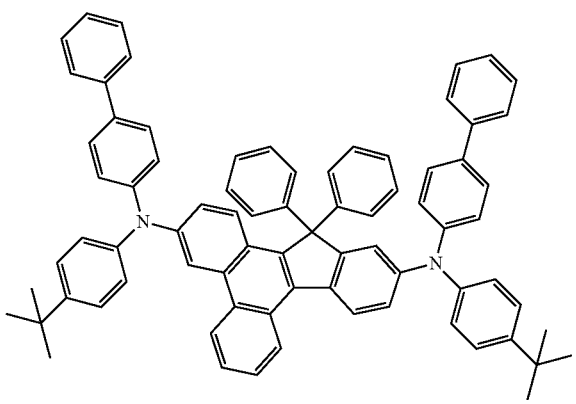
<Chemical Formula 37>
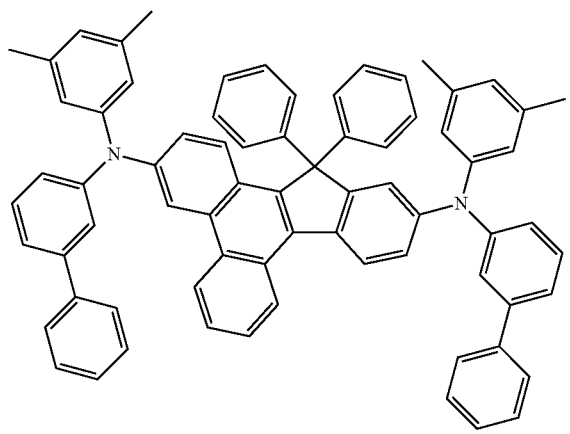
<Chemical Formula 38>
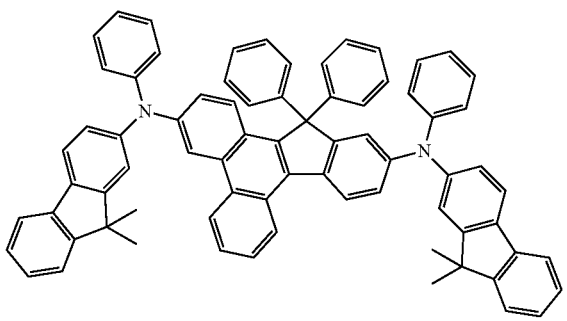

<Chemical Formula 39>
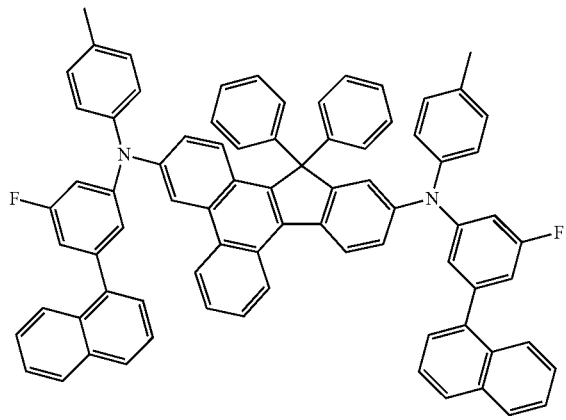
<Chemical Formula 40>
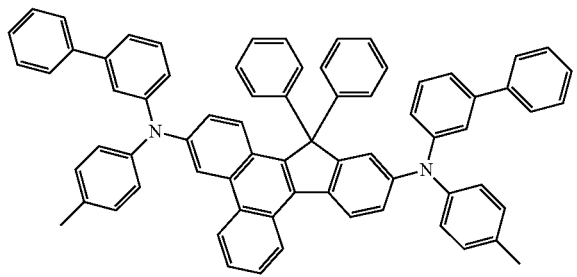
<Chemical Formula 41>
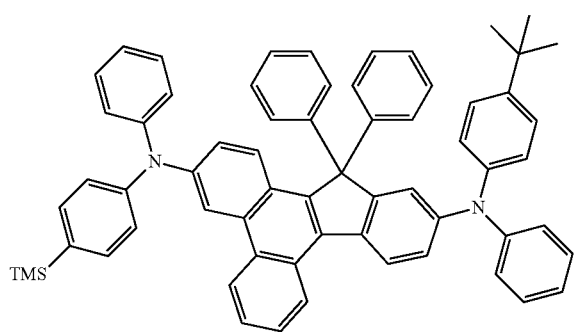
<Chemical Formula 42>
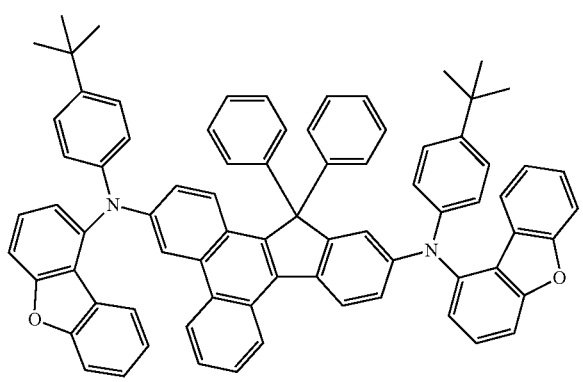
<Chemical Formula 43>
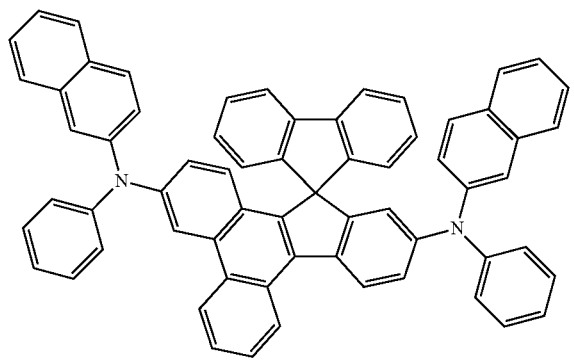
<Chemical Formula 44>
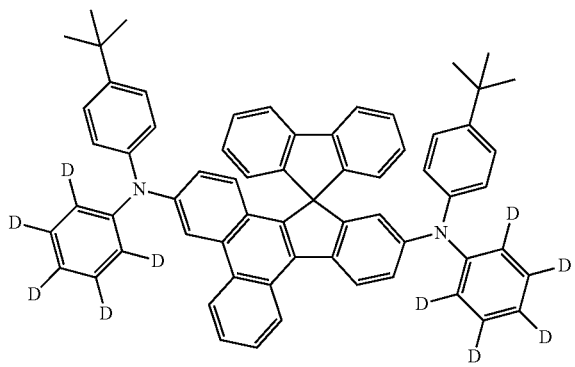
<Chemical Formula 45>
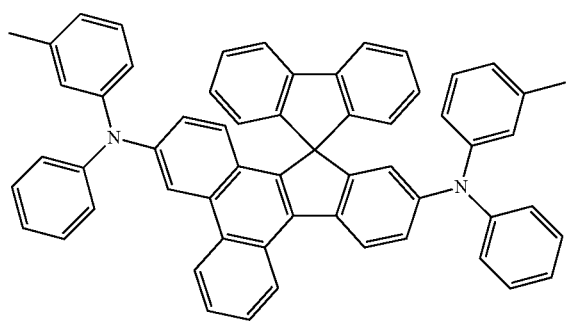
<Chemical Formula 46>
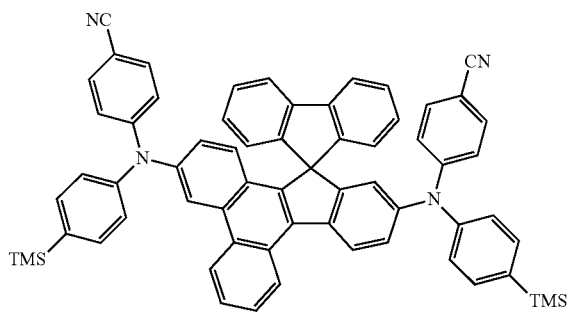

-continued
<Chemical Formula 47>
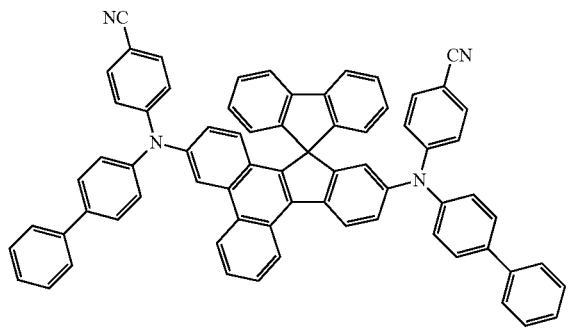
<Chemical Formula 48>
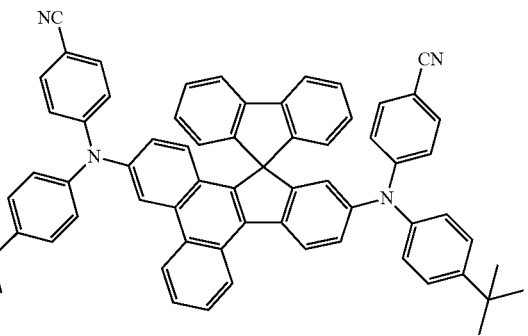
<Chemical Formula 49>
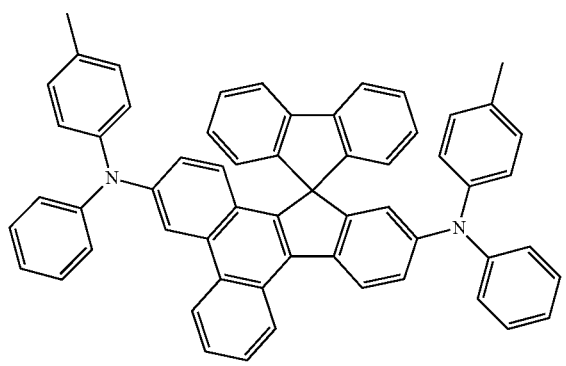
<Chemical Formula 50>
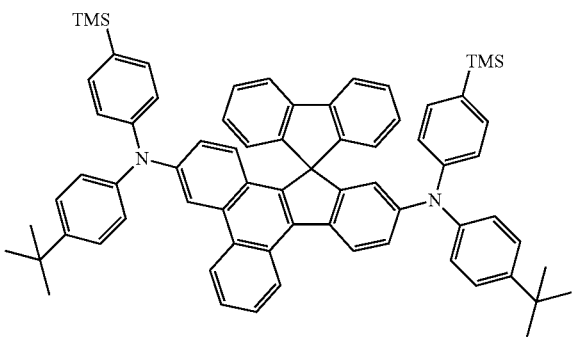
<Chemical Formula 51>
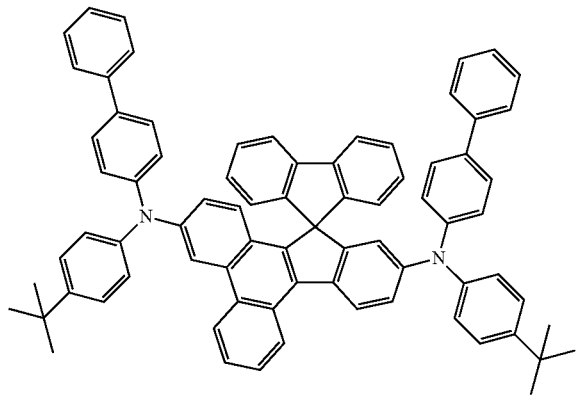
<Chemical Formula 52>
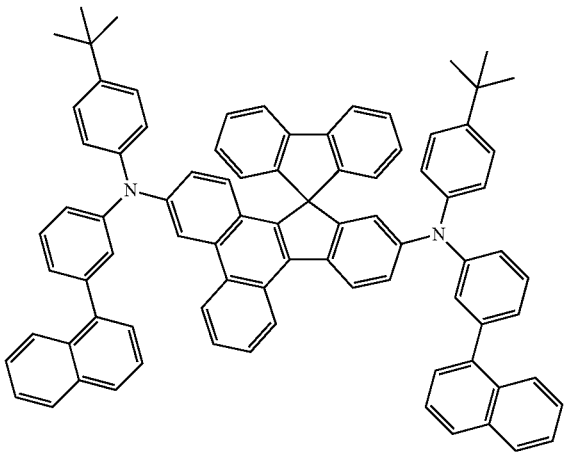
<Chemical Formula 53>
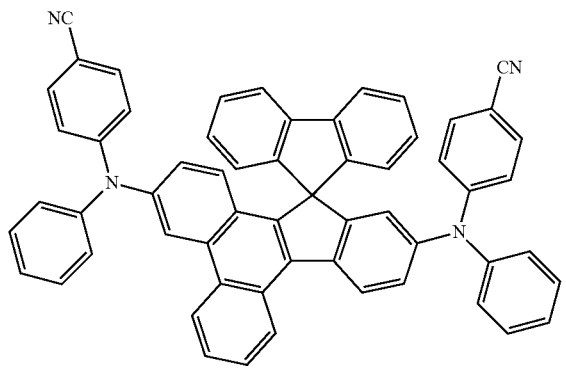
<Chemical Formula 54>
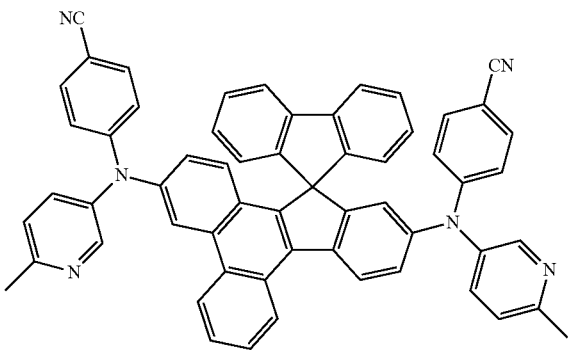

<Chemical Formula 55>
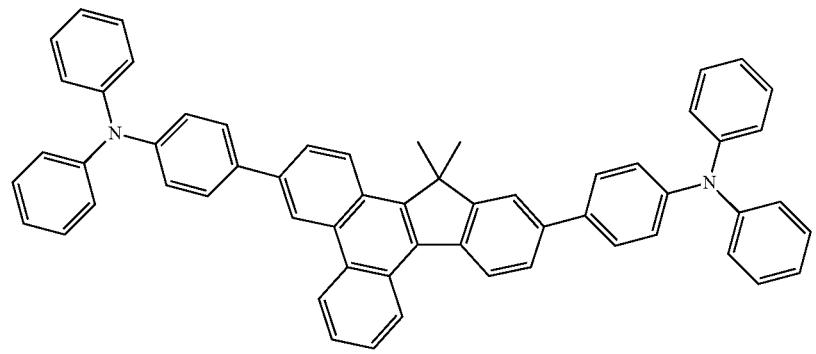
<Chemical Formula 56>
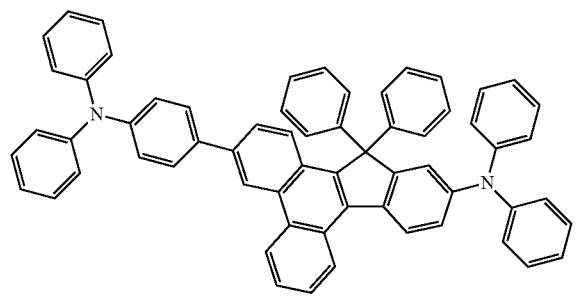
<Chemical Formula 57>
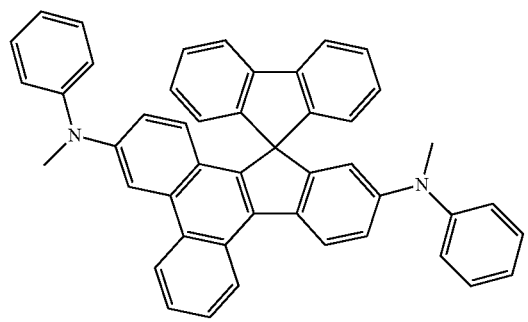
<Chemical Formula 58>
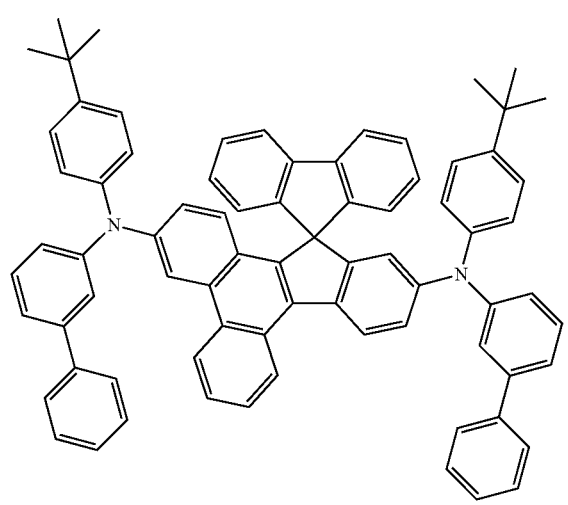

<Chemical Formula 59>

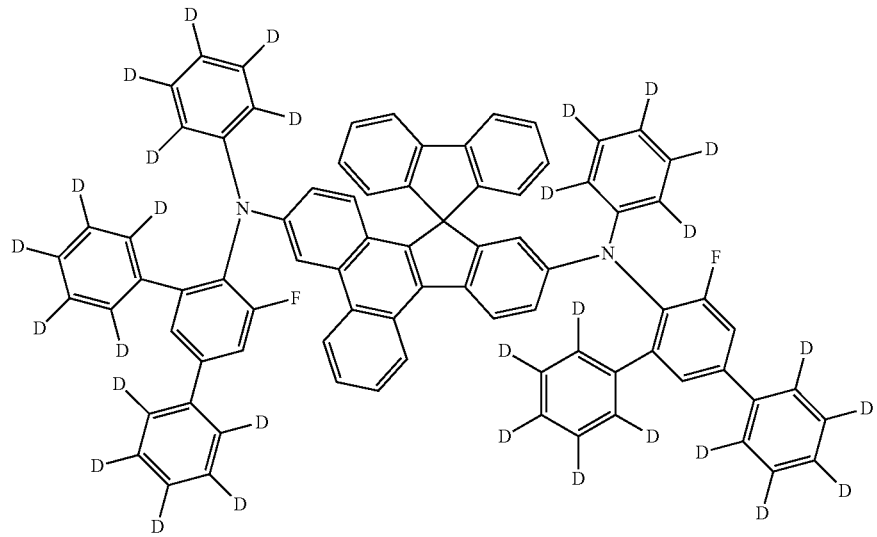

<Chemical Formula 60>

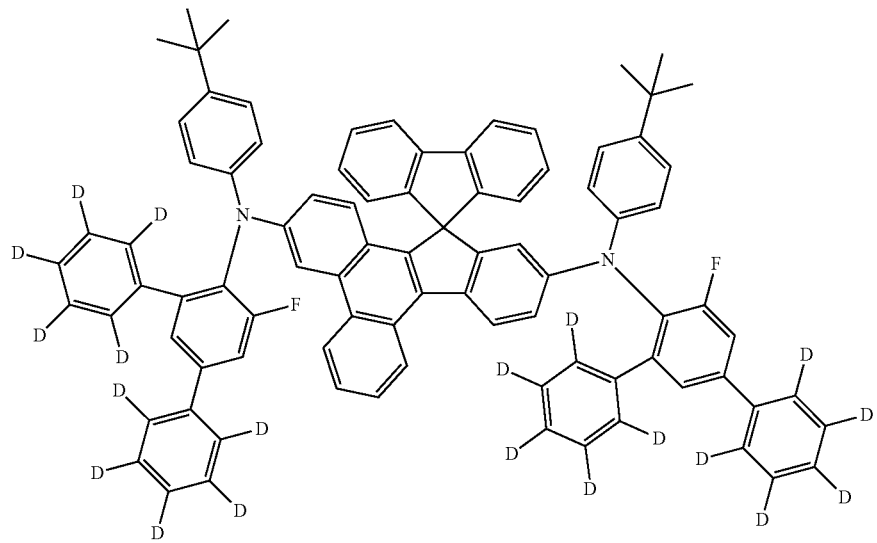

In the compounds represented by Chemical Formula B and Chemical Formula C, the anthracene ring moiety may have a substituted or unsubstituted aryl of 6 to 50 carbon atoms or a substituted or unsubstituted heteroaryl of 2 to 50 carbon atoms bonded at position 10 of the anthracene thereof and is directly connected to a dibenzofuran ring between position 9 of the anthracene ring moiety and position 1 or 2 of the dibenzofuran ring as shown in Diagram 1, below.

[Diagram 1]

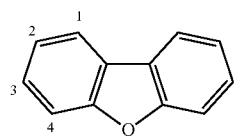

In Chemical Formula B and Chemical Formula C, the substituents $Ar_3$ may each be a substituted or unsubstituted aryl of 6 to 18 carbon atoms. In this case, $Ar_3$ may be a substituent represented by the following Structural Formula C:

[Structural Formula C]

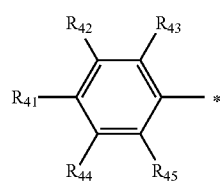

wherein $R_{41}$ to $R_{45}$ are the same or different and are each as defined above for $R_{14}$ to $R_{19}$, adjacent substituents of which may bond to each other to form a saturate or unsaturated ring.

Concrete examples of the anthracene compounds represented by Chemical Formula B or C include the following [Compound 1] to [Compound 180], but are not limited thereto:

<Compound 1>
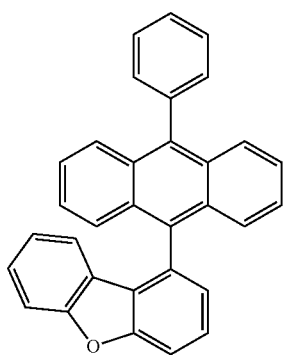
<Compound 2>
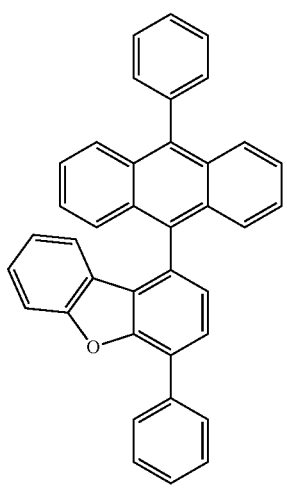
<Compound 3>
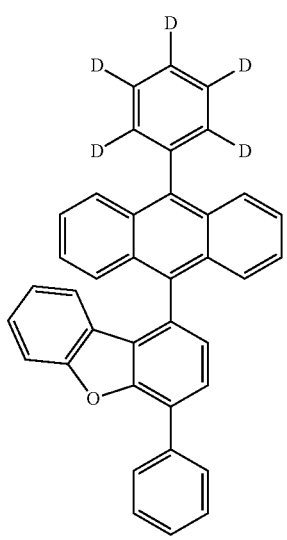
<Compound 4>
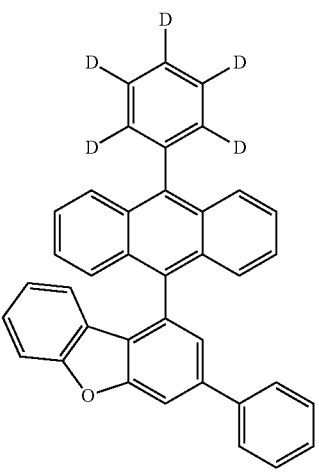
<Compound 5>
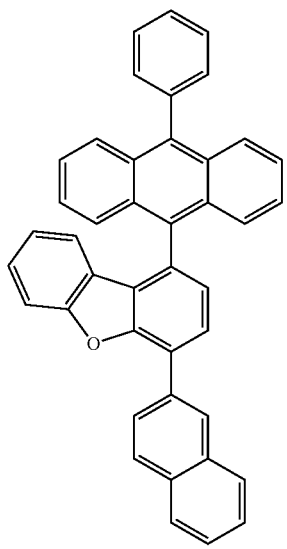
<Compound 6>
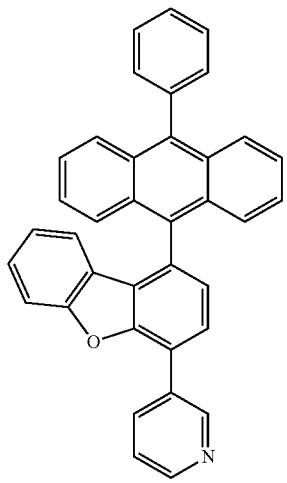

<Compound 7>
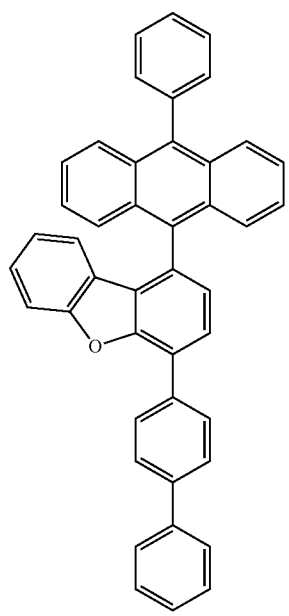
<Compound 8>
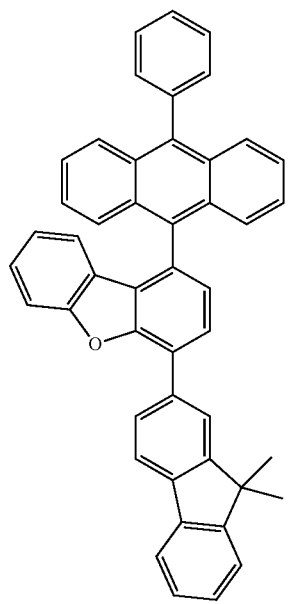
<Compound 9>
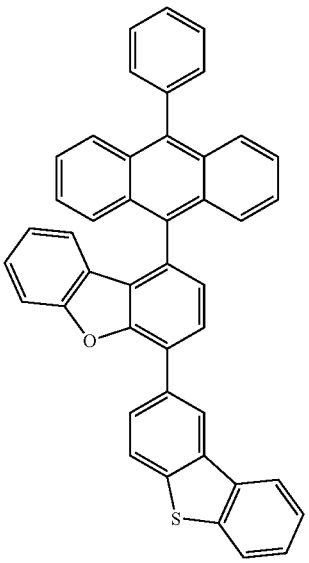
<Compound 10>
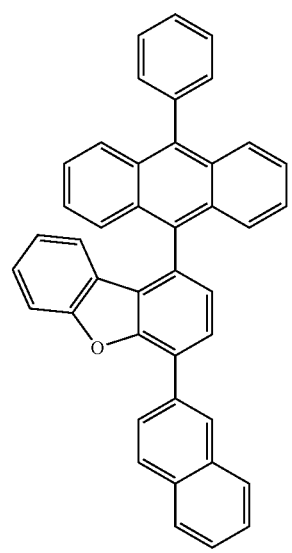
<Compound 11>
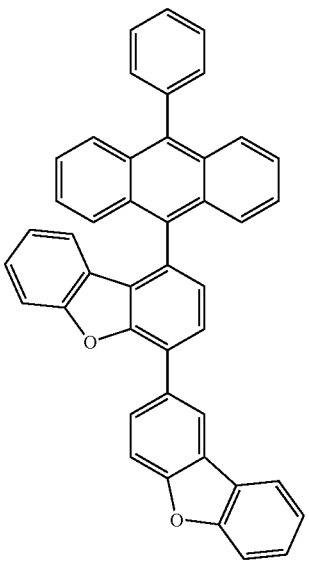

<Compound 12>
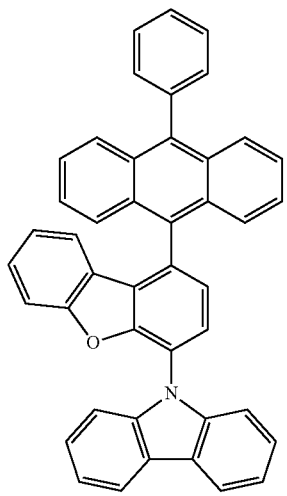
<Compound 13>
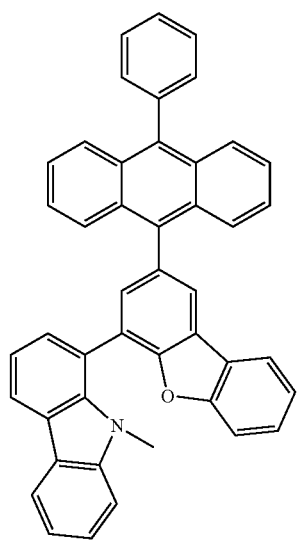
<Compound 14>
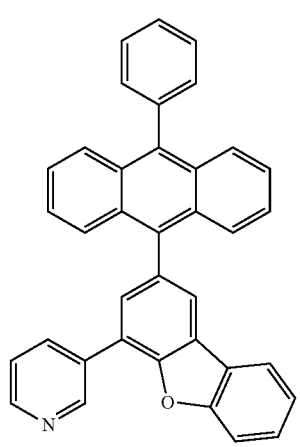
<Compound 15>
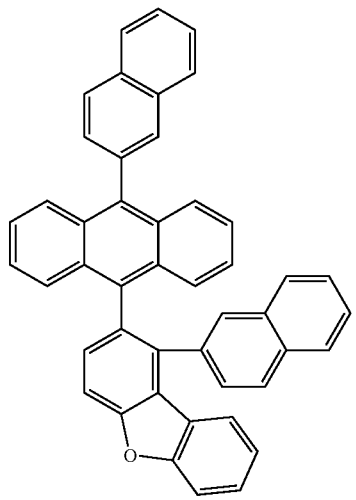
<Compound 16>
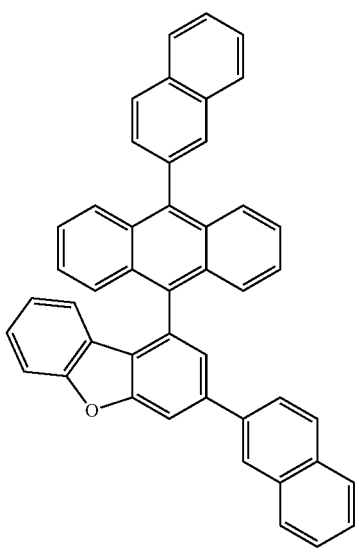
<Compound 17>
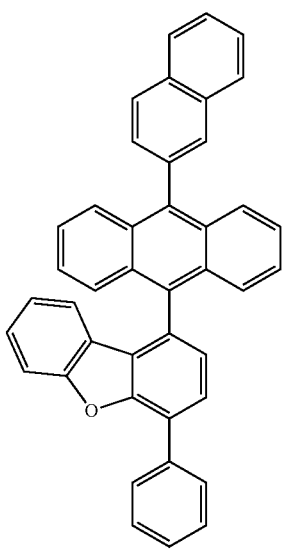

-continued
<Compound 18>
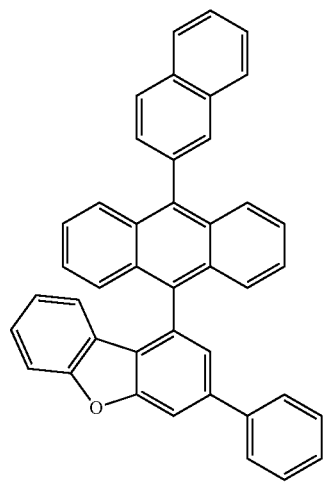
<Compound 19>
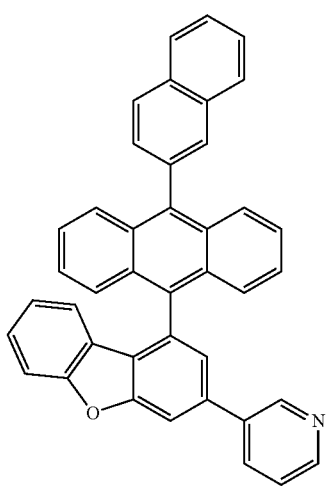
<Compound 20>
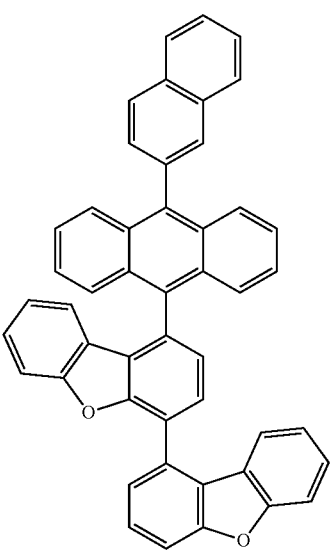
-continued
<Compound 21>
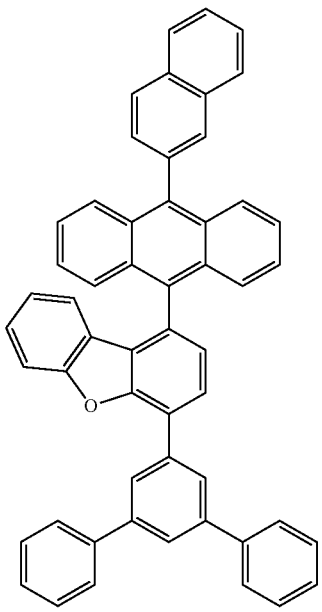
<Compound 22>
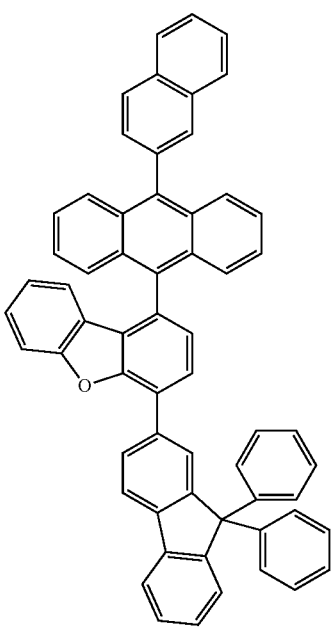

<Compound 23>
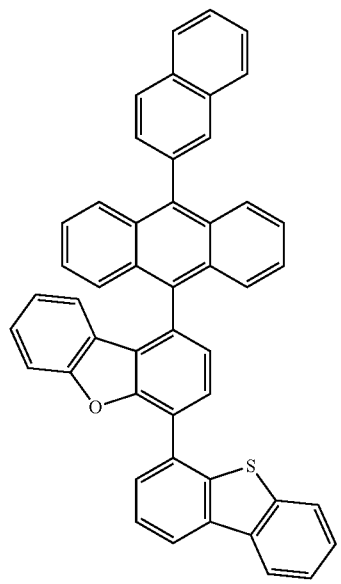
<Compound 24>
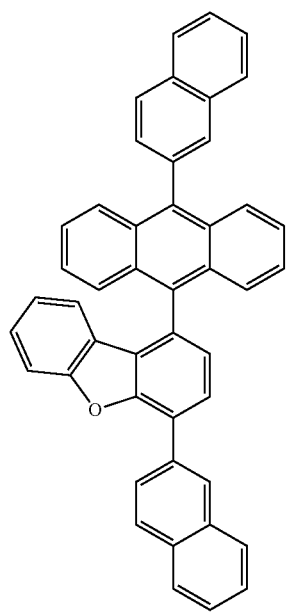
<Compound 25>
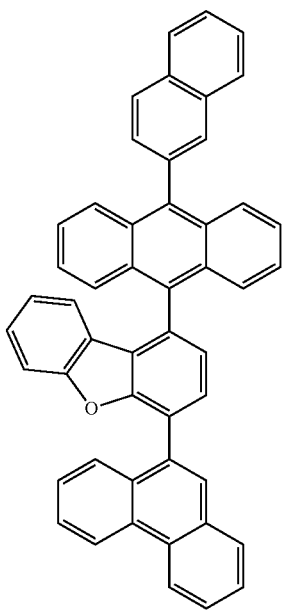
<Compound 26>
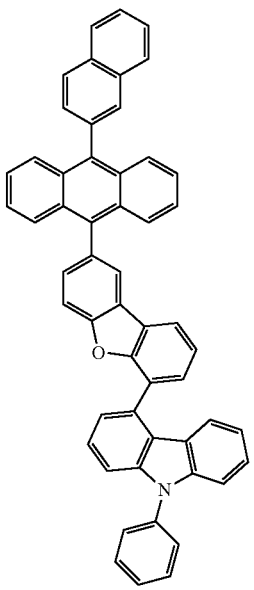

<Compound 27>
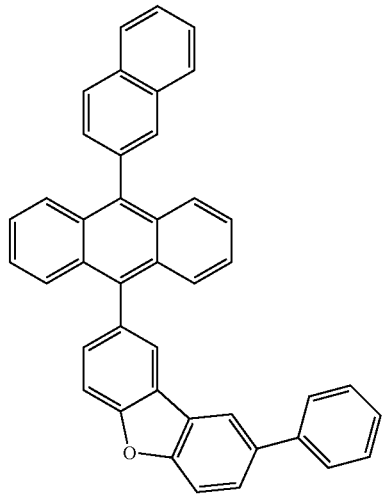
<Compound 28>
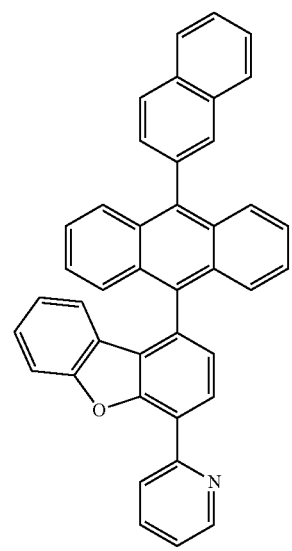
<Compound 29>
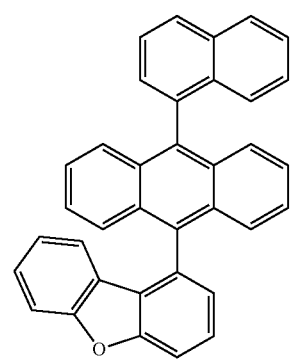
<Compound 30>
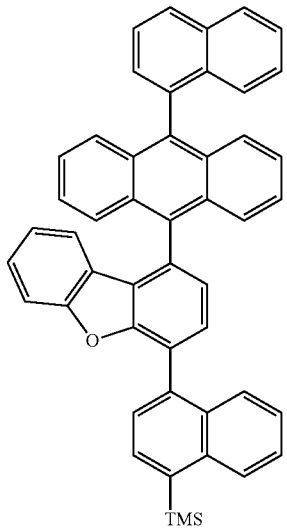
<Compound 31>
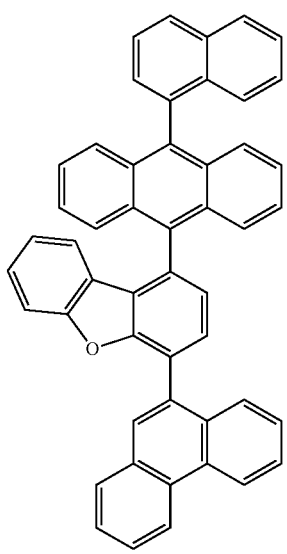
<Compound 32>
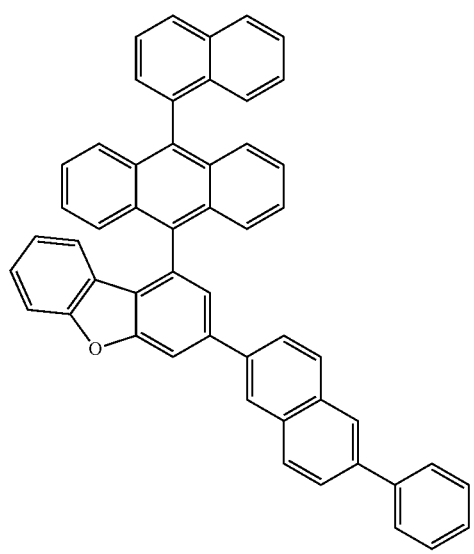

<Compound 33>
<Compound 34>
<Compound 35>
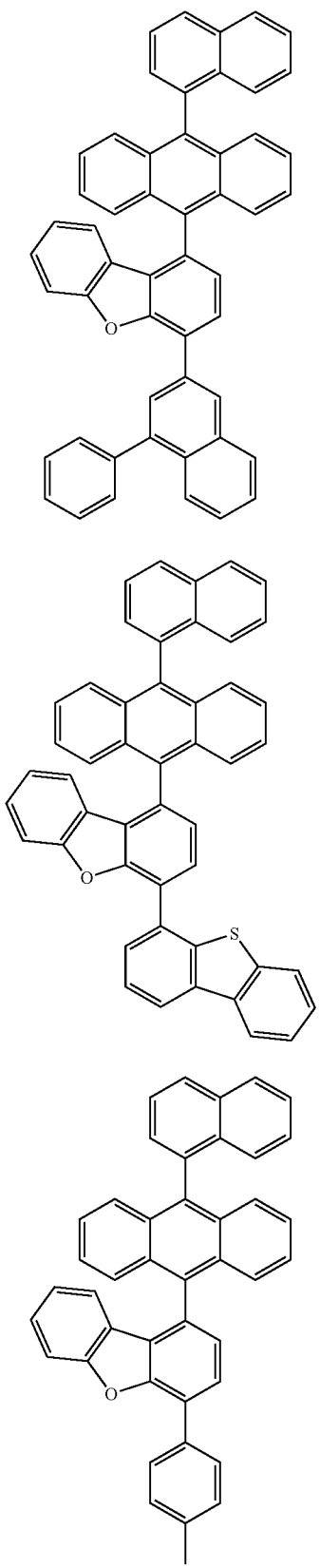
<Compound 36>
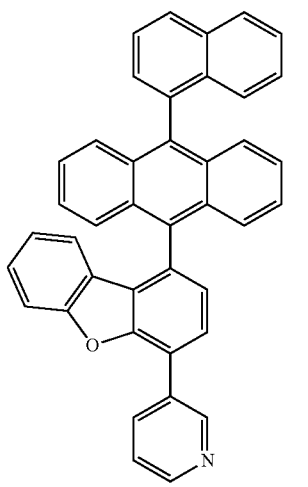
<Compound 37>
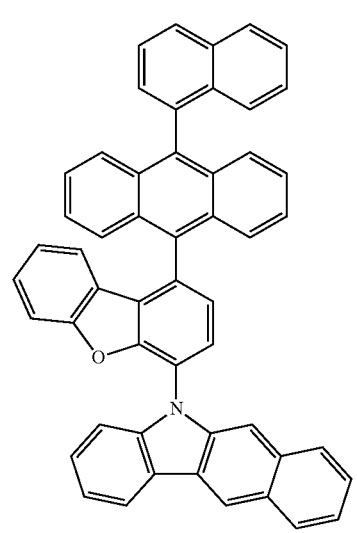
<Compound 38>
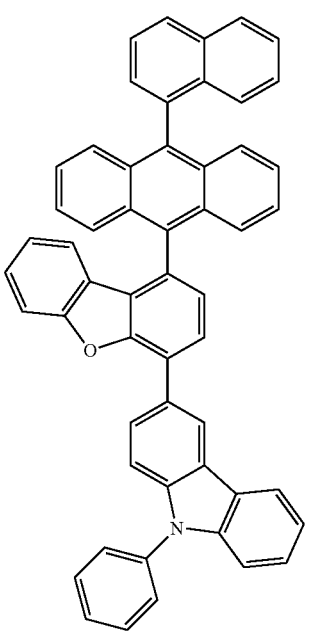

<Compound 39>
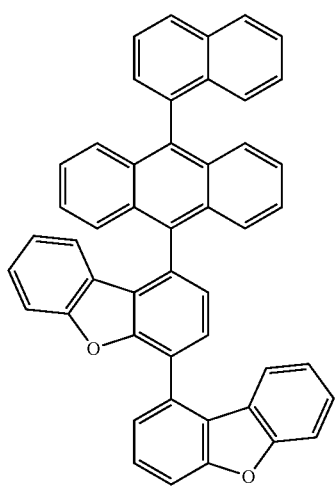
<Compound 40>
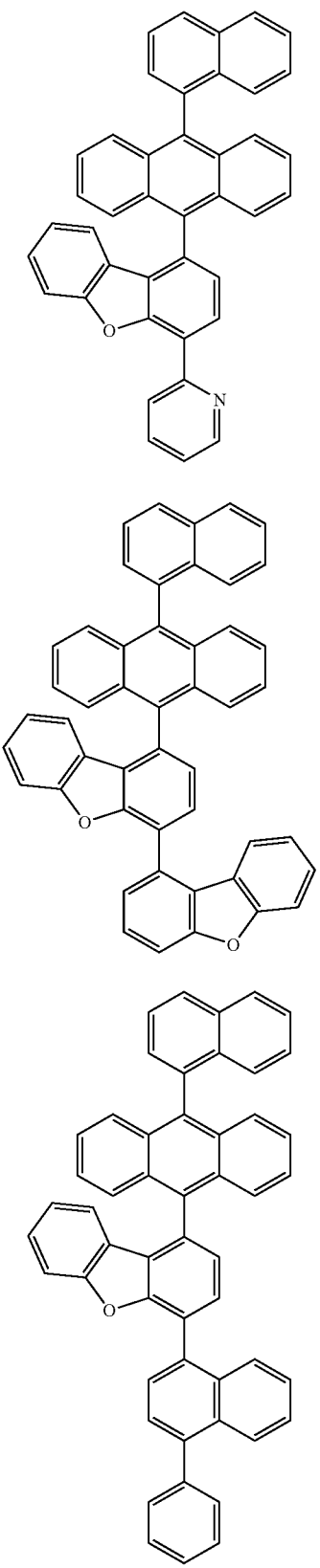
<Compound 41>
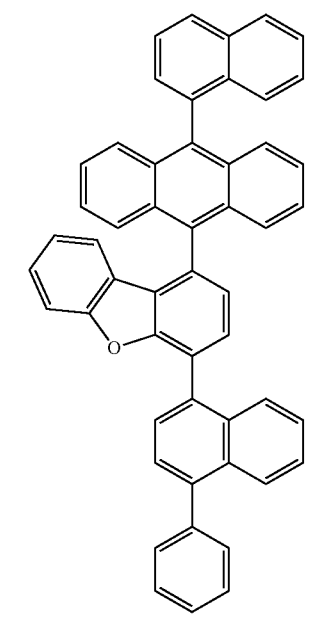
<Compound 42>
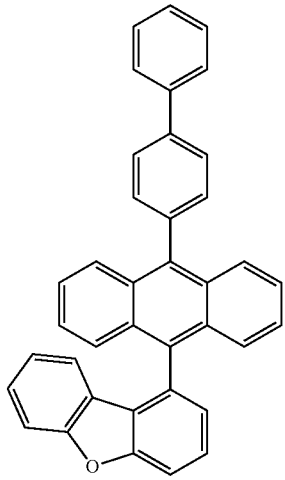
<Compound 43>
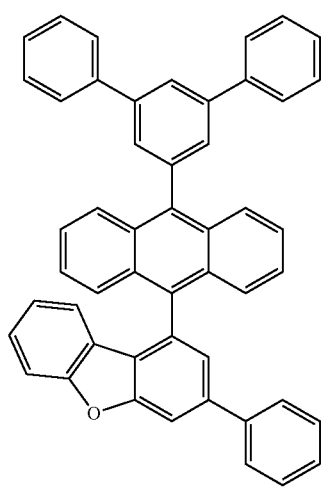
<Compound 44>
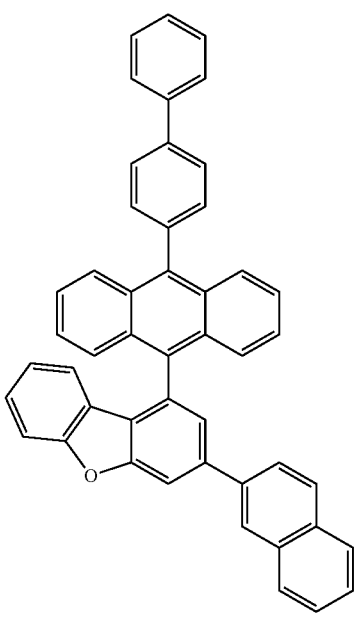

<Compound 45>
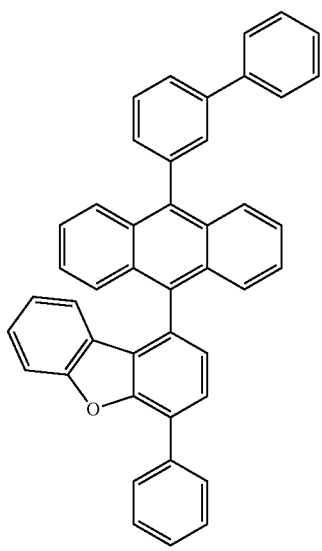
<Compound 47>
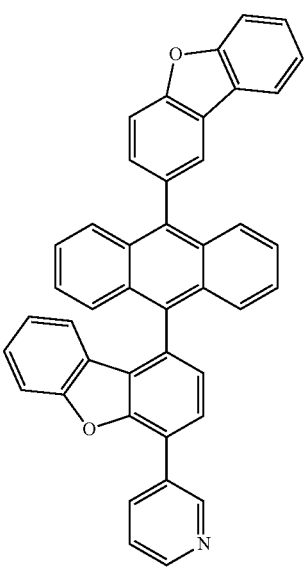
<Compound 46>
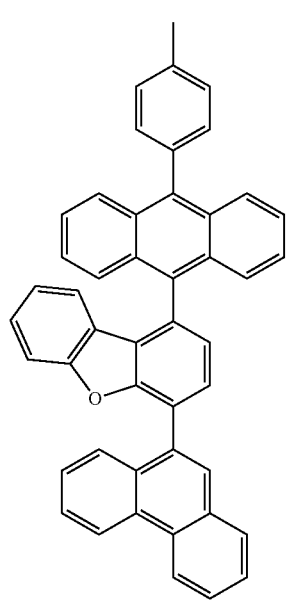
<Compound 48>

<Compound 49>
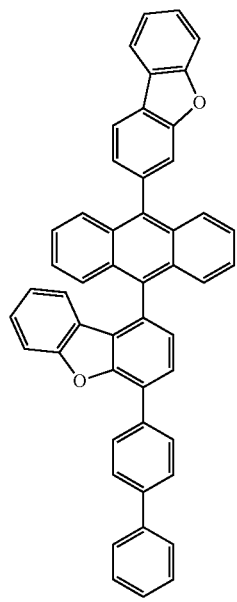
<Compound 50>
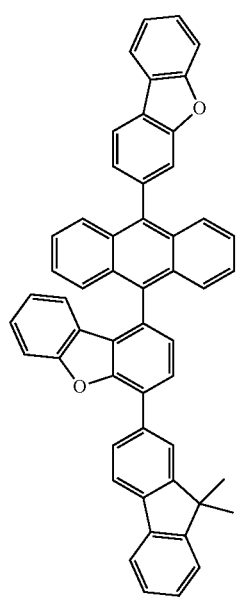
<Compound 51>
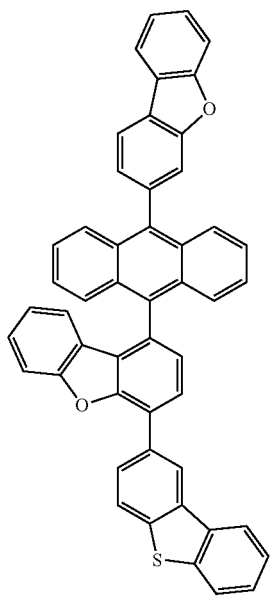
<Compound 52>
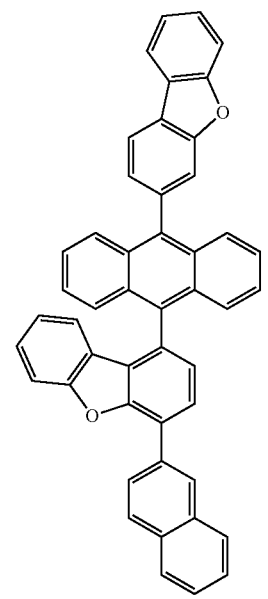

<Compound 53>
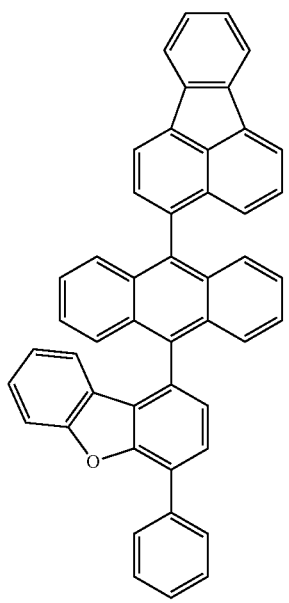
<Compound 54>
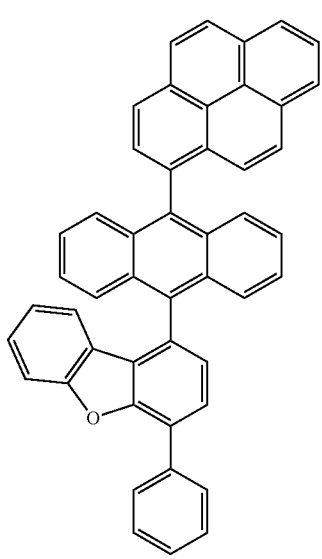
<Compound 55>
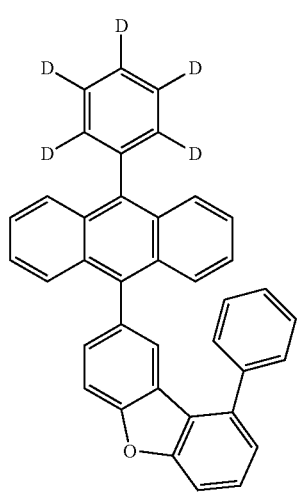
<Compound 56>
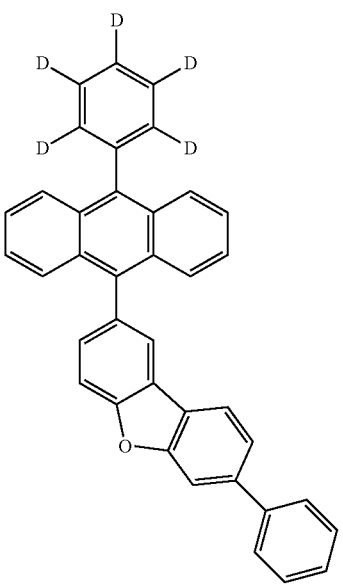
<Compound 57>
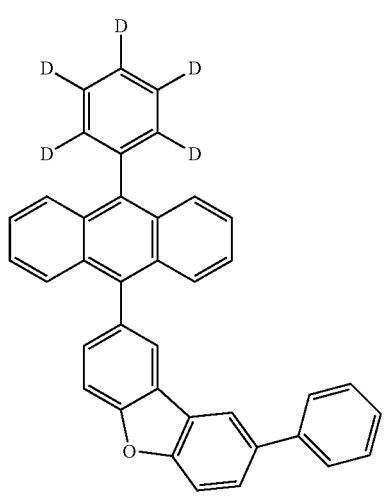

<Compound 58>
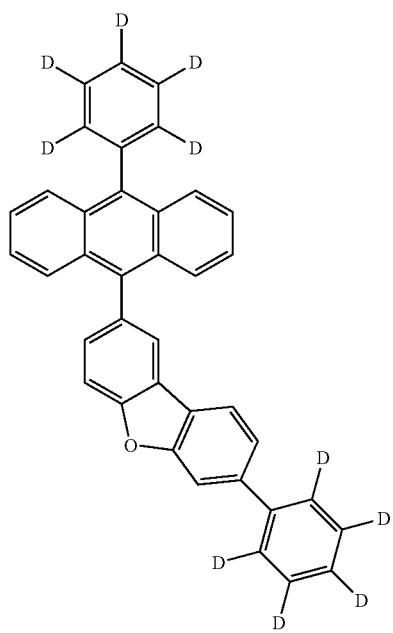
<Compound 60>
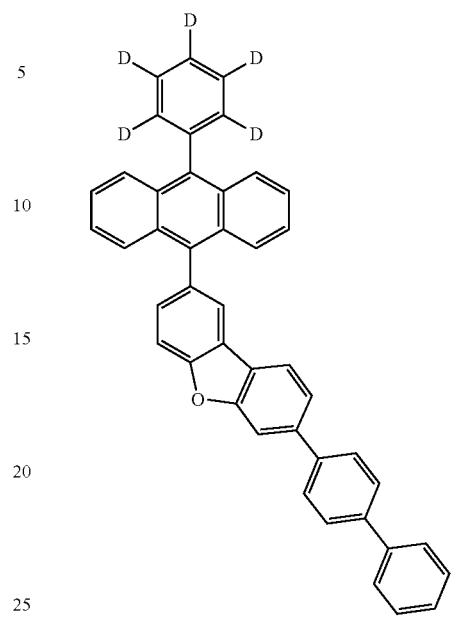
<Compound 61>
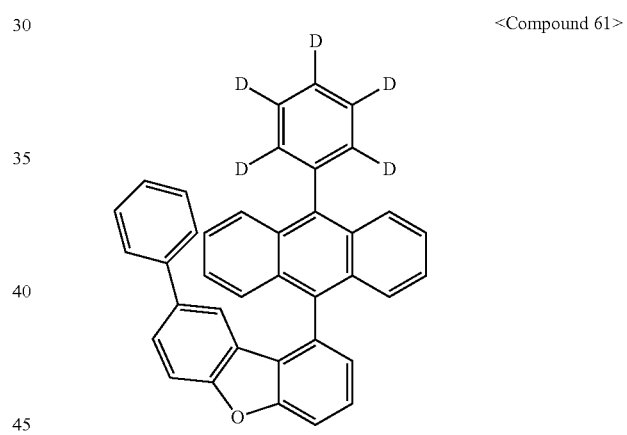
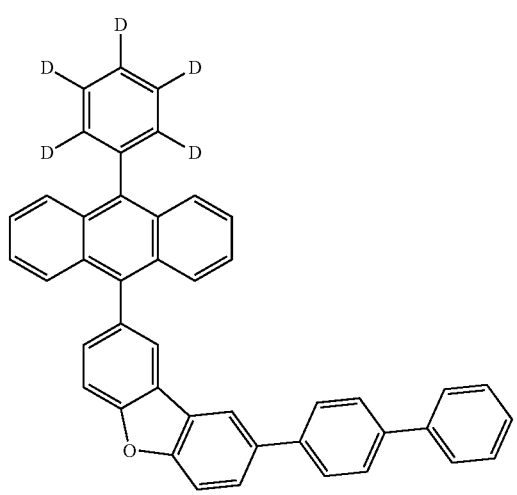
<Compound 62>
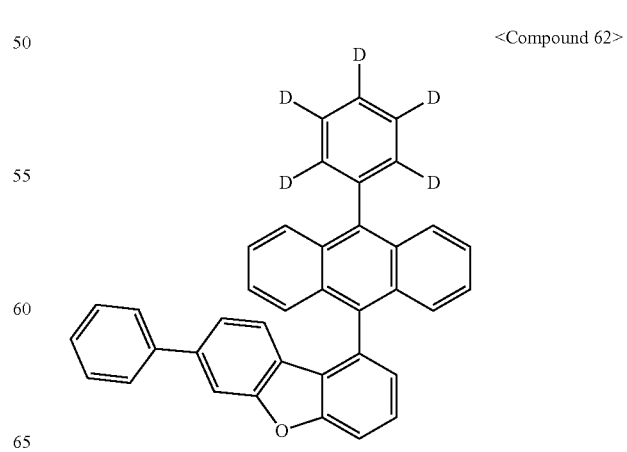

<Compound 63>
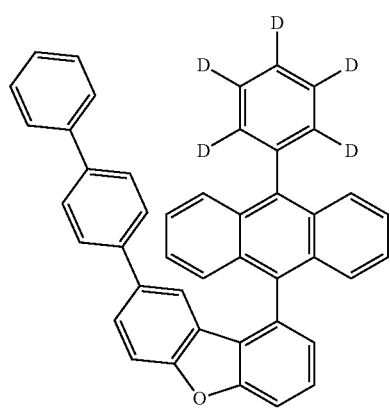
<Compound 64>
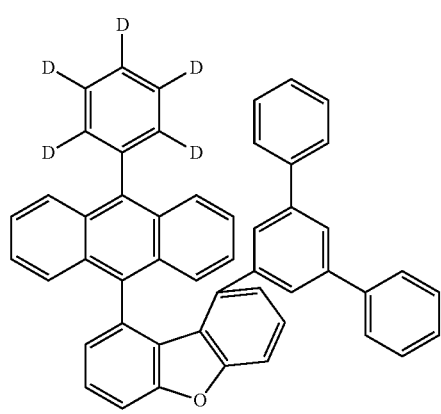
<Compound 65>
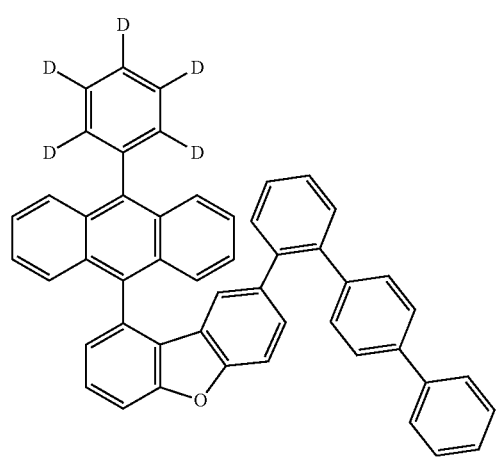
<Compound 66>
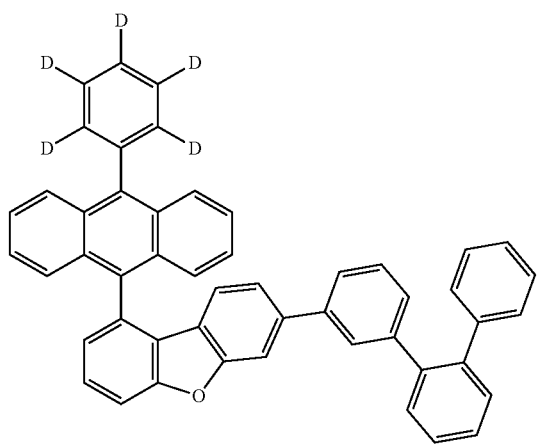
<Compound 67>
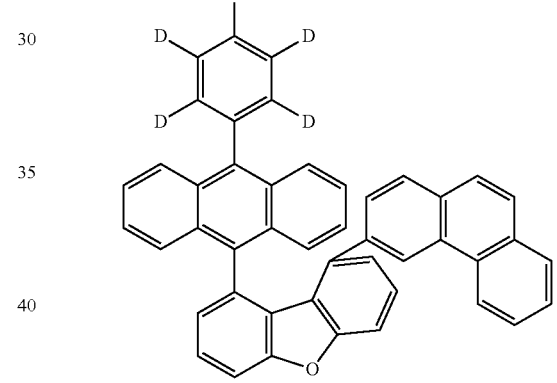
<Compound 68>
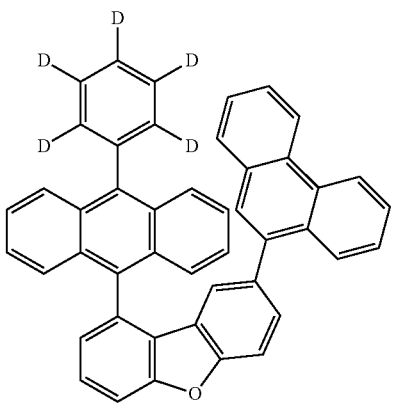

<Compound 69>
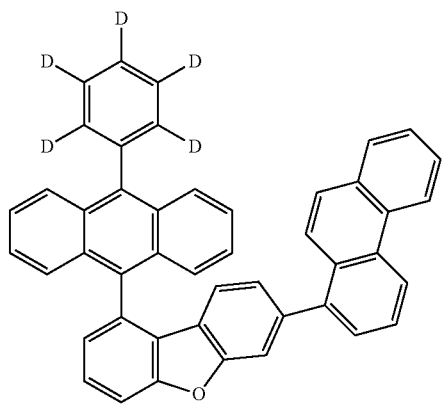
<Compound 70>
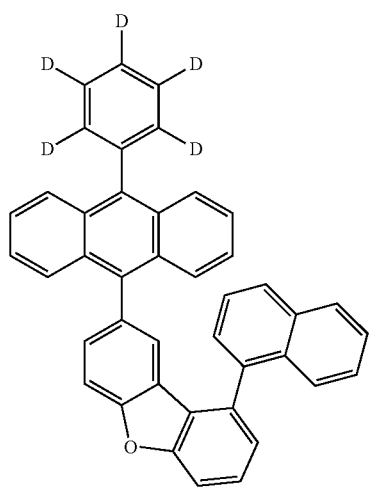
<Compound 71>
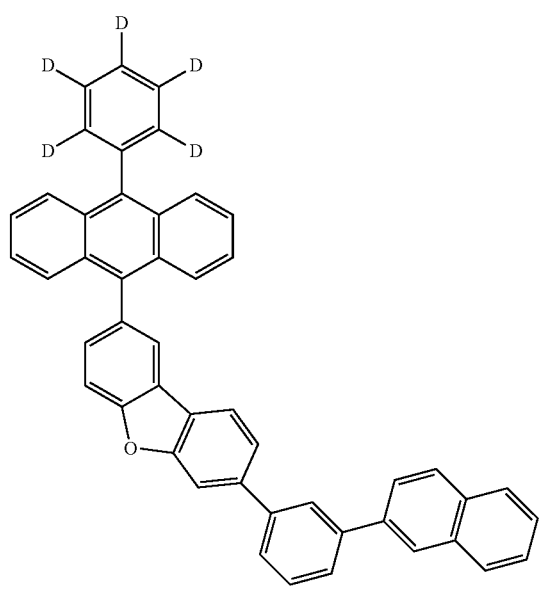
<Compound 72>
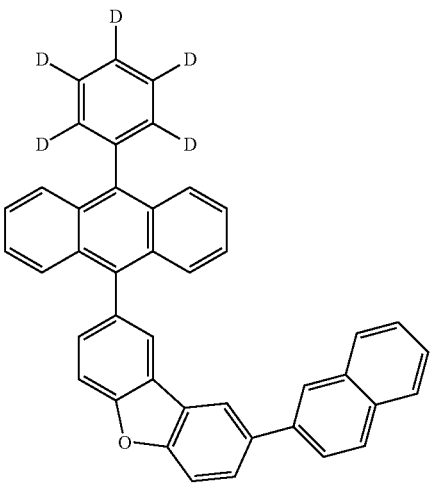
<Compound 73>
<Compound 74>
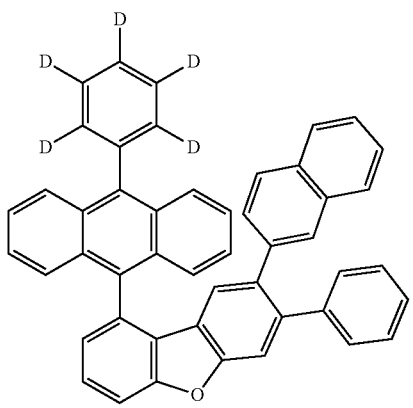

<Compound 75>
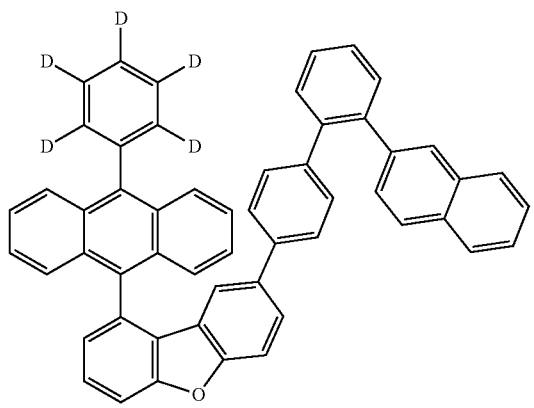
<Compound 76>
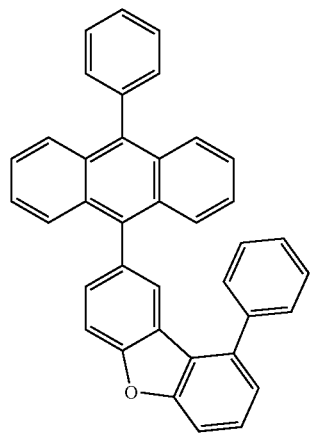
<Compound 77>
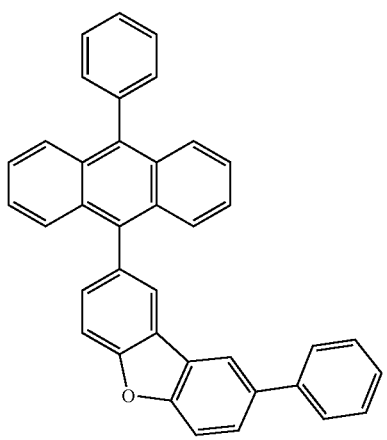
<Compound 78>
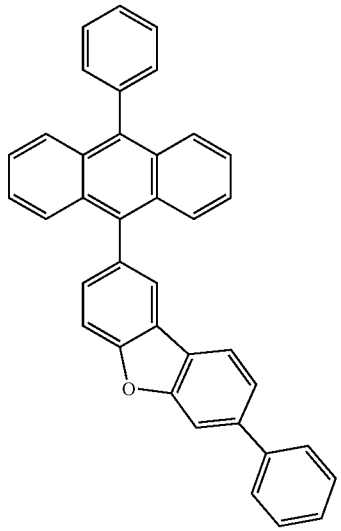
<Compound 79>
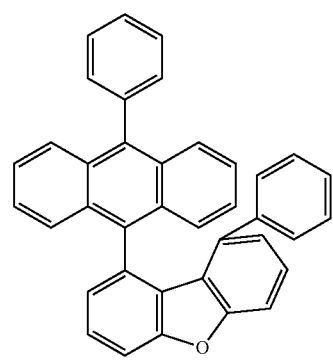
<Compound 80>
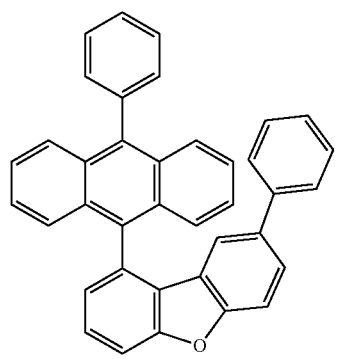
<Compound 81>
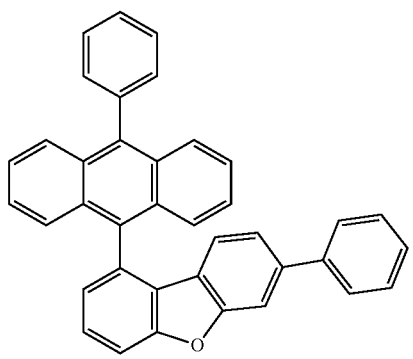

<Compound 82>
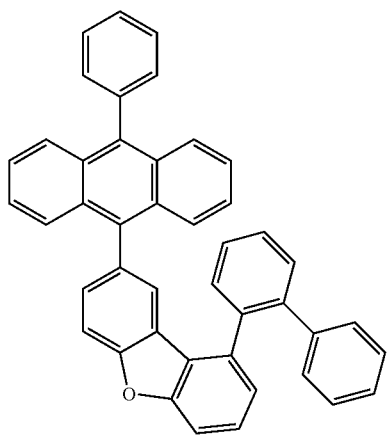
<Compound 83>
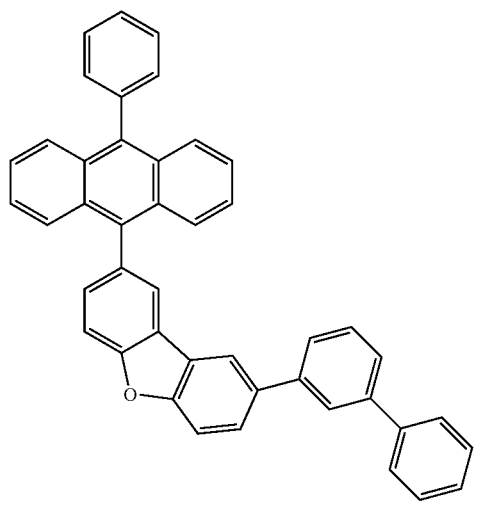
<Compound 84>
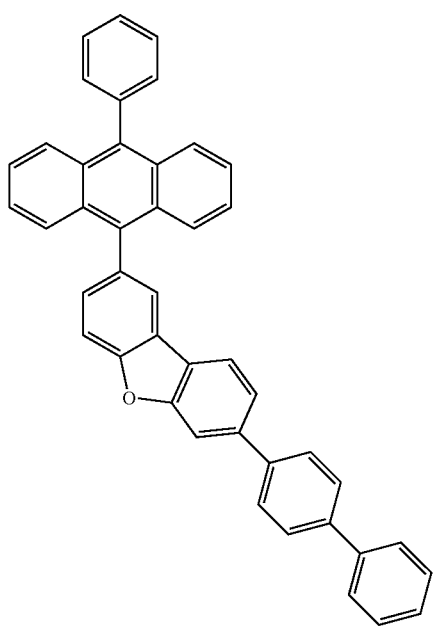
<Compound 85>
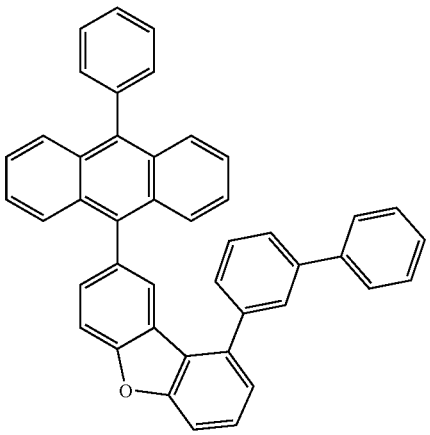
<Compound 86>
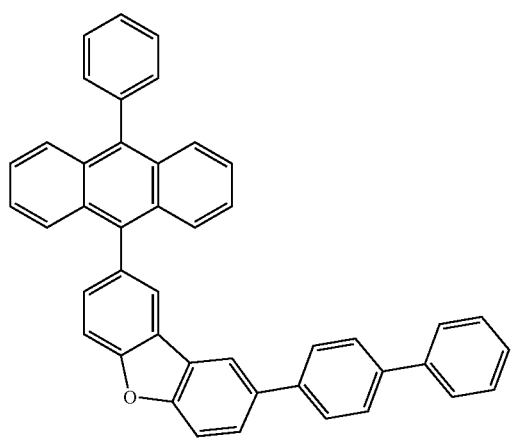
<Compound 87>

<Compound 88>
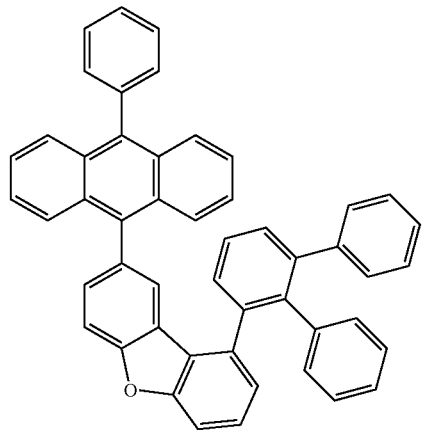
<Compound 89>
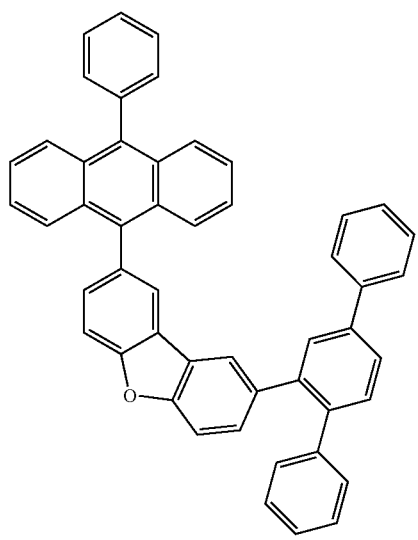
<Compound 90>
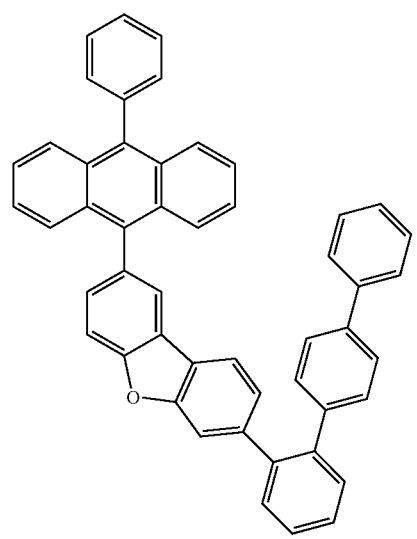
<Compound 91>
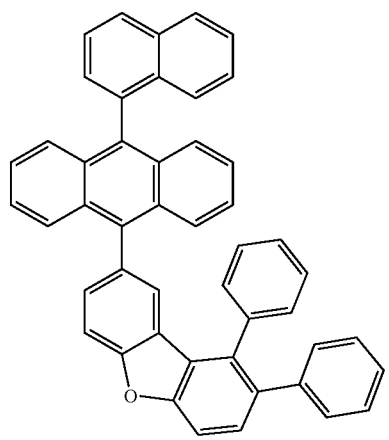
<Compound 92>
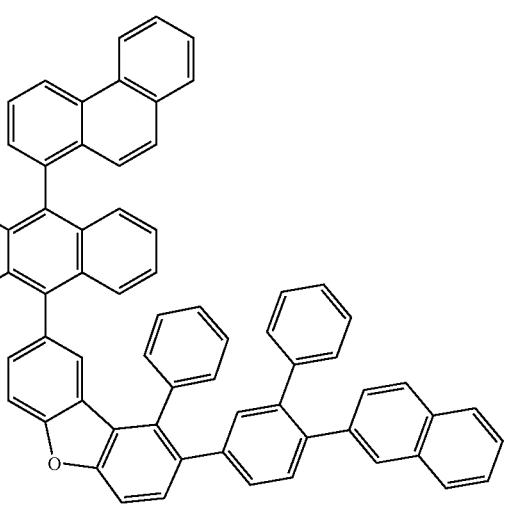
<Compound 93>
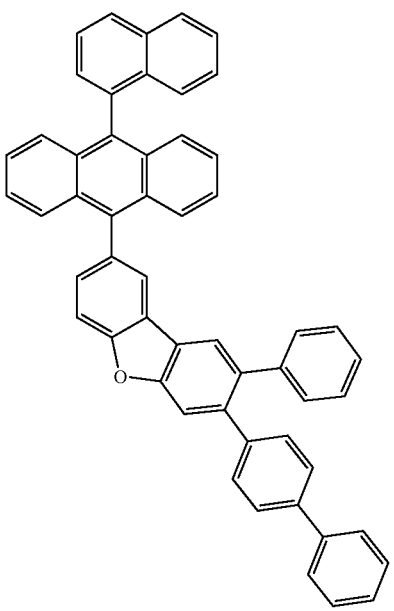

<Compound 94>
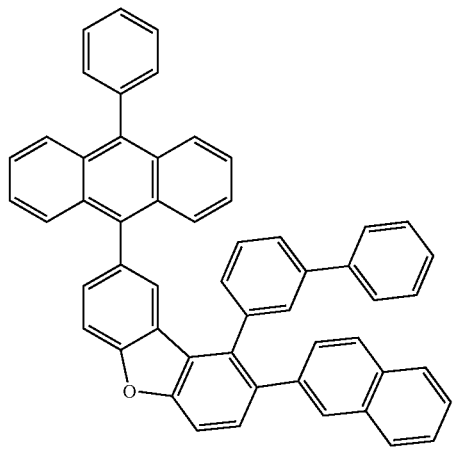
<Compound 95>
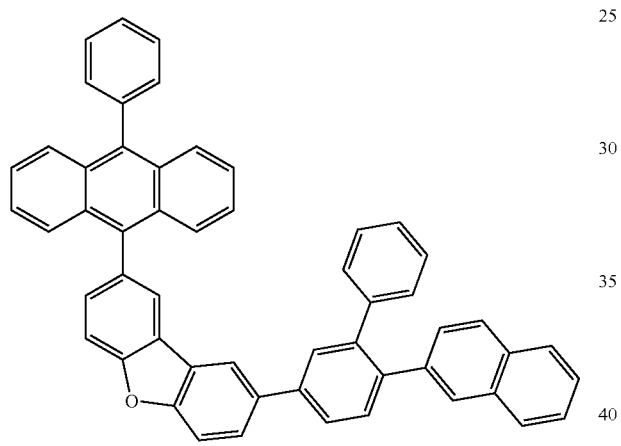
<Compound 96>
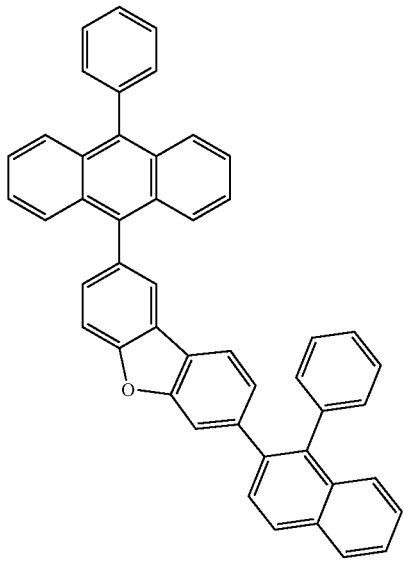
<Compound 97>
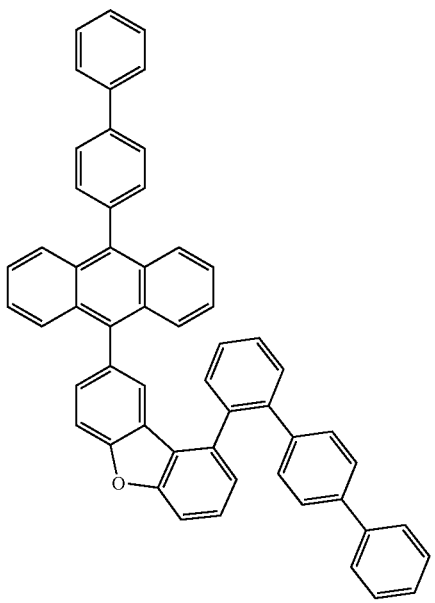
<Compound 98>
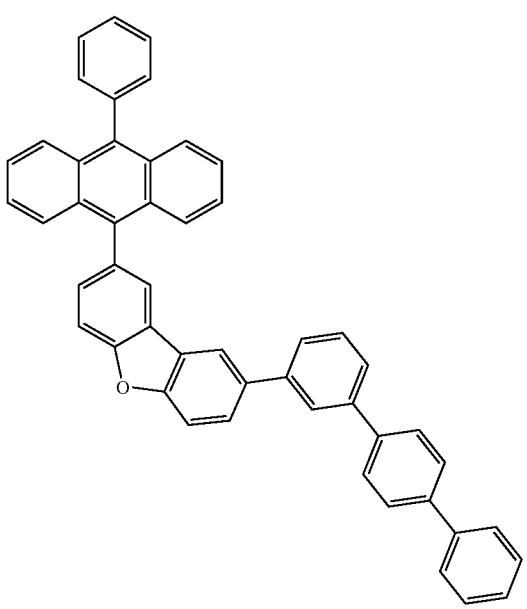

<Compound 99>
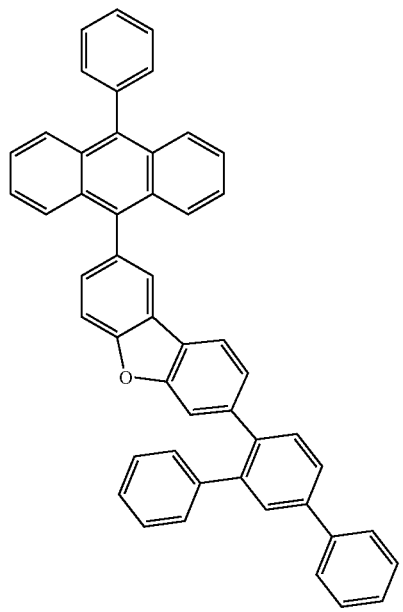
<Compound 100>
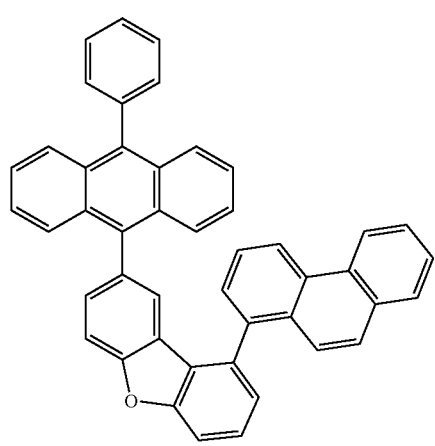
<Compound 101>
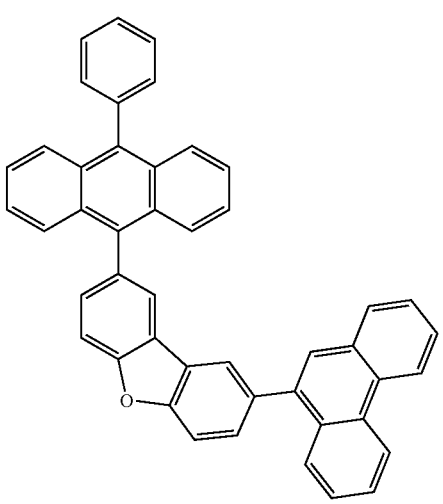
<Compound 102>
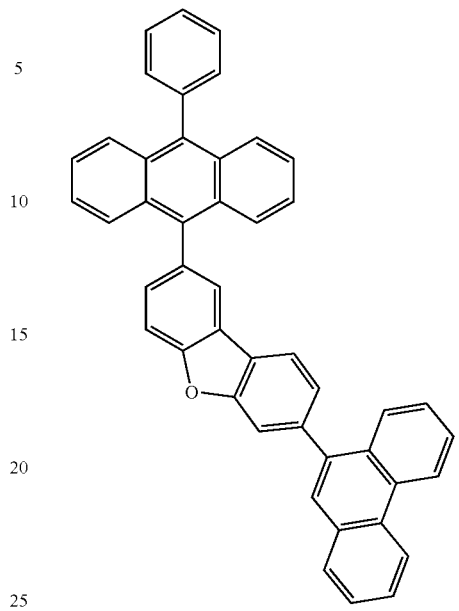
<Compound 103>
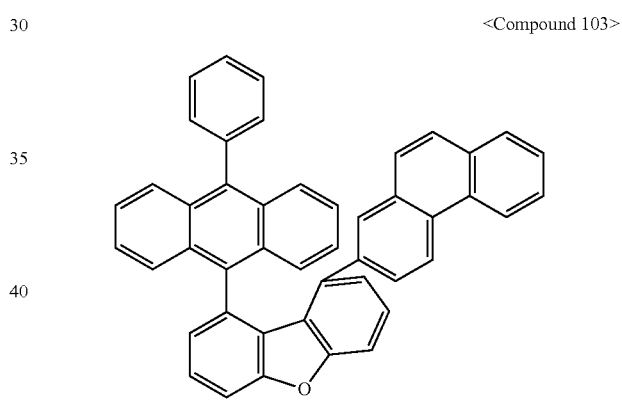
<Compound 104>
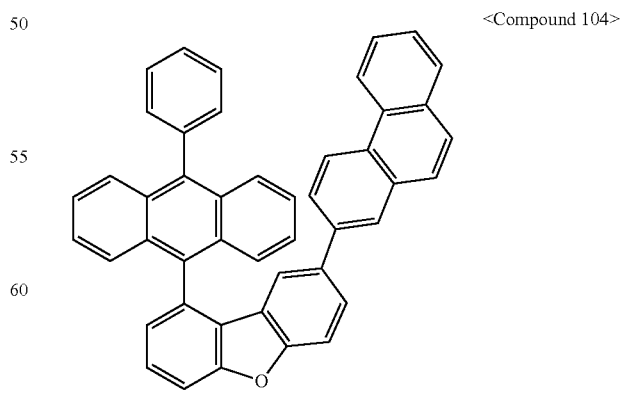

<Compound 105>
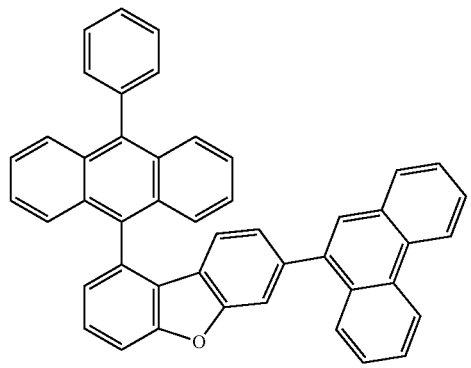
<Compound 106>
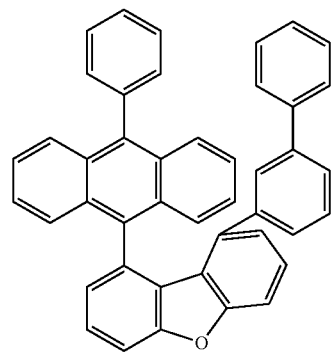
<Compound 107>
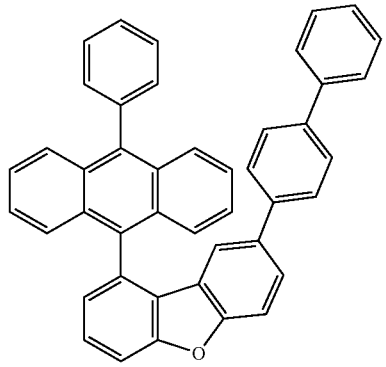
<Compound 108>
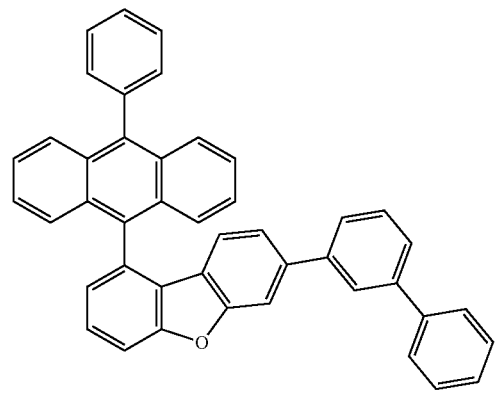
<Compound 109>
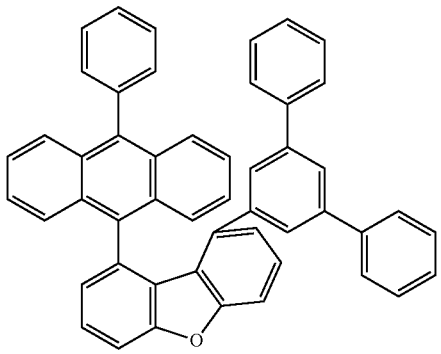
<Compound 110>
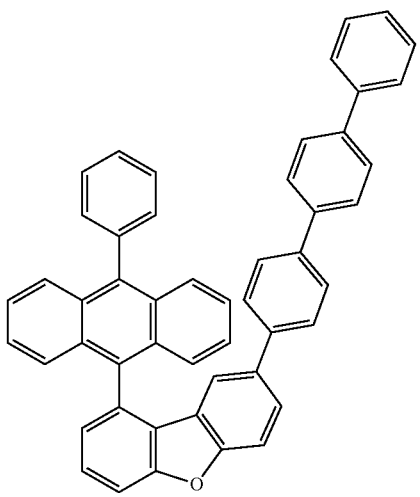
<Compound 111>
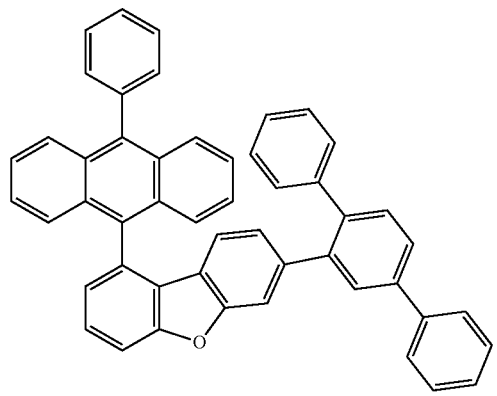
<Compound 112>
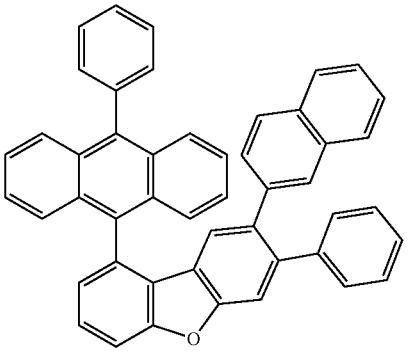

<Compound 113>
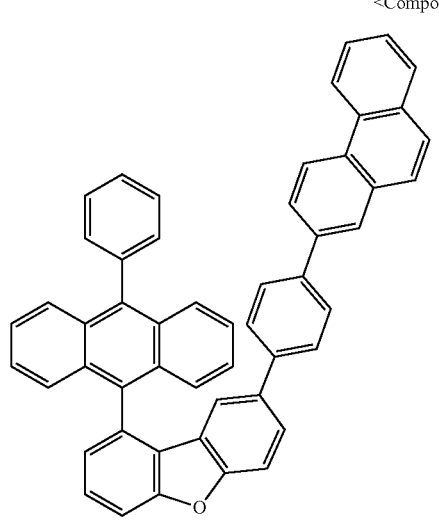
<Compound 114>
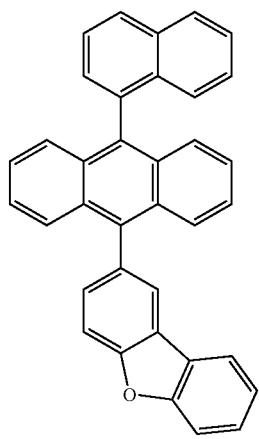
<Compound 115>
<Compound 116>
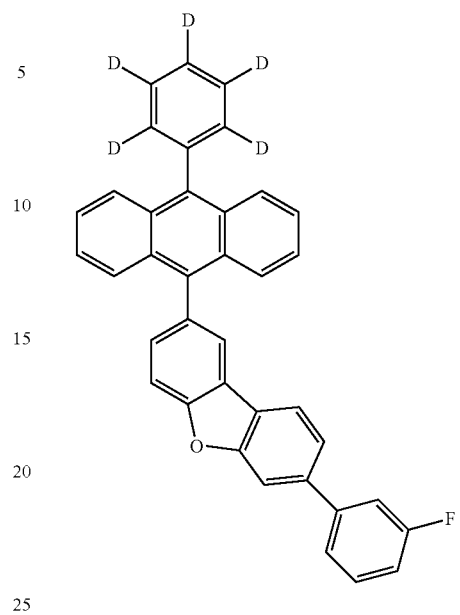
<Compound 117>
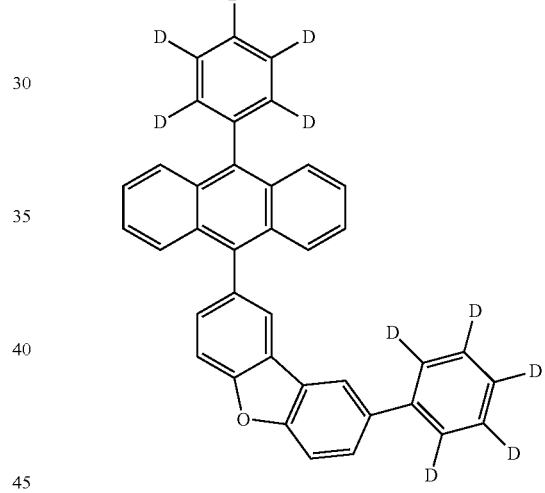
<Compound 118>
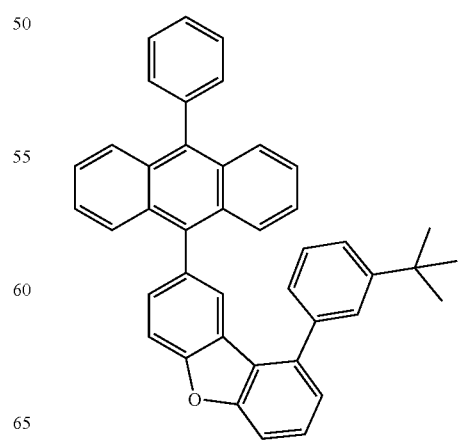

<Compound 119>
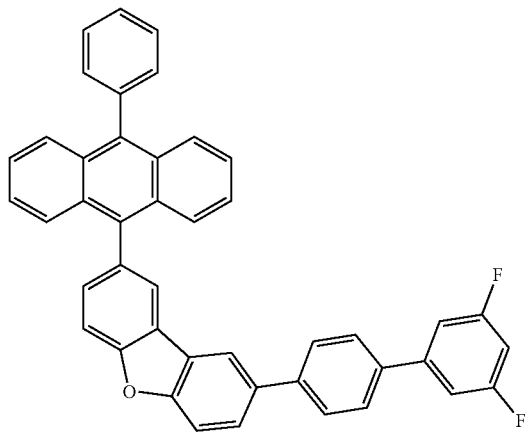
<Compound 120>
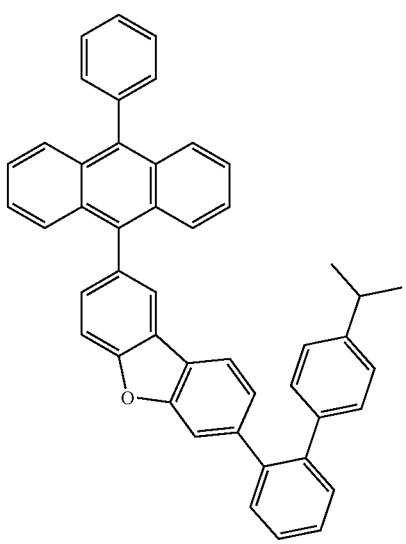
<Compound 121>
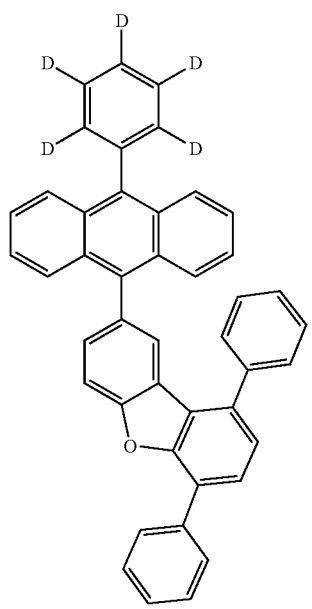
<Compound 122>
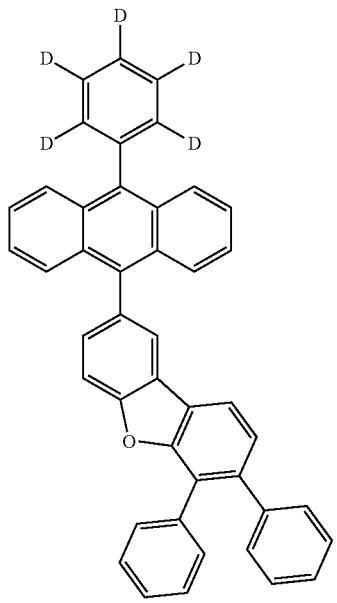
<Compound 123>
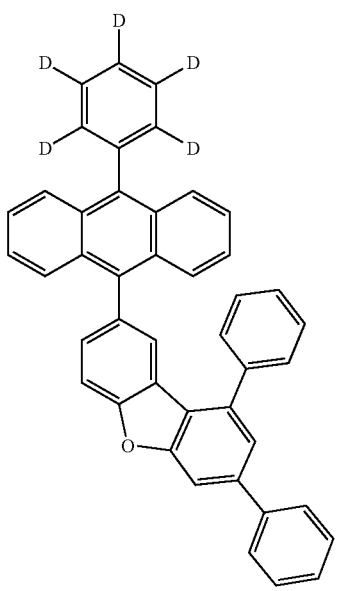

<Compound 124>
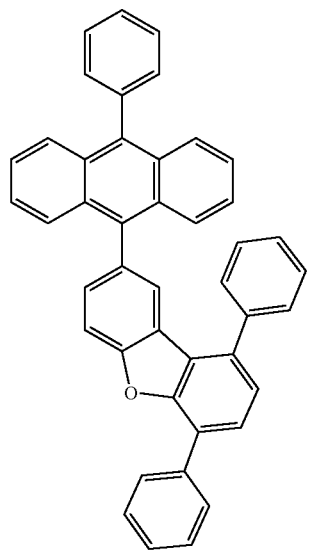
<Compound 125>
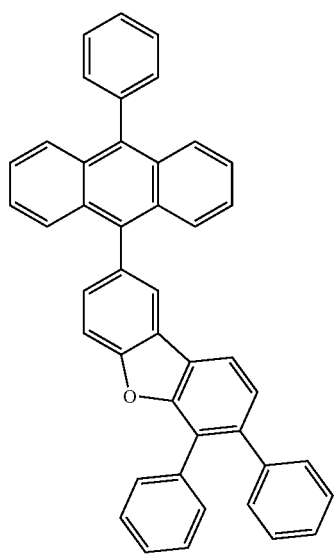
<Compound 126>
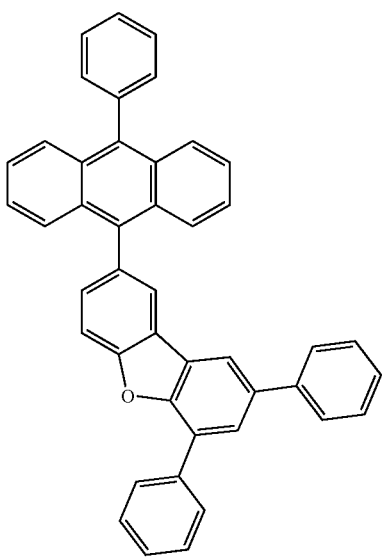
<Compound 127>
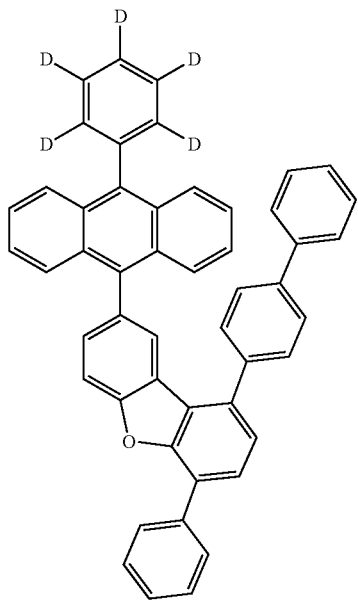
<Compound 128>
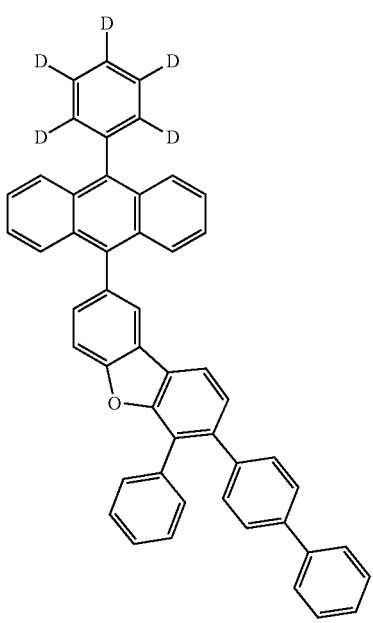

<Compound 129>
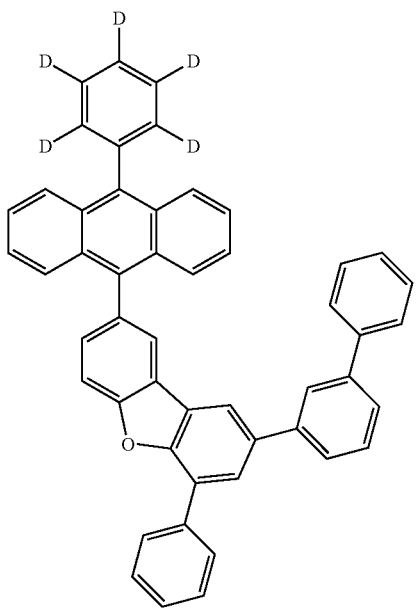
<Compound 130>
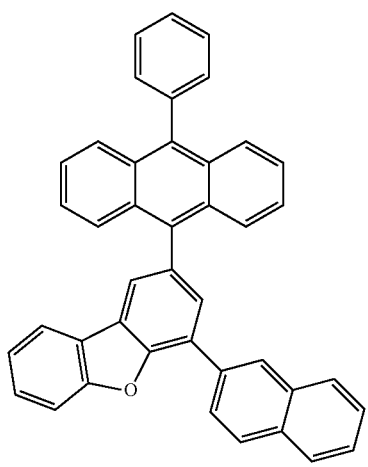
<Compound 131>
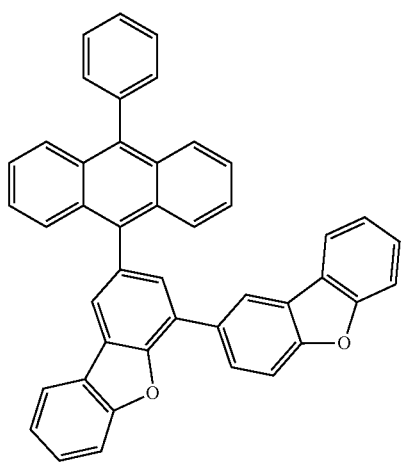
<Compound 132>
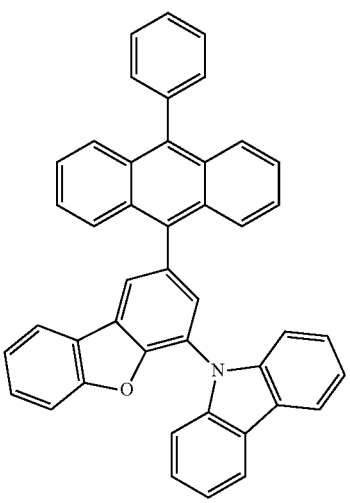
<Compound 133>
<Compound 134>
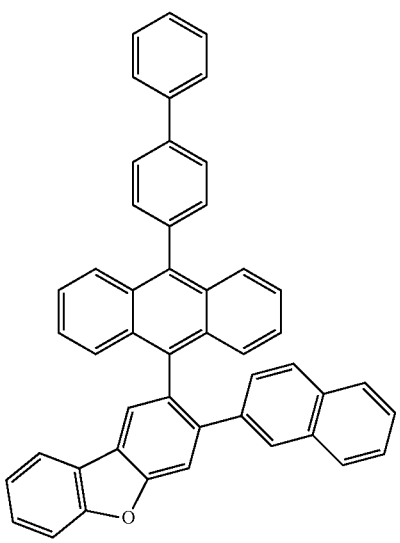

<Compound 135>
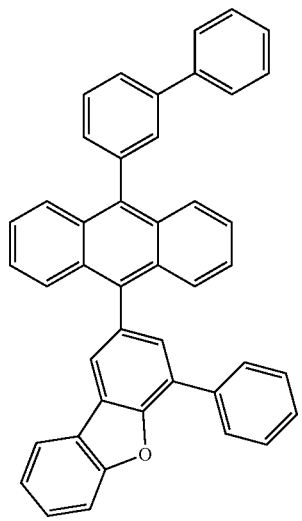
<Compound 136>
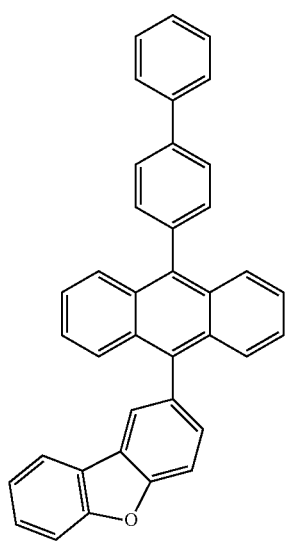
<Compound 137>
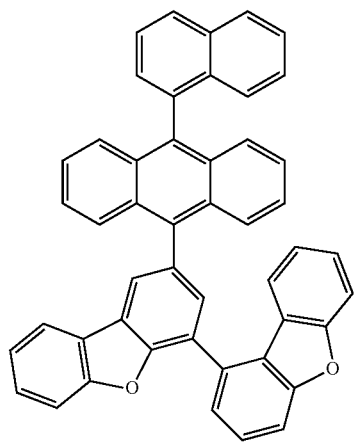
<Compound 138>
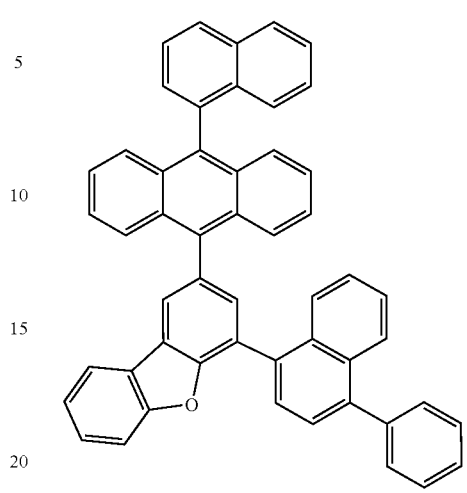
<Compound 139>
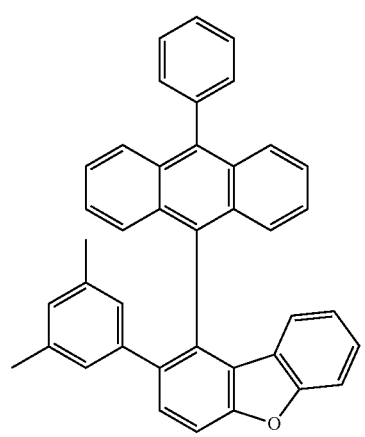
<Compound 140>
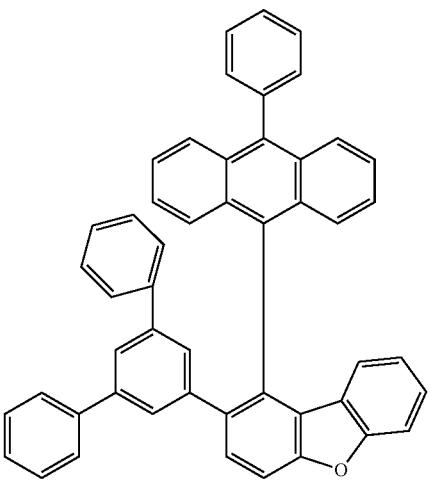

<Compound 141>
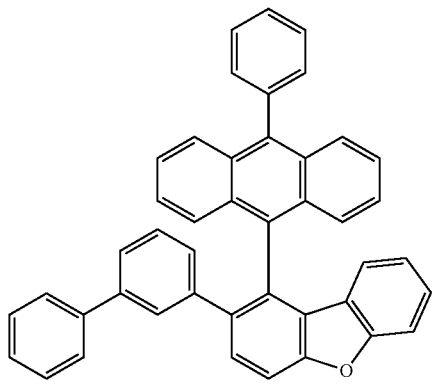
<Compound 142>
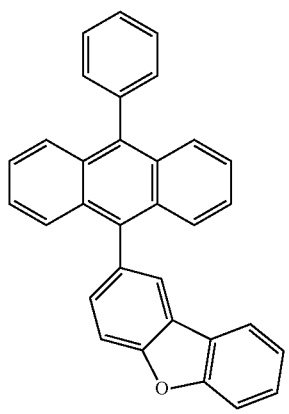
<Compound 143>
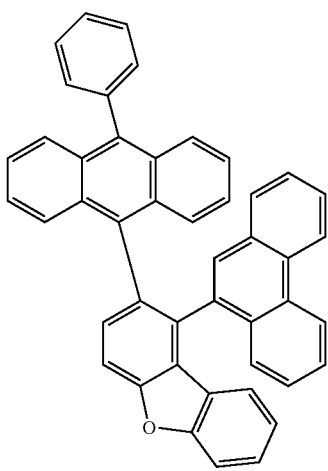
<Compound 144>
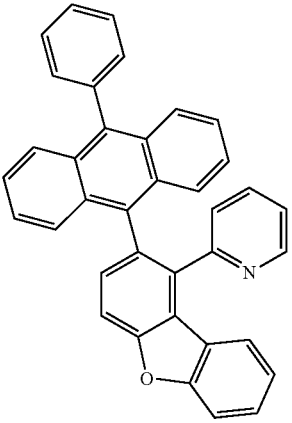
<Compound 145>
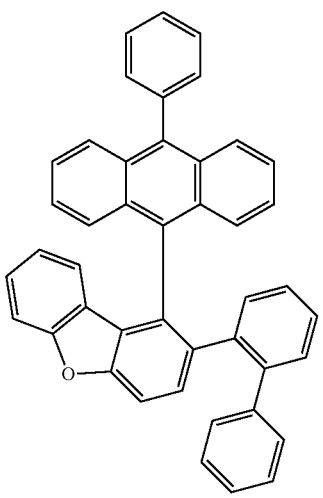
<Compound 146>
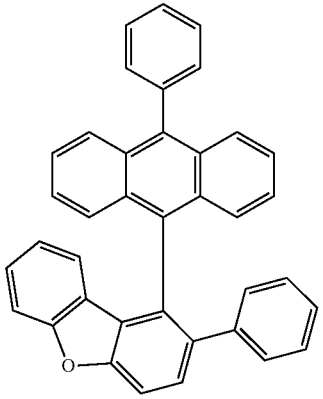

<Compound 147>
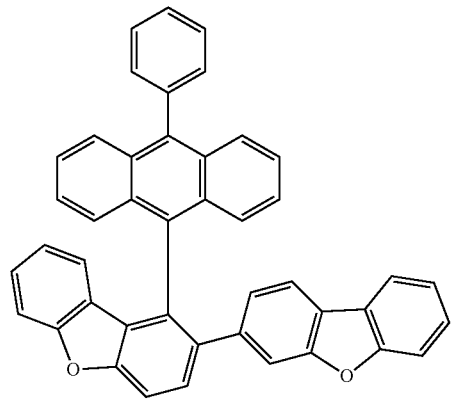
<Compound 150>
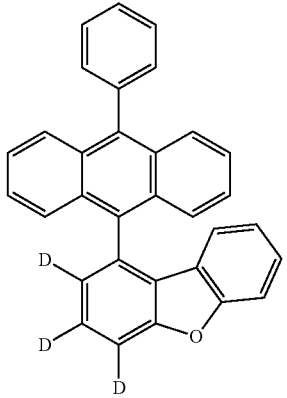
<Compound 148>
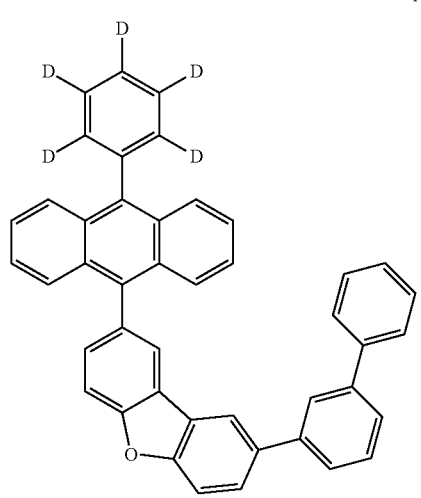
<Compound 151>
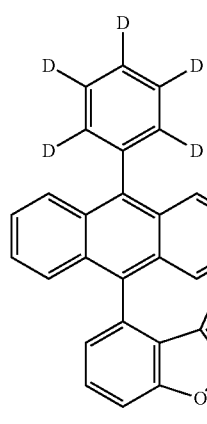
<Compound 149>
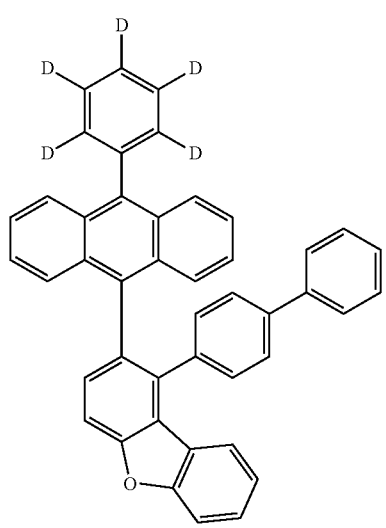
<Compound 152>
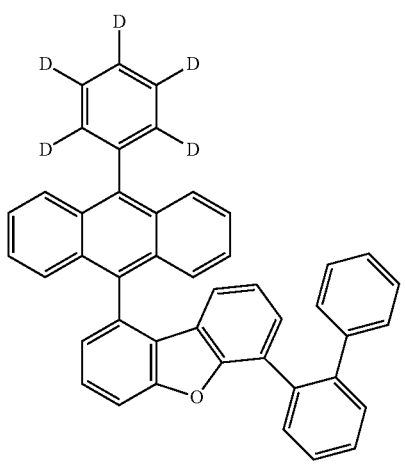

<Compound 153>
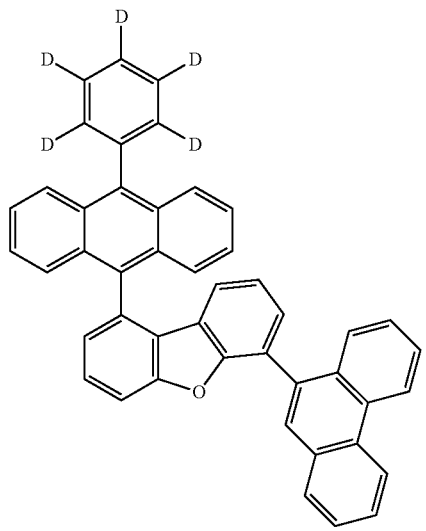
<Compound 154>
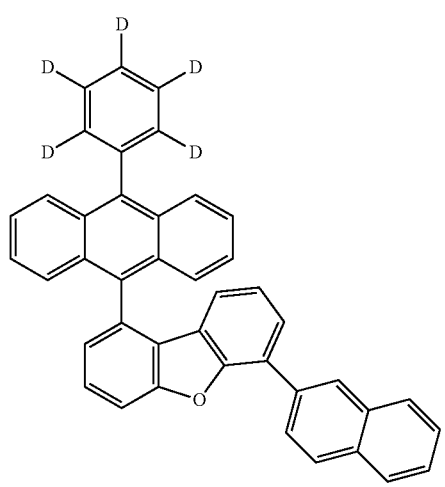
<Compound 155>
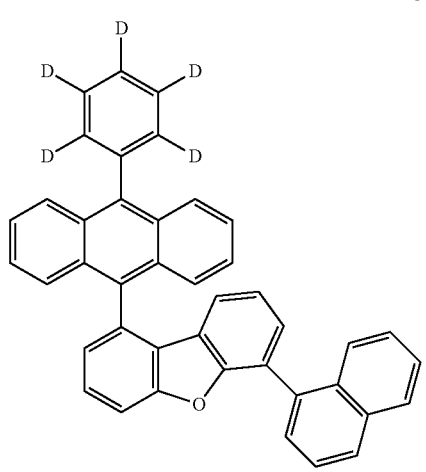
<Compound 156>
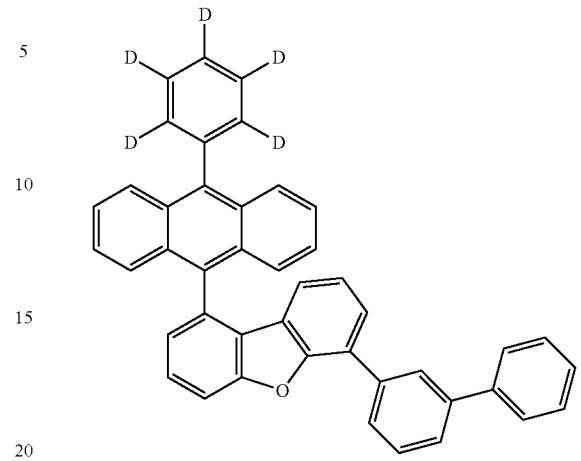
<Compound 157>
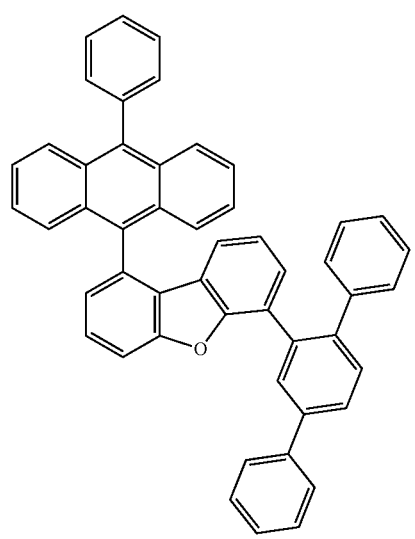
<Compound 158>
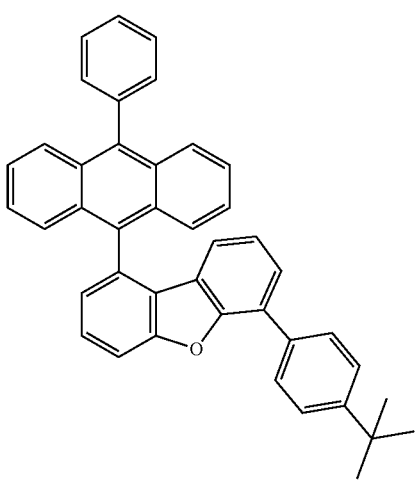

<Compound 159>
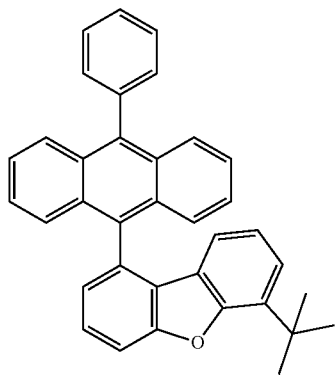
<Compound 160>
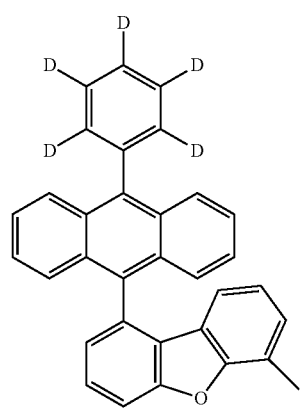
<Compound 161>
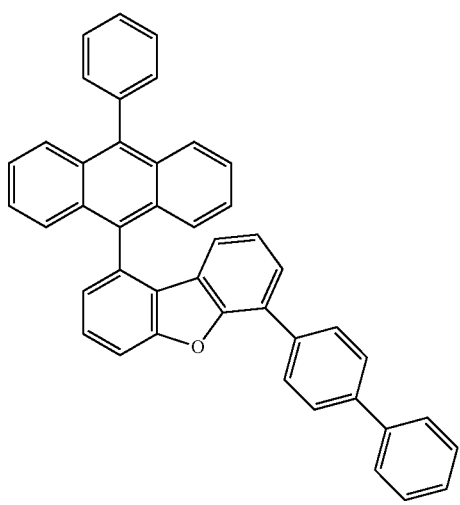
<Compound 162>
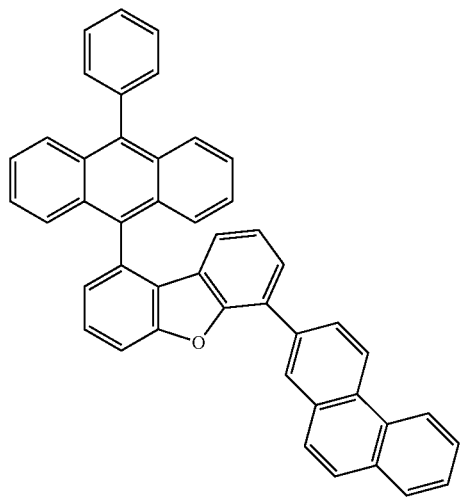
<Compound 163>
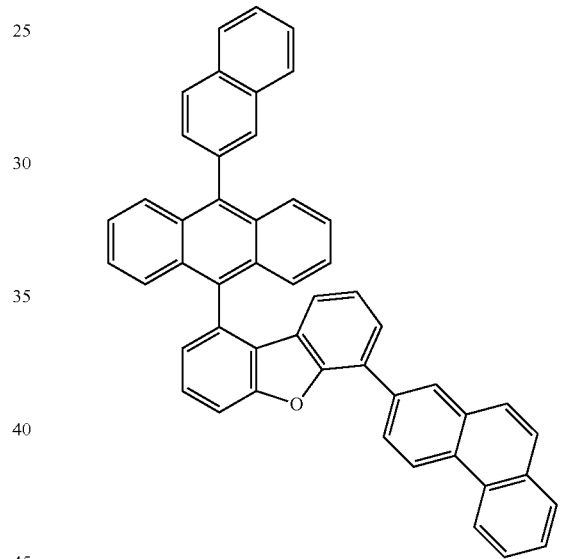
<Compound 164>
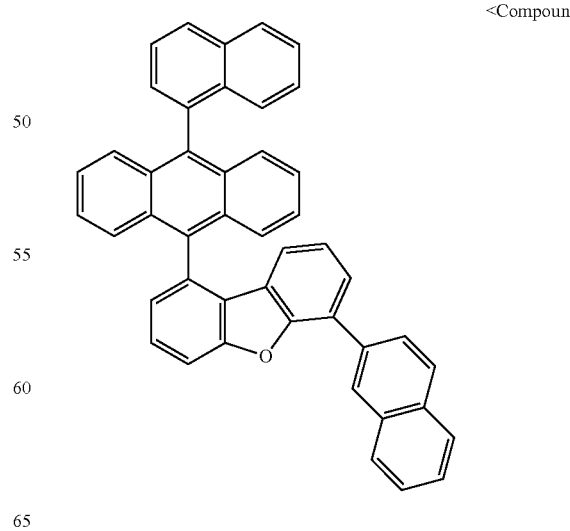

<Compound 165>
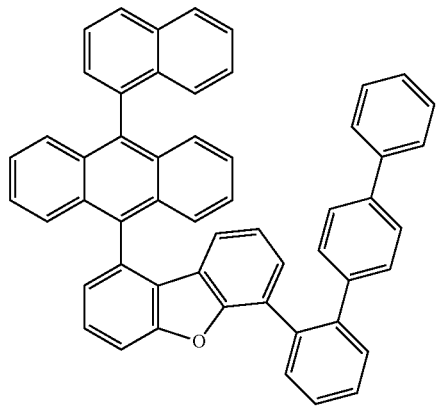
<Compound 166>
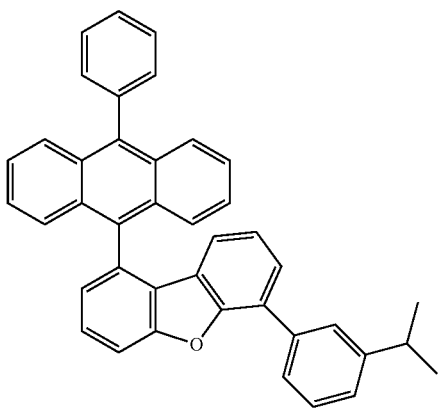
<Compound 167>
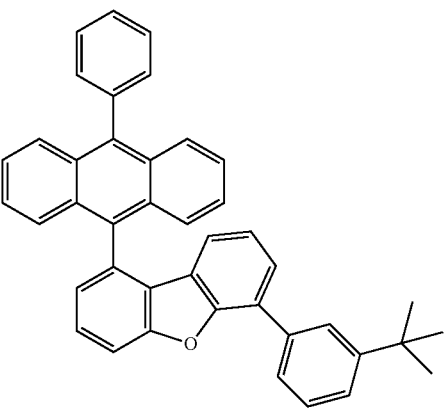
<Compound 168>
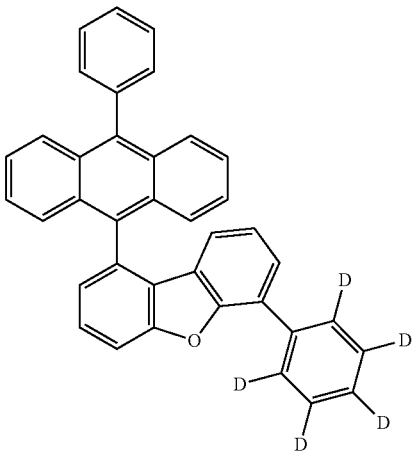
<Compound 169>
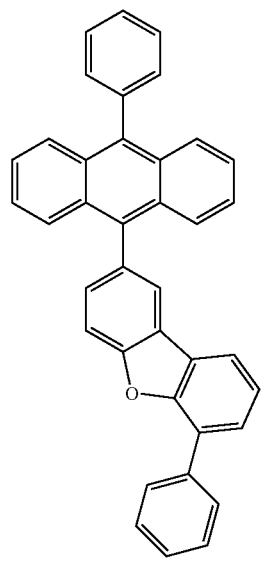
<Compound 170>
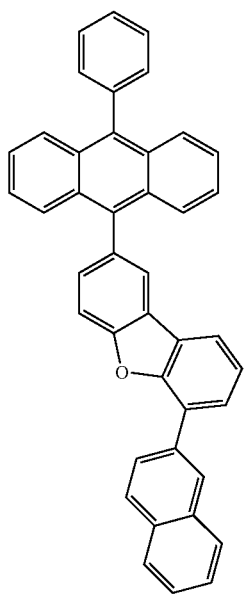

<Compound 171>
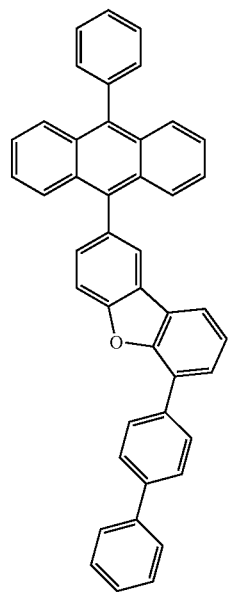
<Compound 173>
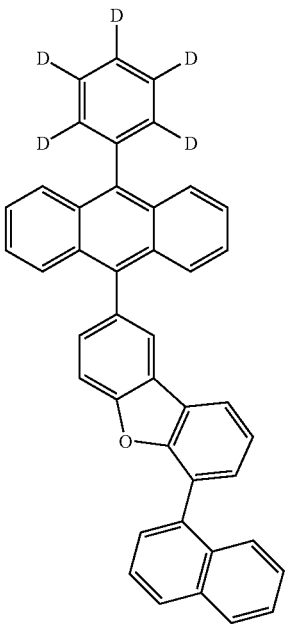
<Compound 172>
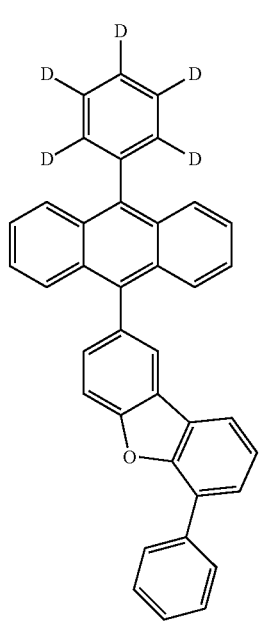
<Compound 174>
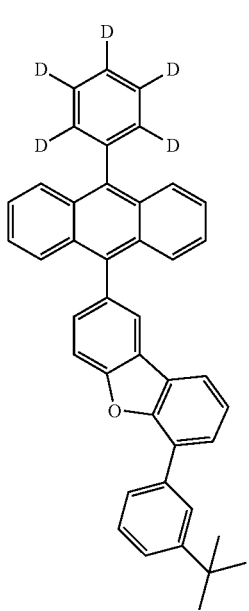

<Compound 175>
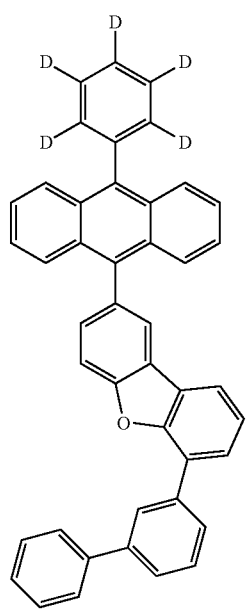
<Compound 176>
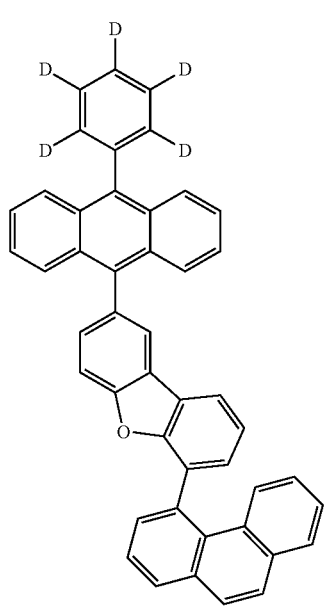
<Compound 177>
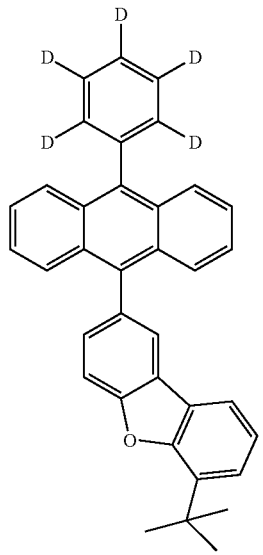
<Compound 178>
<Compound 179>
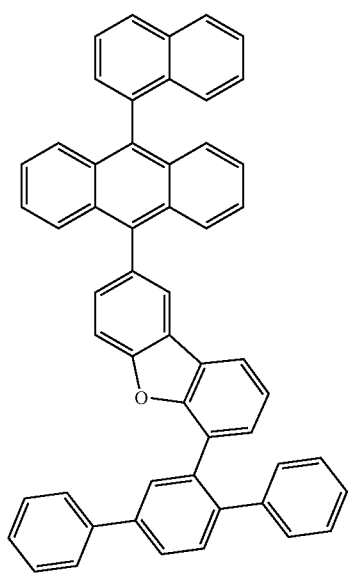

<Compound 180>

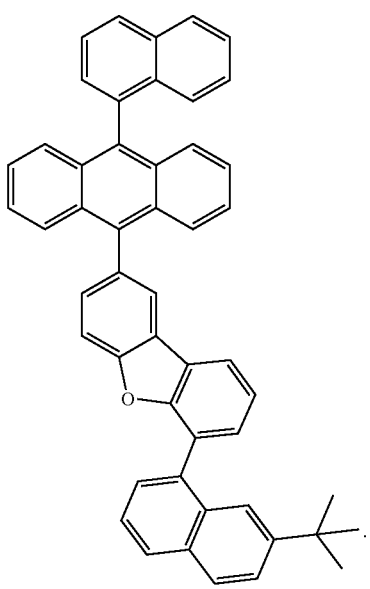

According to some particular embodiments of the present disclosure, the organic light-emitting diode may further comprise at least one of a hole injection layer, a hole transport layer, a functional layer capable of both hole injection and hole transport, an electron transport layer, and an electron injection layer in addition to the light-emitting layer.

In the organic light-emitting diode according to an embodiment of the present disclosure, the first electrode is an anode and the second electrode is a cathode, a hole transport layer and a hole injection layer are disposed between the anode and the light-emitting layer, and an electron transport layer and an electron injection layer are sequentially arranged between the light-emitting layer and the cathode. In this regard, the light-emitting layer may include at least one of the amine compounds represented by the following [Chemical Formula A] and at least one of the anthracene compounds represented by the following [Chemical Formula B] or [Chemical Formula C].

In the present disclosure, the phrase "(an organic layer) includes at least one organic compound"may be construed to mean that" (an organic layer) may include a single organic compound species or two or more difference species of organic compounds falling within the scope of the present disclosure".

Here, the light-emitting layer includes a host and a dopant, wherein compounds other than the anthracene compounds and amine compounds according to the present disclosure may be additional used.

Further, the content of the dopant may range from about 0.01 to 20 parts by weight, based on 100 parts by weight of the host, but is not limited thereto.

Component elements in each layer of the organic light-emitting diode according to the present disclosure are elucidated in detail, below.

For use as a material in a hole transport layer, an electron donating molecule having a low ionization potential is suitable. Predominantly, diamine, triamine, or tetraamine derivatives having a triphenylamine skeleton are employed, as exemplified by N,N'-bis(3-methylphenyl)-N,N'-dipehenyl-[1,1-bisphenyl]-4,4'-diamine or N,N'-di(naphthalen-1-yl)-N,N'-diphenylbenzidine (a-NPD).

A hole injection layer (HIL) may be further deposited beneath the hole transport layer. No particular limitations are imparted to the hole injection layer material, as long as it is one that is typically used in the art. Examples include HATCN (hexaazatriphenylenehexacarbonitrile), CuPc(copperphthalocyanine), the starburst amines TCTA (4,4',4''-tri(N-carbazolyl)triphenyl-amine), and m-MTDATA (4,4',4''-tris-(3-methylphenylphenyl amino)triphenylamine), etc.

Meanwhile, the electron transport material functions to stably transport electrons injected from the electron injection electrode (cathode) and may be a material well known in the art. Examples of the well-known material include quinoline derivatives, particularly tris(8-quinolinolate)aluminum (Alq3), Liq, TAZ, BAlq, beryllium bis(benzoquinolin-10-oate) (Bebq2), Compound 201, Compound 202, BCP, and the oxadiazole derivatives PBD, BMD, and BND, but are not limited thereto.

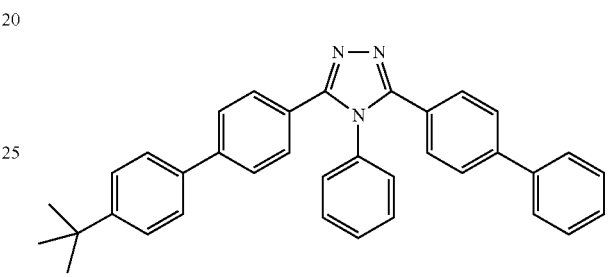

TAZ

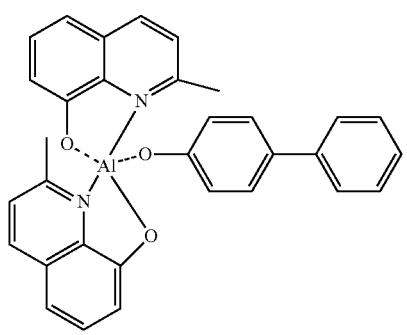

BAlq

<Compound 201>

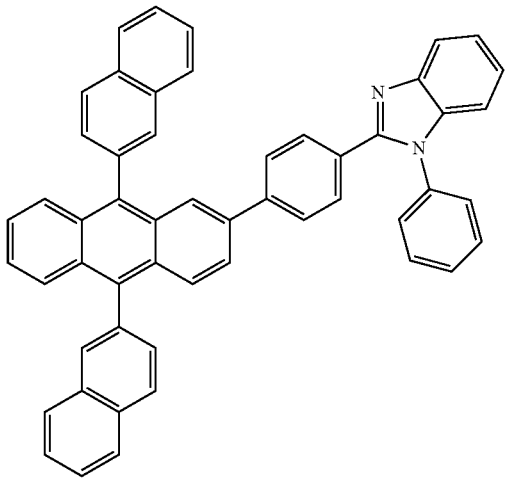

-continued

<Compound 202>

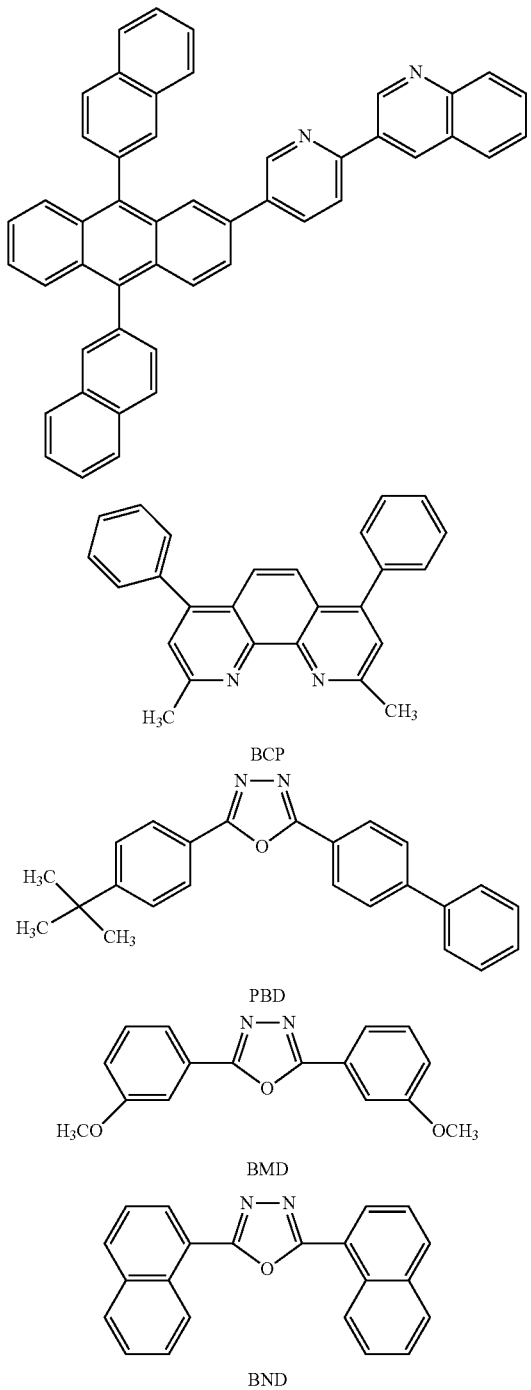

BCP

PBD

BMD

BND

In addition, the organic metal compound represented by Chemical Formula F may be used, either alone or in combination with the aforementioned material, as a compound for an electron transport layer in the present disclosure:

[Chemical Formula F]

$Y_m\text{—}M\text{—}(OA)_n$ wherein,

Y is a ligand that contains two moieties respectively responsible for forming a single bond through a direct bond to M and for forming a coordinate bond with M, each moiety being selected from among C, N, O, and S and which is chelated by the single bond and the coordinate bond; M is an alkali metal, an alkaline earth metal, an aluminum (Al) atom, or a boron (B) atom, and OA is a monodentate ligand capable of forming a single bond or a coordinate bond with M, wherein, O is oxygen, A is any one selected from among a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms bearing as a heteroatom at least one selected from among O, N, and S, and when M is an alkali metal, m=1 and n=0, when M is an alkaline earth metal, m=1 and n=1, or m=2 and n=0, or, when M is boron or aluminum, m is an integer of 1 to 3 and n is an integer of 0 to 2, satisfying the relationship m+n=3.

In the present disclosure, Y's, which are the same or different, are each independently selected from the following Structural Formulas C1 to C39, but are not limited thereto:

[Structural Formula C1]

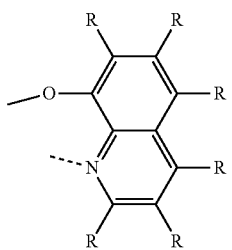

[Structural Formula C2]

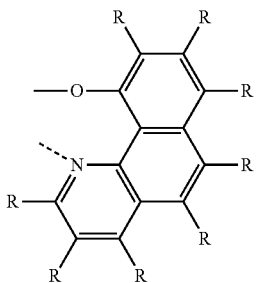

[Structural Formula C3]
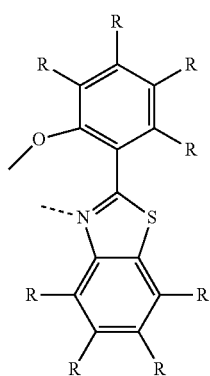
[Structural Formula C4]
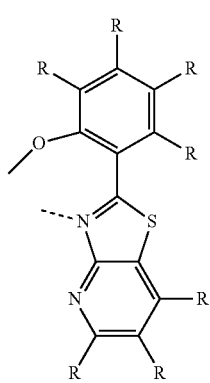
[Structural Formula C5]
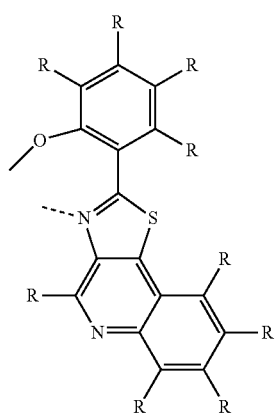
[Structural Formula C6]
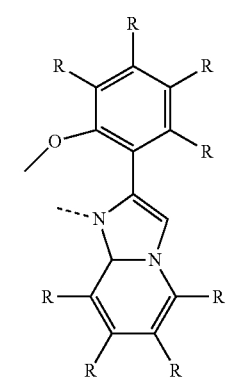
[Structural Formula C7]
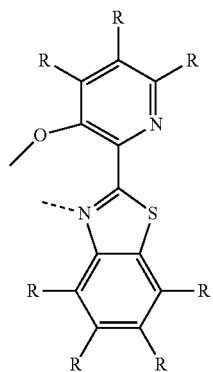
[Structural Formula C8]
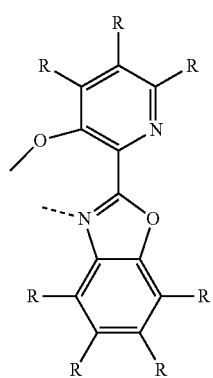
[Structural Formula C9]
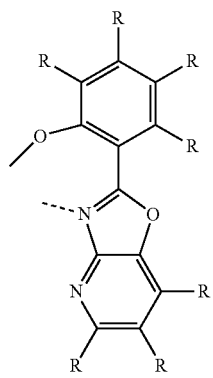
[Structural Formula C10]
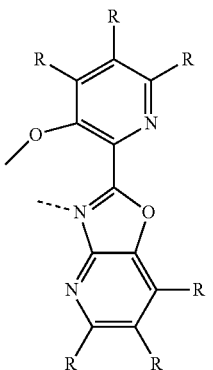

101
-continued
[Structural Formula C11]
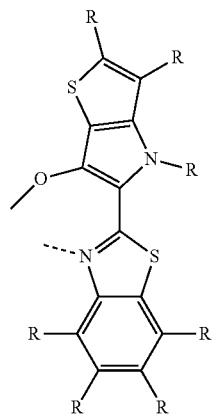
[Structural Formula C12]
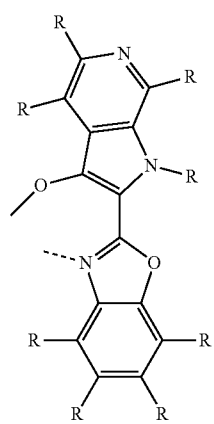
[Structural Formula C13]
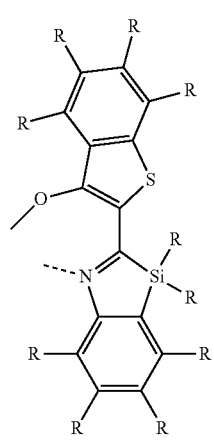
[Structural Formula C14]
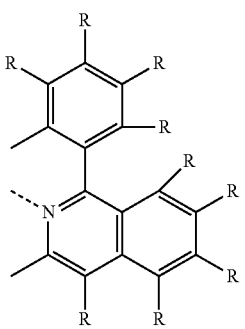
102
-continued
[Structural Formula C15]
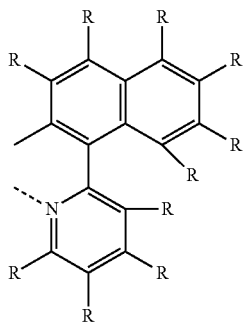
[Structural Formula C16]
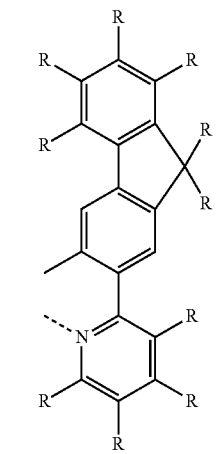
[Structural Formula C17]
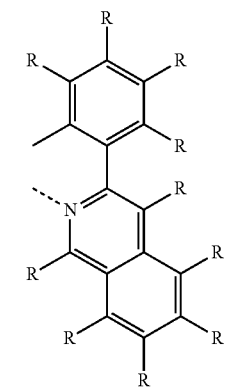
[Structural Formula C18]
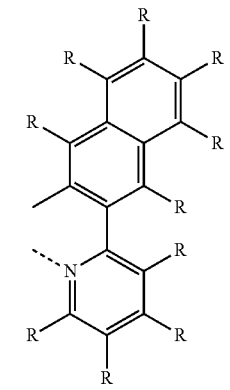

[Structural Formula C19]
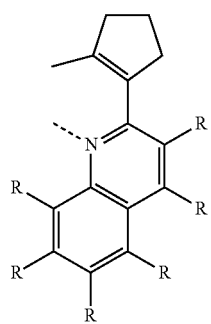
[Structural Formula C20]
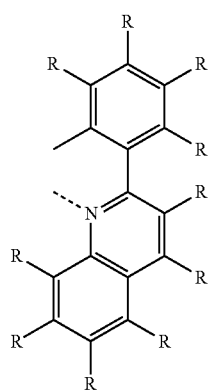
[Structural Formula C21]
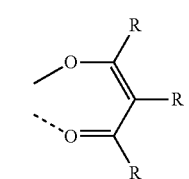
[Structural Formula C22]
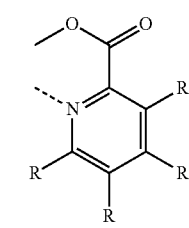
[Structural Formula C23]
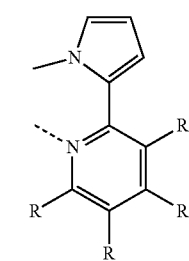
[Structural Formula C24]
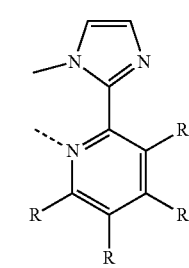
[Structural Formula C25]
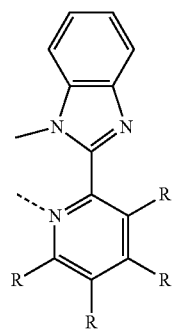
[Structural Formula C26]
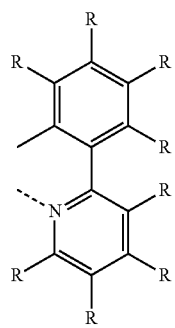
[Structural Formula C27]
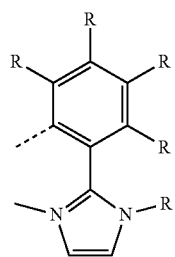
[Structural Formula C28]
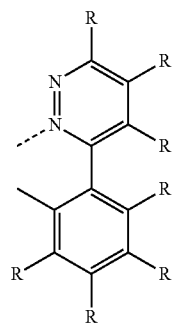
[Structural Formula C29]
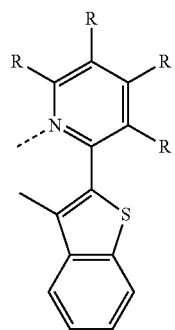

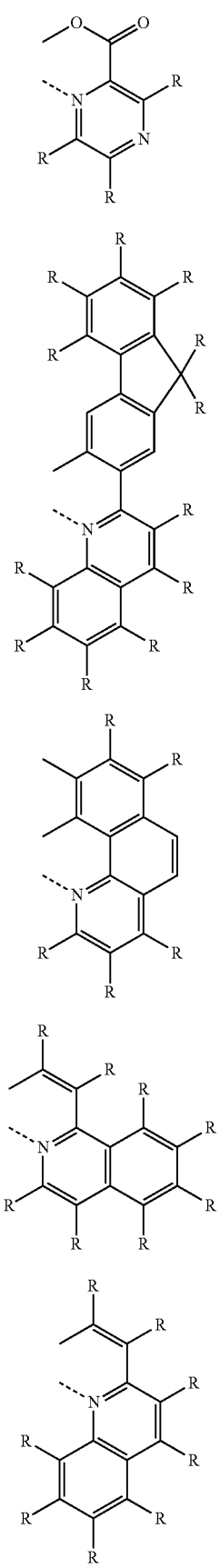

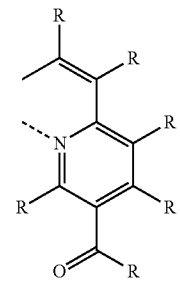

[Structural Formula C35]

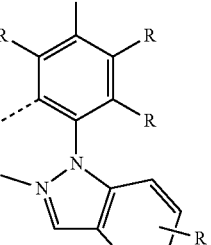

[Structural Formula C36]

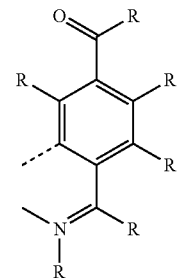

[Structural Formula C37]

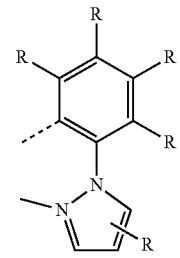

[Structural Formula C38]

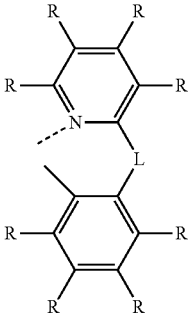

[Structural Formula C39]

wherein,
R's, which are the same or different, are each independently selected from among a hydrogen atom, a deuterium atom, a halogen, a cyano, a substituted or unsubstituted alkyl of 1 to 30 carbon atoms, a substituted or unsubstituted aryl of 6 to 30 carbon atoms, a substituted or unsubstituted heteroalkyl of 3 to 30 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 30 carbon atoms, and a substituted or unsubstituted arylsilyl of 6 to 30 carbon atoms, and may form a spiro or fused ring with an adjacent substituent via an alkylene or alkenylene linker. Here, the term "substituted" in the expression "substituted or unsubstituted" means having at least one substituent selected from the group consisting of a deuterium atom, a cyano, a halogen, a hydroxy, a nitro, an alkyl, an alkoxy, an alkylamino, an arylamino, a heteroarylamino, an alkylsilyl, an arylsilyl, an aryloxy, an aryl, a heteroaryl, a germanium, a phosphorus, and a boron.

An electron injection layer (EIL) that functions to facilitate electron injection from the cathode, thus improving the power efficiency of the diode, may be further deposited on the electron transport layer. So long as it is conventionally used in the art, any material can be available for the electron injection layer without particular limitations. Examples include LiF, NaCl, CsF, Li$_2$O, and BaO.

The electron injection layer may range in thickness from about 1 Å to about 100 Å and particularly from about 3 Å to about 90 Å. Given the thickness range for the electron injection layer, the diode can exhibit satisfactory electron injection properties without actually elevating a driving voltage.

The cathode may be made of a metal or metal alloy such as lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be employed to form a transparent cathode for a top-emitting organic light-emitting diode.

Further, one or more layers selected from among a hole injection layer, a hole transport layer, a functional layer capable of both hole injection and hole transport, a light-emitting layer, an electron transport layer, and an electron injection layer may be deposited using a deposition process or a solution process.

Here, the deposition process refers to a process by which a material is vaporized by heating in a vacuum or at a low pressure and deposited to form a thin film, and the solution process means a method in which a material for forming a layer is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices; flexible display devices; monochrome or white flat illumination devices; and monochrome or white flexible illumination devices.

The organic light-emitting diode of the present disclosure is explained below with reference to FIG. 1.

FIG. 1 is a schematic cross-sectional view of the structure of an organic light-emitting diode according to some embodiments of the present disclosure. The organic light-emitting diode comprises an anode 20, a hole transport layer 40, an organic light-emitting layer 50, an electron transport layer 60, and a cathode 80, and optionally a hole injection layer 30 and an electron injection layer 70. In addition, one or two intermediate layers may be further formed in the organic light-emitting diode, or a hole barrier layer or an electron barrier layer may also be employed.

Reference is made to FIG. 1 with regard to the organic light-emitting device and the fabrication method therefore according to the present disclosure. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide (SnO$_2$), or zinc oxide (ZnO), which are transparent and superior in terms of conductivity, may be used.

A hole injection layer material is applied on the anode electrode 20 by thermal deposition in a vacuum or by spin coating to form a hole injection layer 30. Subsequently, vacuum thermal deposition or spin coating may also be conducted to form a hole transport layer 40 with a hole transport layer material on the hole injection layer 30.

Then, an organic light-emitting layer 50 is deposited on the hole transport layer 40, optionally by followed by the formation of a hole barrier layer (not shown) on the organic light-emitting layer 50 by deposition in a vacuum or by spin coating. When holes traverse the organic light-emitting layer and are introduced into the cathode, the efficiency and lifespan of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound may be used for the hole barrier layer without limitation. Representative among hole barrier materials are BAlq, BCP, TPBI.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

A better understanding of the present disclosure may be obtained through the following examples which are set forth to illustrate, but are not to be construed as limiting, the present disclosure.

Synthesis Example 1: Synthesis of Compound of [Chemical Formula 3]

Synthesis Example 1-1. Synthesis of Compound of [Chemical Formula 3]

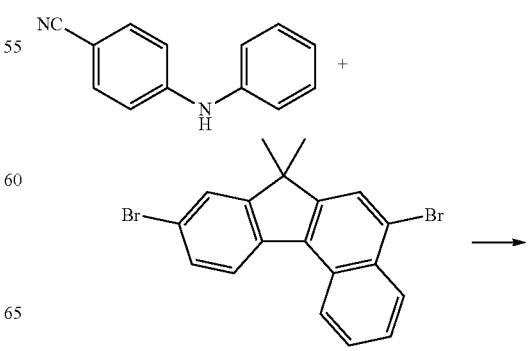

-continued

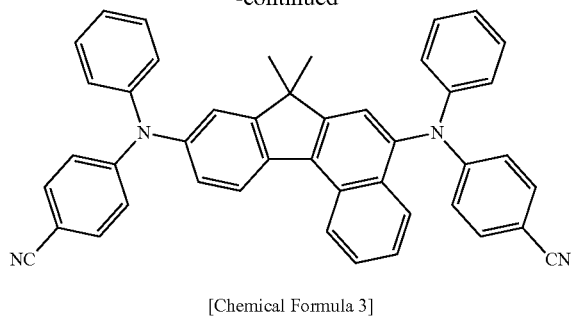

[Chemical Formula 3]

In a round-bottom flask, 5,9-dibromo-7,7-dimethyl-7H-benzofluorene (10.7 g, 26.7 mmol), 4-(phenylamino)benzonitrile (5.2 g, 26.7 mmol), BINAP (0.7 g, 1 mmol), bis(dibenzylideneacetone)dipalladium 0.4 g (0.7 mmol), sodium-tert-butoxide (6.5 g, 66.9 mmol), and toluene (100 ml) were stirred together for 12 hours under reflux in a nitrogen atmosphere. After completion of the reaction, layers were separated. The organic layer thus obtained was concentrated in a vacuum, followed by purification through column chromatography to afford the compound of [Chemical Formula 3] (12.9 g, yield 77%).

MS (MALDI-TOF): m/z 628.26 [M]$^+$

Synthesis Example 2: Synthesis of Compound of [Chemical Formula 5]

Synthesis Example 2-1. Synthesis of Compound of [Chemical Formula 5]

The same procedure as in Synthesis Example 1-1 was conducted, with the exception of using N-phenyl-4-(trimethylsilyl)benzenamine instead of 4-(phenylamino)benzonitrile, to afford the compound of [Chemical Formula 5]. (yield 80%)

MS (MALDI-TOF): m/z 722.35 [M]$^+$

Synthesis Example 3: Synthesis of Compound of [Chemical Formula 13]

Synthesis Example 3-1. Synthesis of [Intermediate 3-a]

[Intermediate 3-a]

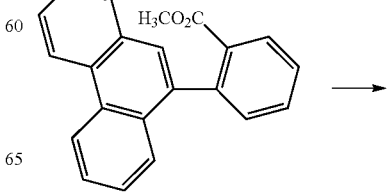

3-Bromodibenzofuran (24.7 g, 0.1 mol), 4-tert-butylaniline (14.9 g, 0.1 mol), palladium acetate (0.08 g, 0.32 mmol), 2,2'-bis(diphenylphosphino)-1-1'-binaphthyl (0.26 g, 0.42 mmol), and sodium-tert-butoxide (15.2 g, 0.16 mol) were added to toluene (200 mL) and stirred for 12 hours under reflux. Subsequent to cooling to room temperature, washing with methanol and recrystallization in dichloromethane and methanol afforded [Intermediate 3-a] (25.2 g, yield 80%).

Synthesis Example 3-2. Synthesis of Compound of [Chemical Formula 13]

The same procedure as in Synthesis Example 1-1 was conducted, with the exception of using 5,9-dibromo-7,7-diphenyl-7H-benzofluorene and [Intermediate 3-a] instead of 5,9-dibromo-7,7-dimethyl-7H-benzofluorene and 4-(phenylamino)benzonitrile, respectively, to afford the compound of [Chemical Formula 13]. (Yield 80%) MS (MALDI-TOF): m/z 994.45 [M]$^+$ Synthesis Example 4: Synthesis of Compound of [Chemical Formula 26]

Synthesis Example 4-1. Synthesis of [Intermediate 4-a]

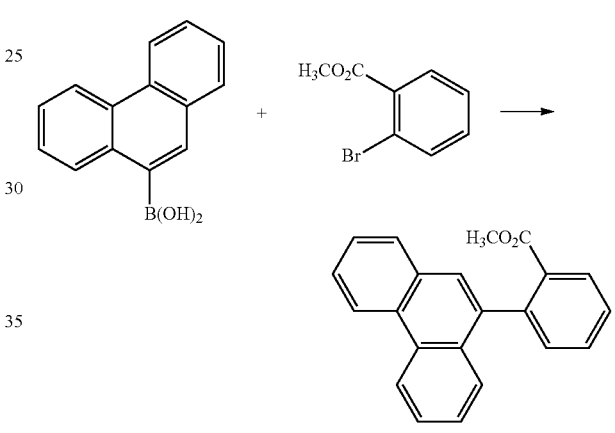

[Intermediate 4-a]

In a round-bottom flask, methyl2-bromobenzoate (24 g, 112 mmol), 9-phenanthrene boronic acid (34.7 g, 0.156 mmol), tetrakistriphenylphosphinepalladium (2.6 g, 2 mmol), potassium carbonate (30.9 g, 223 mmol), water (50 mL), toluene (125 mL), and tetrahydrofuran (125 mL) were stirred together for 12 hours under reflux. After completion of the reaction, the reaction mixture was subjected to layer separation and the organic layer thus formed was isolated by column chromatography to afford [Intermediate 4-a] (25 g, yield 72%).

Synthesis Example 4-2. Synthesis of [Intermediate 4-b]

-continued

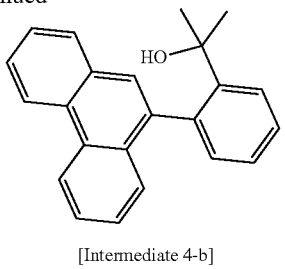

[Intermediate 4-b]

In a round-bottom flask, tetrahydrofuran (250 ml) was mixed with [Intermediate 4-a] (25 g, 80 mmol) and the mixture was cooled to −78° C. After 30 min, drops of 1.0 M methyl magnesium bromide (210 ml, 240 mmol) was slowly added over 1 hour, followed by elevation to room temperature. At room temperature, stirring for 2 hours was conducted before dropwise addition of an aqueous ammonium chloride solution. Extraction, vacuum distillation, and recrystallization in hexane in sequence afforded [Intermediate 4-b] (27 g, yield 82%).

Synthesis Example 4-3: Synthesis of [Intermediate 4-c]

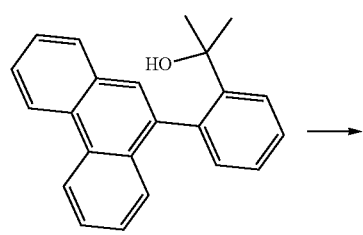

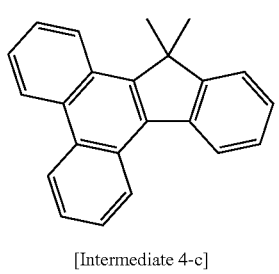

[Intermediate 4-c]

In a round-bottom flask, acetic acid (290 ml) was mixed with [Intermediate 4-b] (29 g, 66 mmol). After temperature elevation to 80° C., one or two drops of an aqueous hydrochloride solution were added to the reaction solution. The resulting solution was stirred for 2 hours under reflux and cooled to room temperature, after which the solid thus formed was filtered to obtain [Intermediate 4-c] 26 g (yield 93%).

Synthesis Example 4-4. Synthesis of [Intermediate 4-d]

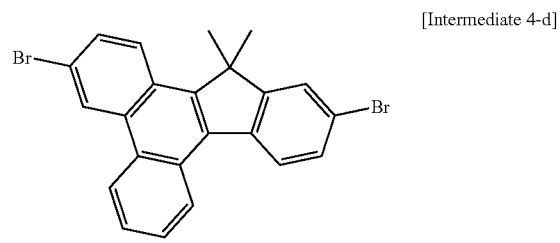 [SMILES: CC1(C)c2cc(Br)ccc2-c2c1c1ccc(Br)cc1c1ccccc21]

[Intermediate 4-d]

[Intermediate 4-c] (16.2 g, 0.055 mol) in dimethylformamide (250 mL) was stirred at 0° C. A solution of N-bromosuccinimide (21.5 g, 0.121 mol) in dimethylformamide (70 mL) was dropwise added and stirred for 6 hours. The reaction mixture was filtered with distilled water and washed with hexane. Dissolution in dichloromethane was followed by treatment with acid clay and active carbon. Washing with dichloromethane and recrystallization in hexane afforded [Intermediate 4-d] (19.1 g, yield 77%)

Synthesis Example 4-5. Synthesis of Compound of [Chemical Formula 26]

The same procedure as in Synthesis Example 1-1 was conducted, with the exception of using [Intermediate 4-d] and N-phenyl-1-naphthylamine instead of 5,9-dibromo-7,7-dimethyl-7H-benzofluorene and 4-(phenylamino)benzonitrile, respectively, to afford the compound of [Chemical Formula 26]. (yield 70%)

MS (MALDI-TOF): m/z 728.32 [M]+

Synthesis Example 5: Synthesis of Compound of [Chemical Formula 30]

Synthesis Example 5-1. Synthesis of [Intermediate 5-a]

[Intermediate 5-a]

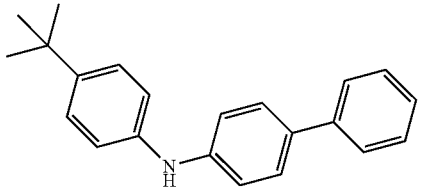

The same procedure as in Synthesis Example 3-1 was conducted, with the exception of using 4-bromobiphenyl instead of 3-bromodibenzofuran, to afford [Intermediate 5-a]. (yield 78%)

Synthesis Example 5-2. Synthesis of Compound of [Chemical Formula 30]

The same procedure as in Synthesis Example 1-1 was conducted, with the exception of using [Intermediate 4-d] and [Intermediate 5-a] instead of 5,9-dibromo-7,7-dimethyl-7H-benzofluorene and 4-(phenylamino)benzonitrile, respectively, to afford the compound of [Chemical Formula 30]. (yield 73%)

MS (MALDI-TOF): m/z 892.48 [M]+

113

Synthesis Example 6: Synthesis of Compound of [Chemical Formula 35]

Synthesis Example 6-1. Synthesis of [Intermediate 6-a]

The same procedure as in Synthesis Examples 4-2 to 4-4 was conducted, with the exception of using phenyl lithium instead of methyl magnesium bromide in Synthesis Example 4-2, to afford [Intermediate 6-a]. (yield 88%)

Synthesis Example 6-2. Synthesis of [Intermediate 6-b]

The same procedure as in Synthesis Example 3-1 was conducted, with the exception of using 1-bromo-4-(trimethylsilyl)benzene instead of 3-bromodibenzofuran, to afford [Intermediate 6-b]. (yield 77%)

Synthesis Example 6-3. Synthesis of Compound of [Chemical Formula 35]

The same procedure as in Synthesis Example 1-1 was conducted, with the exception of using [Intermediate 6-a] and [Intermediate 6-b] instead of 5,9-dibromo-7,7-dimethyl-7H-benzofluorene and 4-(phenylamino)benzonitrile, respectively, to afford the compound of [Chemical Formula 35]. (yield 67%)

MS (MALDI-TOF): m/z 1008.52 [M]$^+$

Synthesis Example 7: Synthesis of Compound of [Chemical Formula 45]

Synthesis Example 7-1. Synthesis of [Intermediate 7-a]

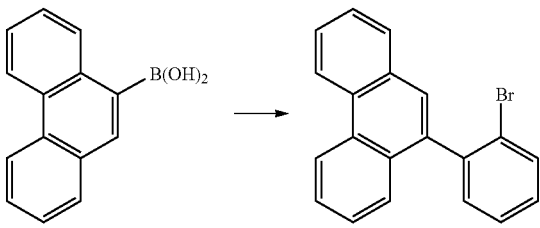 [SMILES: OB(O)c1cc2ccccc2c2ccccc12 ; Brc1ccccc1-c1cc2ccccc2c2ccccc12]

1-Bromo-2-iodobenzene (31.7 g, 112 mmol), 9-phenanthryl boronic acid (34.6 g, 156 mmol), tetrakis(triphenylphosphine)palladium (2.6 g, 2 mmol), potassium carbonate (30.9 g, 223 mmol), water (50 mL), toluene (125 mL), and tetrahydrofuran (125 mL) were stirred together for 12 hours under reflux. The organic layer thus formed was concentrated in a vacuum, followed by isolation through column chromatography to afford [Intermediate 7-a] (26.9 g, yield 72%).

114

Synthesis Example 7-2. Synthesis of [Intermediate 7-b]

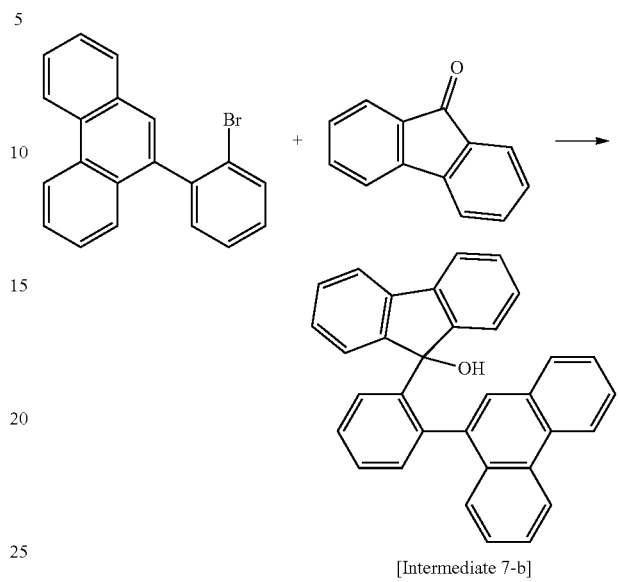

[Intermediate 7-b]

[Intermediate 7-a] (4.1 g, 12.2 mmol) in tetrahydrofuran (50 mL) was added with drops of n-butyl lithium (5.8 mL, 14.6 mmol) at −78° C. and then stirred for about 1 hour. A solution of 9-fluorenone (1.9 g, 10.8 mmol) in tetrahydrofuran (10 mL) was dropwise added slowly and then stirred for 2 hours at the same temperature and for 12 hours at room temperature. After extraction with ethyl acetate, recrystallization in diethylether afforded [Intermediate 7-b] (4.2 g, yield 79%).

Synthesis Example 7-3. Synthesis of [Intermediate 7-c]

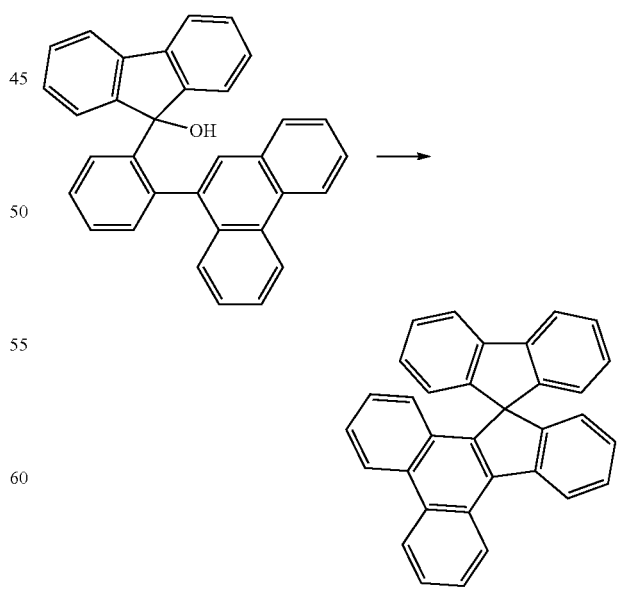

[Intermediate 7-c]

[Intermediate 7-b] (28.8 g, 66.3 mmol) was added to acetic acid (300 mL). After temperature elevation to 80° C., one or two drops of an aqueous hydrochloride solution were added to the reaction solution. The resulting solution was stirred for 2 hours under reflux and cooled to room temperature, followed by filtration to obtain [Intermediate 7-c] (25.4 g, yield 92%).

Synthesis Example 7-4. Synthesis of [Intermediate 7-d]

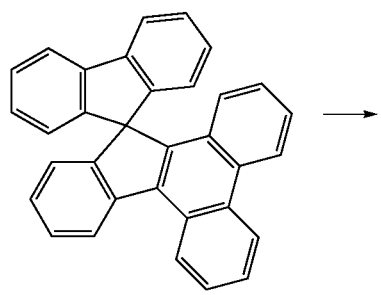

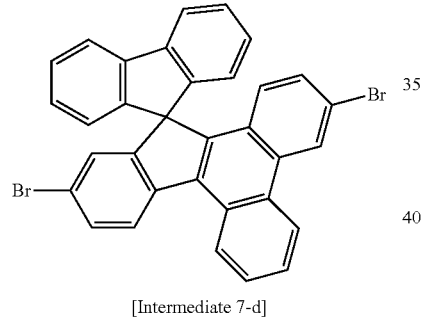

[Intermediate 7-d]

[Intermediate 7-c] (22.9 g, 0.055 mol) was added to dimethylformamide (250 mL) and stirred at 0° C. A solution of N-bromosuccinimide (21.5 g, 0.121 mol) in dimethylformamide (70 mL) was dropwise added and stirred for 12 hours. The reaction mixture was filtered with distilled water and washed with hexane. Dissolution in dichloromethane was followed by treatment with acid clay and active carbon. Washing with dichloromethane and recrystallization in hexane afforded [Intermediate 7-d] (23.7 g, yield 75%).

Synthesis Example 7-5. Synthesis of Compound of [Chemical Formula 45]

The same procedure as in Synthesis Example 1-1 was conducted, with the exception of using [Intermediate 7-d] and 3-methyldiphenylamine instead of 5,9-dibromo-7,7-dimethyl-7H-benzofluorene and 4-(phenylamino)benzonitrile, respectively, to afford the compound of [Chemical Formula 45]. (yield 70%)

MS (MALDI-TOF): m/z 778.33 [M]$^+$

Synthesis Example 8: Synthesis of [Compound 3]

Synthesis Example 8-1. Synthesis of [Intermediate 8-a]

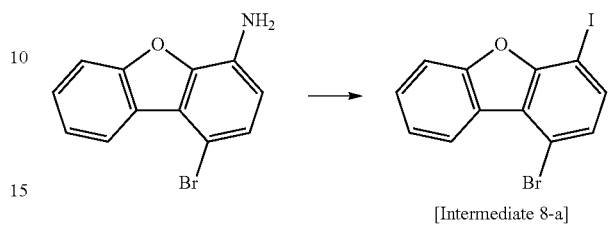

[Intermediate 8-a]

In a 2 L round-bottom flask, 1-bromo-4-aminodibenzofuran (73.0 g, 0.279 mol), HCl (90 ml), and water (440 ml) were stirred together at 0° C. A solution of sodium nitrite (25.0 g, 0.362 mol) in water (90 ml) was dropwise added to the reaction solution which was then stirred for 1 hour at the same temperature. A solution of potassium iodide (92.5 g, 0.557 mol) in water (90 ml) was dropwise added to the reaction solution and stirred at room temperature. After completion of the reaction, the organic layer was washed with an aqueous sodiumthiosulfate pentahydrate solution and concentrated in a vacuum. Isolation through column chromatography afforded [Intermediate 8-a] (52.3 g, yield 50%)

Synthesis Example 8-2. Synthesis of [Intermediate 8-b]

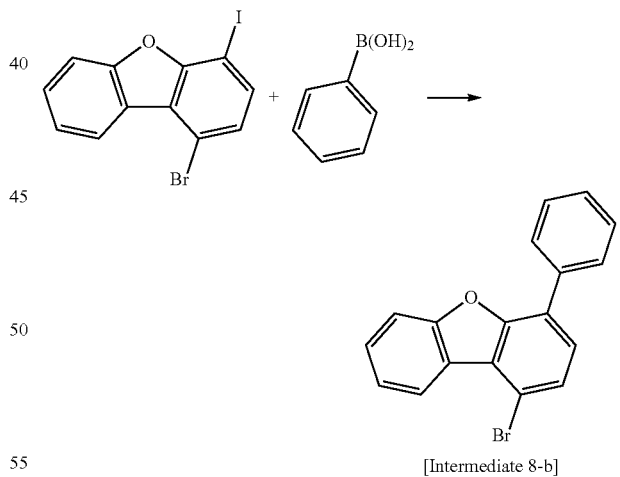

[Intermediate 8-b]

In a 2 L round-bottom flask, [Intermediate 8-a] (15.0 g, 40 mmol), phenyl boronic acid (5.4 g, 44 mmol), tetrakis (triphenylphosphine)palladium (0.9 g, 1 mmol), and potassium carbonate (11.1 g, 80 mmol) were put, followed by toluene (100 mL), methanol (45 mL), and water (30 mL). The solution was stirred overnight under reflux. After completion of the reaction, the reaction mixture was cooled to room temperature and concentrated in a vacuum. After isolation through column chromatography, recrystallization in heptane afforded [Intermediate 8-b] (7.0 g, yield 54%).

117

Synthesis Example 8-3. Synthesis of [Compound 3]

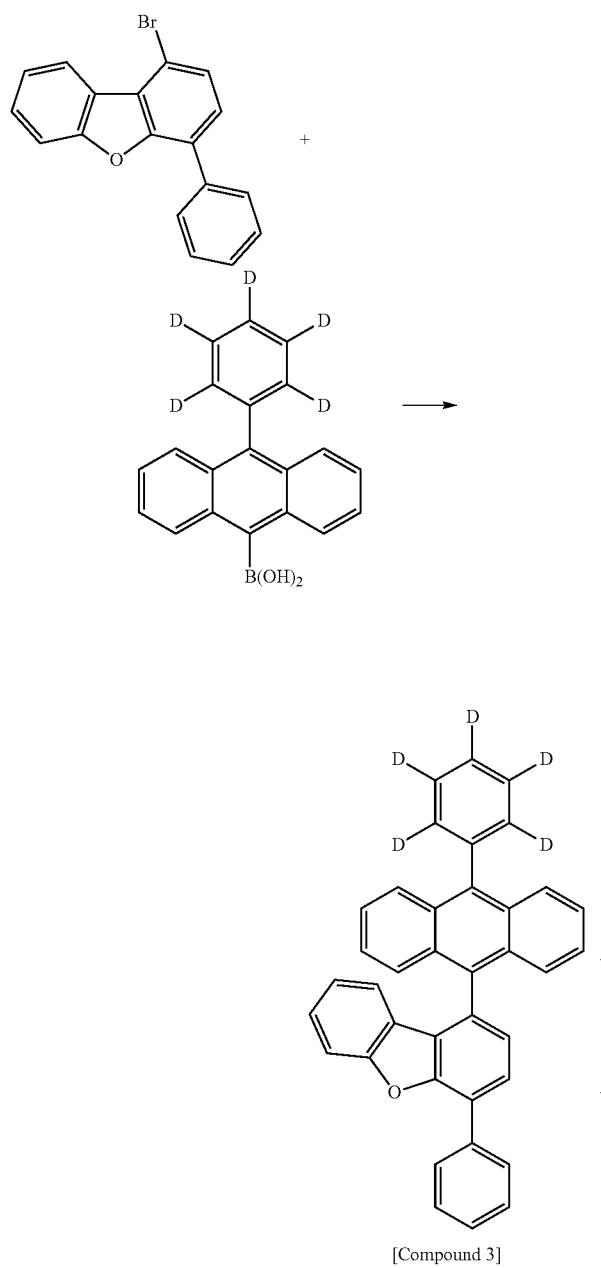

[Compound 3]

In a 250 mL round-bottom flask [Intermediate 8-b] (7.0 g, 22 mmol), (10-phenyl(d5)-anthracene-9-boronic acid (7.9 g, 26 mmol), tetrakis(triphenylphosphine)palladium (0.5 g, 1 mmol), and potassium carbonate (6.0 g, 43 mmol) were put, followed by toluene (50 mL), ethanol (21 mL), and water (14 mL). The solution was heated to 90° C. and stirred overnight. After completion of the reaction, the reaction mixture was cooled to room temperature, mixed with methanol (50 ml), and then stirred at room temperature. The solid thus formed was filtered and washed with methanol. Recrystallization of the solid in toluene and acetone afforded [Compound 3] (8.3 g, yield 75%)

MS (MALDI-TOF): m/z 501.21 [M+]

118

Synthesis Example 9: Synthesis of [Compound 7]

Synthesis Example 9-1. Synthesis of [Intermediate 9-a]

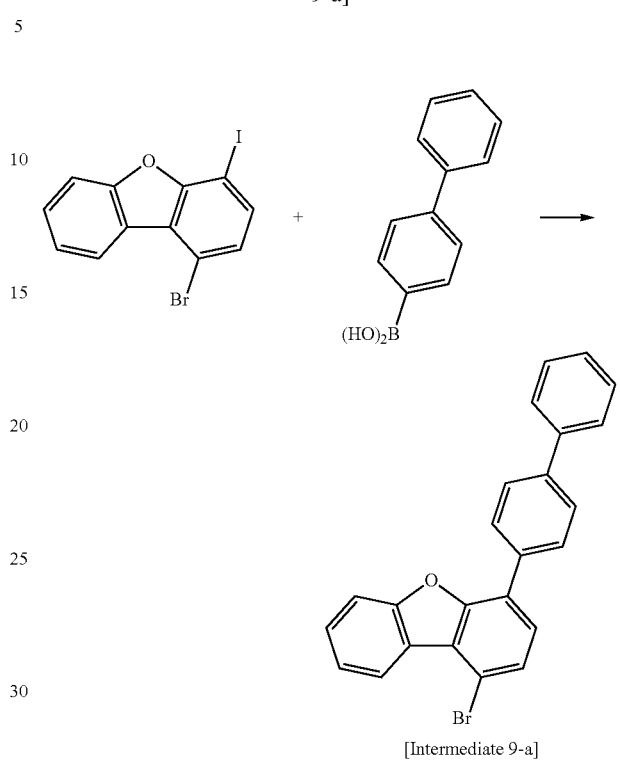

[Intermediate 9-a]

The same procedure as in Synthesis Example 8-2 was conducted, with the exception of using 4-biphenyl boronic acid instead of phenyl boronic acid, to afford [Intermediate 9-a]. (yield 56%)

Synthesis Example 9-2: Synthesis of [Compound 7]

The same procedure as in Synthesis Example 8-3 was conducted, with the exception of using [Intermediate 9-a] and 10-phenyl-anthracene-9-boronic acid instead of [Intermediate 8-b] and 10-phenyl(d5)-anthracene-9-boronic acid, respectively, to afford [Compound 7]. (yield 51%)

MS (MALDI-TOF): m/z 572.21 [M]$^+$

Synthesis Example 10: Synthesis of [Compound 56]

Synthesis Example 10-1. Synthesis of [Intermediate 10-a]

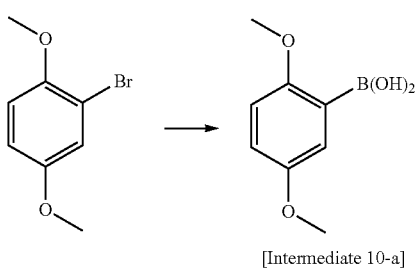

[Intermediate 10-a]

In a round-bottom flask, 2-bromo-1,4-dimethoxybenzene (50 g, 230 mmol) and tetrahydrofuran (400 ml) was added with drops of N-butyl lithium (167 ml, 280 mmol) at −78° C. under a nitrogen atmosphere and stirred for 2 hours. Trimethyl borate (36 ml, 320 mmol) was added before stirring overnight at room temperature. After completion of the reaction, drops of 2N—HCl were slowly added for acidification. Extraction, concentration in a vacuum, and recrystallization in heptane and toluene in the order afforded [Intermediate 10-a]. (20.8 g, 50%)

Synthesis Example 10-2. Synthesis of [Intermediate 10-b]

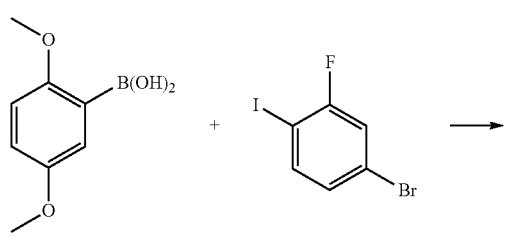

[Intermediate 10-b]

In a round-bottom flask, [Intermediate 10-a] (20.8 g, 110 mmol), 1-bromo 3-fluoro 4-iodobenzene (28.7 g, 95 mmol), tetrakis(triphenylphosphine)palladium (33 g, 29 mmol), and sodium carbonate (30.3 g, 290 mmol) were put, followed by toluene (200 ml), ethanol (60 ml), and water (60 ml). The solution was stirred for 12 hours under reflux. After completion of the reaction, the reaction mixture was cooled to room temperature, extracted, and concentrated in a vacuum. Isolation of the concentrate by column chromatography afforded [Intermediate 10-b]. (22.3 g, 63%)

Synthesis Example 10-3. Synthesis of [Intermediate 10-c]

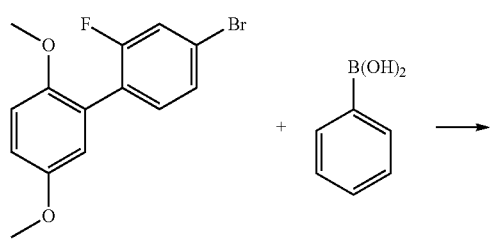

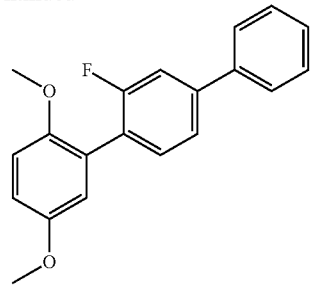

[Intermediate 10-c]

In a round-bottom flask [Intermediate 10-b] (22.3 g, 72 mmol), phenyl boronic acid (10.5 g, 86 mmol), tetrakis (triphenylphosphine)palladium (2.5 g, 2.2 mmol), potassium carbonate (29.7 g, 22 mmol), toluene (160 ml), ethanol (70 ml), and water (70 ml) were stirred together overnight under reflux. After completion of the reaction, the reaction mixture was cooled to room temperature and extracted. Recrystallization in heptane afforded [Intermediate 10-c]. (16.3 g, 74%)

Synthesis Example 10-4. Synthesis of [Intermediate 10-d]

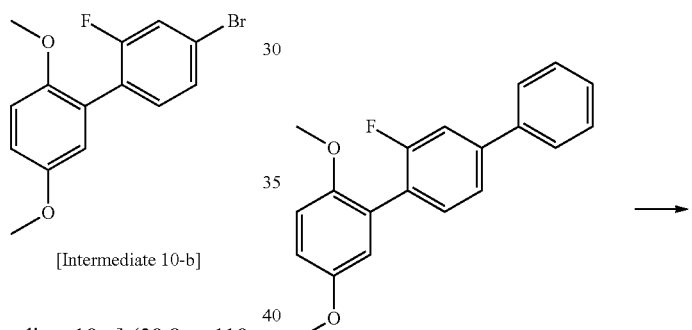

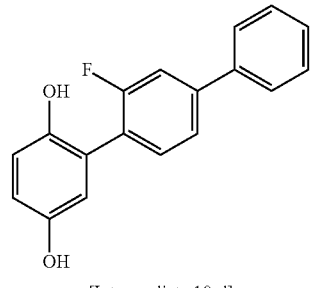

[Intermediate 10-d]

In a round-bottom flask [Intermediate 10-c] (16.3 g, 53 mmol), hydrobromic acid (48 ml, 260 mmol), and acetic acid (100 ml) were stirred together for 12 hours. After completion of the reaction, the reaction mixture was cooled to room temperature, added with water, and stirred.

After extraction, recrystallization in heptane afforded [Intermediate 10-d]. (14 g, 95%)

Synthesis Example 10-5. Synthesis of [Intermediate 10-e]

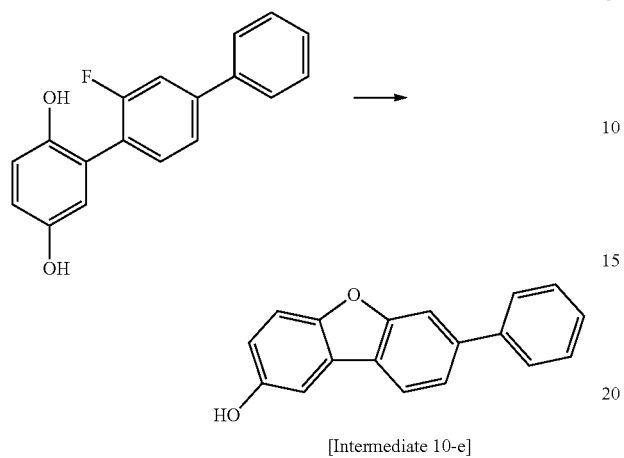

[Intermediate 10-e]

In a round-bottom flask, [Intermediate 10-d] (14 g, 50 mmol), potassium carbonate (20.7 g, 150 mmol), and N-methyl-2-pyrrolidone (112 ml) were stirred together for 12 hours. After completion of the reaction, recrystallization in heptane afforded [Intermediate 10-e]. (10.5 g, 81%)

Synthesis Example 10-6. Synthesis of [Intermediate 10-f]

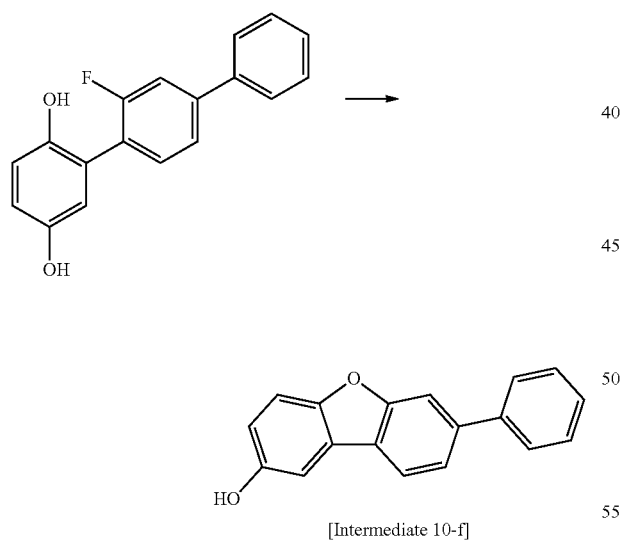

[Intermediate 10-f]

In a round-bottom flask, [Intermediate 10-e] (13.6 g, 52 mmol) was put under a nitrogen atmosphere, followed by adding dichloromethane (136 ml) to dissolve the intermediate. At 0° C., pyridine (10 ml, 110 mmol) and trifluoromethanesulfonyl anhydride (12.7 g, 68 mmol) were dropwise added. The solution was stirred at room temperature for 12 hours and then together with water (20 ml). After extraction, recrystallization in heptane afforded [Intermediate 10-f]. (7.5 g, 37%)

Synthesis Example 10-7. Synthesis of [Compound 56]

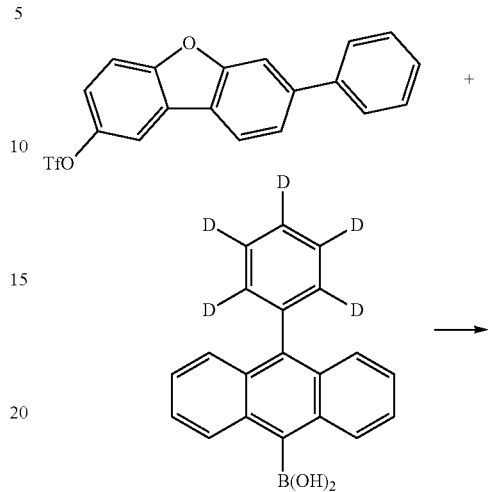

[Compound 56]

In a round-bottom flask, [Intermediate 10-f] (7.5 g, 19 mmol), 10-phenyl(d5)-anthracene-9-boronic acid (7 g, 23 mmol), tetrakis(triphenylphosphine)palladium (0.66 g, 0.6 mmol), and potassium carbonate (7.9 g, 57 mmol) were put, followed by toluene (53 ml), ethanol (23 ml), and water (23 ml). The solution was stirred for 12 hours under reflux. After completion of the reaction, the reaction mixture was cooled to room temperature and added with methanol before stirring. The organic layer thus formed was isolated, concentrated in a vacuum, and recrystallized in toluene and acetone to afford <Compound 56>. (6 g, 63%)

MS (MALDI-TOF): m/z 501.21 $[M]^+$

Synthesis Example 11: Synthesis of [Compound 115]

Synthesis Example 11-1. Synthesis of [Intermediate 11-a]

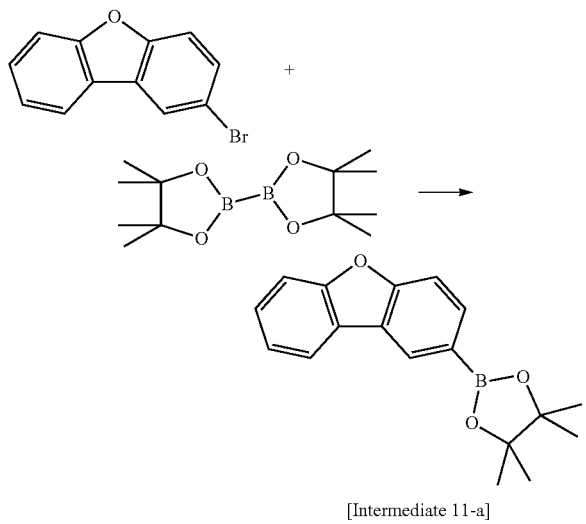

[Intermediate 11-a]

In a 2 L round-bottom flask, 2-bromodibenzofuran (70.0 g, 0.283 mol), bis(pinacolato)diboron (86.3 g, 0.340 mol), 1,1'-bis(diphenylphosphino)ferrocence-palladium (II)dichloride (4.6 g, 0.006 mol), potassium acetate (56.6 g, 0.567 mol), and 1,4-dioxane (700 ml) were stirred overnight under reflux. After completion of the reaction, the reaction mixture was filtered through a celite pad and concentrated in a vacuum. Isolation by column chromatography afforded <Intermediate 11-a> (66.4 g, yield 79%).

Synthesis Example 11-2. Synthesis of [Compound 115]

The same procedure as in Synthesis Example 8-3 was conducted, with the exception of using 9-bromo-10-(naphthalen-1-yl)anthracene and [Intermediate 11-a] instead of [Intermediate 8-b] and 10-phenyl(d5)-anthracene-9-boronic acid, respectively, to afford [Compound 115]. (yield 55%)

MS (MALDI-TOF): m/z 470.17 $[M]^+$

Synthesis Example 12: Synthesis of [Compound 151]

Synthesis Example 12-1: Synthesis of [Compound 151]

The same procedure as in Synthesis Examples 10-1 to 10-7 was conducted, with the exception of using 1-bromo-2,6-dimethoxybenzene and 1-bromo-2-fluoro-3-iodobenzene instead of 2-bromo-1,4-dimethoxy benzene in Synthesis Example 10-1 and 1-bromo-3-fluoro-4-iodobenzene in Synthesis Example 10-2, to afford [Compound 151]. (yield 63%)

MS (MALDI-TOF): m/z 501.21 $[M]^+$

Synthesis Example 13: Synthesis of [Compound 155]

Synthesis Example 13-1. Synthesis of [Compound 155]

The same procedure as in Synthesis Examples 10-1 to 10-7 were conducted, with the exception was conducted, with the exception of using 1-bromo-2,6-dimethoxybenzene, 1-bromo-2-fluoro-3-iodobenzene, and 1-naphthalene boronic acid instead of 2-bromo-1,4-dimethoxybenzene in Synthesis Example 10-1, 1-bromo-3-fluoro-4-iodobenzene in Synthesis Example 10-2, and phenylboronic acid in Synthesis Example 10-3, respectively, to afford [Compound 155]. (yield 55%)

MS (MALDI-TOF): m/z 551.23 $[M]^+$

Examples 1 To 7: Fabrication of Organic Light-Emitting Diode

An ITO glass substrate was patterned to have a translucent area of 2 mm×2 mm and then rinsed. The substrate was mounted in a vacuum chamber, which was then set to have a base pressure of $1 \times 10^{-6}$ torr. On the ITO glass substrate, films were formed of HATCN(50 Å) and NPD(650 Å) in the order. A light-emitting layer (200 Å) was formed of a mixture including the compounds shown in Table 1 as a host and a dopant (weight ratio 97:3). Then, [Chemical Formula E-1] and Liq was sequentially deposited to form an electron transport layer (300 Å) and an electron injection layer (10 Å), respectively, followed by formation of an Al layer (1,000 Å) to fabricate an organic light-emitting diode. The organic light-emitting diodes thus obtained were measured at 10 mA/cm² to determine the luminescence properties thereof.

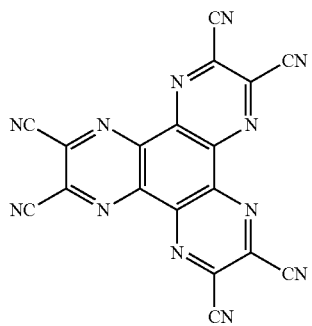

[HATCN]

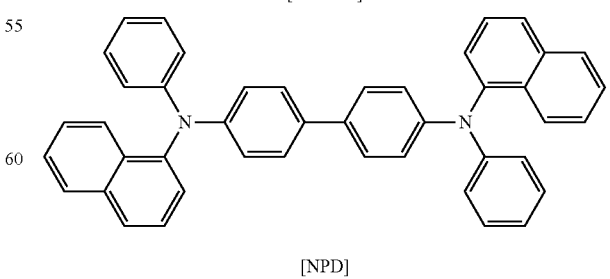

[NPD]

-continued

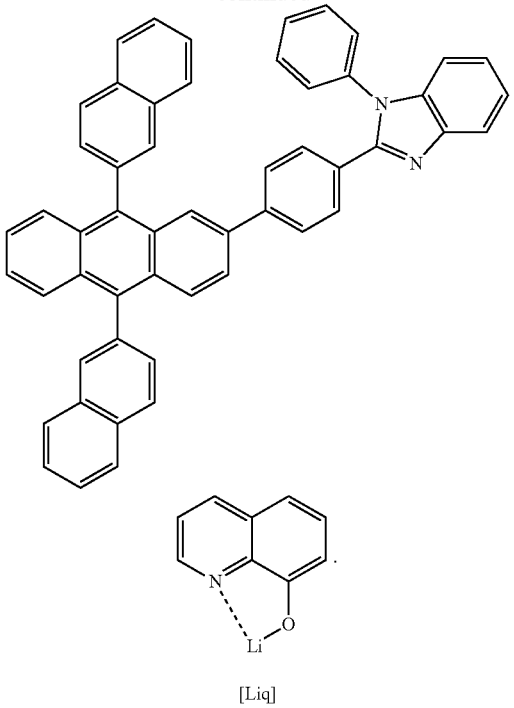

[Liq]

Comparative Examples 1 and 2

An organic light-emitting diode was fabricated in the same manner as in Examples 1 to 7, with the exception of using [BD1] as a dopant in the light-emitting layer. The organic light-emitting diode was measured at 10 mA/cm$^2$ to determine the luminescence properties thereof. The structure of [BD1] is as follows:

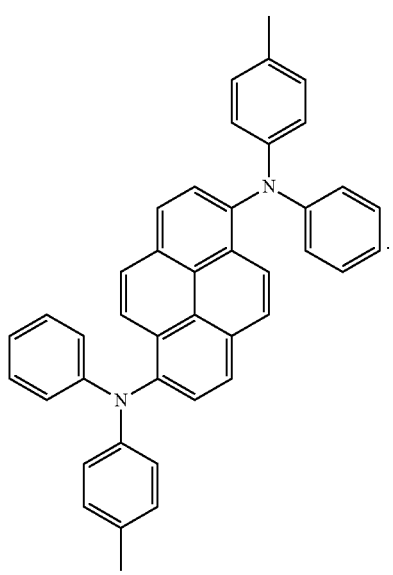

[BD1]

Comparative Examples 3 and 4

An organic light-emitting diode was fabricated in the same manner as in Examples 1 to 7, with the exception of using [BH1] as a host in the light-emitting layer. The organic light-emitting diode was measured at 10 mA/cm$^2$ to determine the luminescence properties thereof. The structure of [BH1] is as follows:

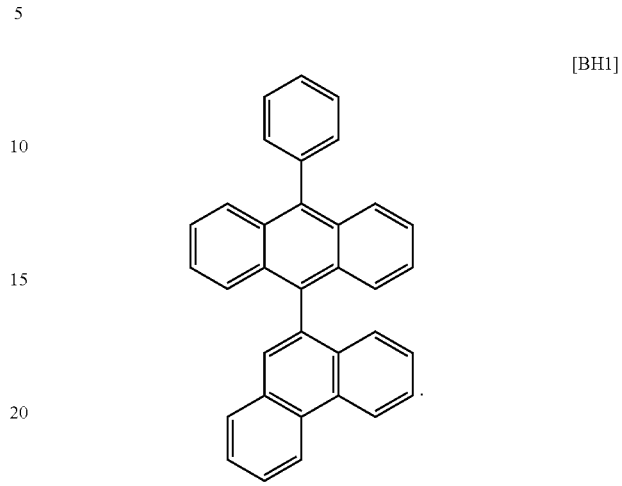

[BH1]

The OLEDs fabricated in Examples 1 to 7 and Comparative Examples 1 to 4 were measured for driving voltage, efficiency, and lifespan, and the results are summarized in Table 1, below.

In Table 1, T97 refers to the time taken for the initial luminance to decrease to 97% thereof.

TABLE 1

| Example No. | Host | Dopant | V | EQE | T97 |
|---|---|---|---|---|---|
| C. Ex. 1 | Compound 115 | BD1 | 4.1 | 8.2 | 54 |
| C. Ex. 2 | Compound 151 | BD1 | 4.1 | 8.2 | 52 |
| C. Ex. 3 | BH1 | Chemical Formula 3 | 4.3 | 7.8 | 42 |
| C. Example 4 | BH1 | Chemical Formula 35 | 4.2 | 7.7 | 40 |
| Ex. 1 | Compound 56 | Chemical Formula 3 | 3.7 | 9.8 | 98 |
| Ex. 2 | Compound 155 | Chemical Formula 5 | 3.8 | 9.8 | 85 |
| Ex. 3 | Compound 151 | Chemical Formula 13 | 3.7 | 9.8 | 88 |
| Ex. 4 | Compound 115 | Chemical Formula 26 | 3.7 | 9.7 | 94 |
| Ex. 5 | Compound 56 | Chemical Formula 30 | 3.7 | 10.0 | 86 |
| Ex. 6 | Compound 7 | Chemical Formula 35 | 3.7 | 9.8 | 90 |
| Ex. 7 | Compound 3 | Chemical Formula 45 | 3.8 | 9.6 | 85 |

As is understood from the data of Table 1, the OLEDs according to the present disclosure could exhibit longer lifespan and operate at lower voltage with high efficiency than conventional OLEDs of Comparative Examples 1 to 4, thereby demonstrating their high applicability to organic electroluminescence devices.

INDUSTRIAL APPLICABILITY

Introducing a dopant and a host of specific structures into the light-emitting layer thereof, the organic light-emitting diode according to the present disclosure exhibits long lifespan, low voltage, and high efficiency properties and thus is industrially applicable.

The invention claimed is:

1. An organic light-emitting diode, comprising: a first electrode; a second electrode facing the first electrode; and a light-emitting layer intercalated between the first electrode and the second electrode, wherein the light-emitting layer comprises at least one of the amine compounds represented by the following Chemical Formula A and at least one of the anthracene compounds represented by the following Chemical Formula B:

[Chemical Formula A]

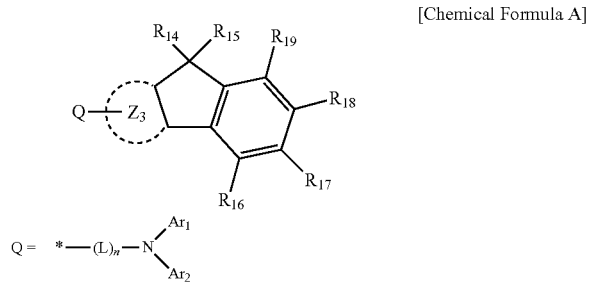

wherein, $Z_3$ is a substituted or unsubstituted aromatic hydrocarbon ring, selected from between Structural Formula 11 and Structural Formula 15:

[Structural Formula 11]

[Structural Formula 15]

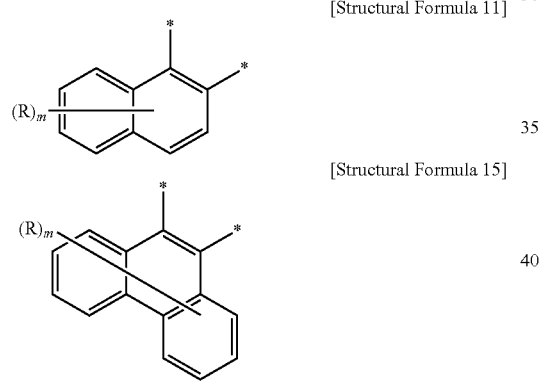

wherein

"-*" denotes a bonding site for forming a 5-membered ring containing the carbon atom connected to both $R_{14}$ and $R_{15}$, R's are as defined below for $R_{16}$ to $R_{19}$, and m is an integer of 1 to 8 wherein when m is 2 or more or when R is two or more, individual R's are same or different, the substituents $R_{14}$ and $R_{15}$, which are the same or different, are each independently one selected from among a substituted or unsubstituted alkyl of 1 to 30 carbon atoms, and a substituted or unsubstituted aryl of 6 to 50 carbon atoms, $R_{16}$ to $R_{19}$, which are the same or different, are each independently one selected from among a hydrogen atom, a deuterium atom, with a proviso that one of the substituents $R_{16}$ to $R_{19}$ represents a single bond attached to the linker L in a Q moiety, two adjacent carbon atoms within $Z_3$ form a five-membered ring with the carbon atom having both the substituents $R_{14}$ and $R_{15}$ thereon, thus establishing a fused ring, a carbon atom of the aromatic ring of $Z_3$ which does not participate in forming the five-membered ring is bonded to the linker L in a Q moiety, the linker L represents a single bond, n is an integer of 1, the respective moieties Q's which are bonded to $Z_3$ and to one of $R_{16}$ to $R_{19}$ are same or different, the substituents $Ar_1$ and $Ar_2$, which are same or different, are each independently one selected from among a substituted or unsubstituted aryl of 6 to 40 carbon atoms and a substituted or unsubstituted heteroaryl of 2 to 30 carbon atoms;

[Chemical Formula B]

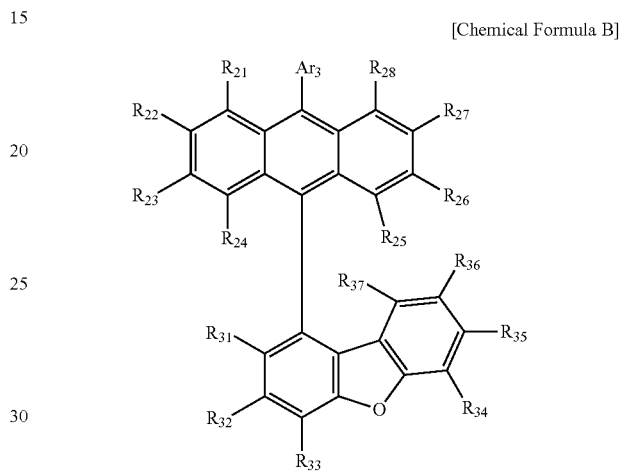

wherein, $R_{21}$ to $R_{28}$, which are same or different, are each independently one selected from among a hydrogen atom, and a deuterium atom, $R_{31}$ to $R_{37}$, which are same or different, are each independently one selected from among a hydrogen atom, a deuterium atom, a substituted or unsubstituted aryl of 6 to 50 carbon atoms, and the substituent $Ar_3$ is a deuterium substituted or unsubstituted naphthyl or a substituent represented by the following Structural Formula C:

[Structural Formula C]

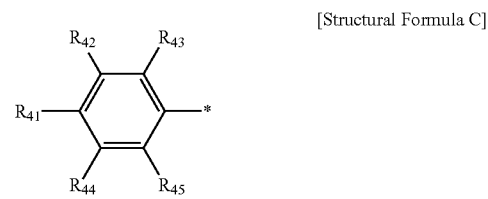

wherein $R_{41}$ to $R_{45}$ are same or different and are a hydrogen atom, a deuterium atom, or a deuterium substituted or unsubstituted aryl of 6 to 50 carbon atoms, or a deuterium substituted or unsubstituted alkyl of 1 to 30 carbon atoms, wherein the term 'substituted' in the expression 'substituted or unsubstituted' means having at least one substituent selected from the group consisting of a deuterium, a halogen, an alkyl of 1 to 24 carbon atoms, a halogenated alkyl of 1 to 24 carbon atoms, an aryl of 6 to 24 carbon atoms and an alkylsilyl of 1 to 24 carbon atoms.

2. The organic light-emitting diode of claim 1, wherein the light emitting-layer comprises a host and a dopant,
  wherein the anthracene compound represented by Chemical Formula B is used as the host and the amine compound represented by Chemical Formula A is used as the dopant.

3. The organic light-emitting diode of claim 1, wherein $R_{14}$ and $R_{15}$ are same or different and are each independently a substituted or unsubstituted aryl of 6 to 30 carbon atoms.

4. The organic light-emitting diode of claim 1, wherein $Ar_1$ and $Ar_2$ are same or different and are each independently a substituted or unsubstituted aryl of 6 to 30 carbon atoms.

5. The organic light-emitting diode of claim 1, wherein the anthracene compound represented by Chemical Formula B is one selected from among the following Compounds:

<Compound 1>

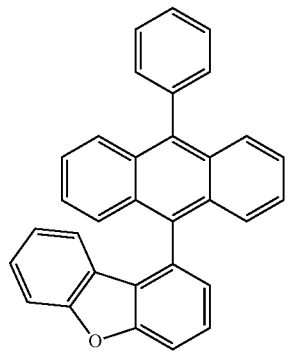

<Compound 2>

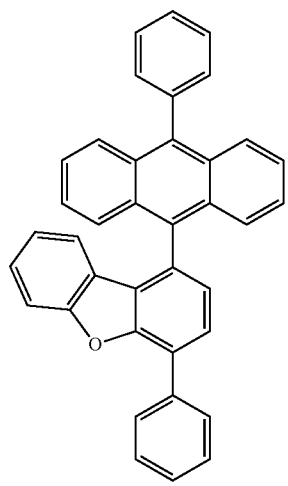

<Compound 3>

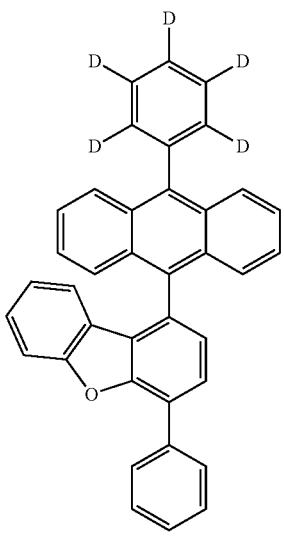

<Compound 4>

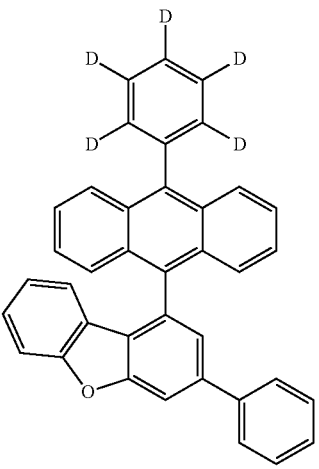

<Compound 5>

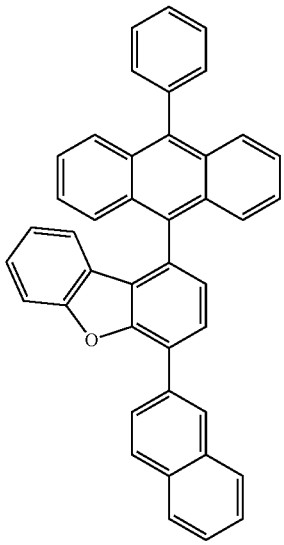

<Compound 7>
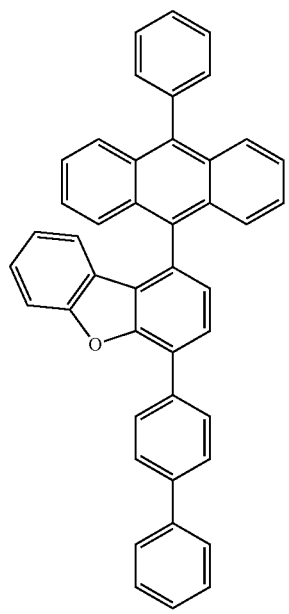
<Compound 10>
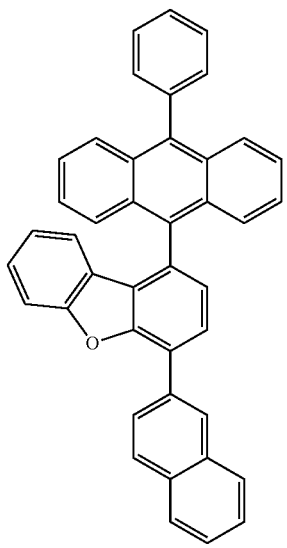
<Compound 42>
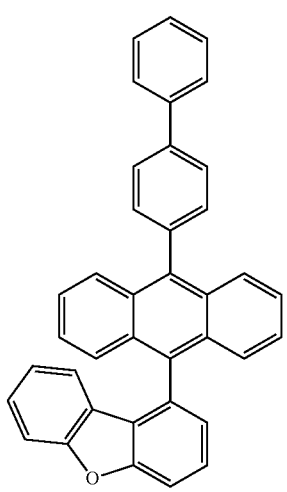
<Compound 8>
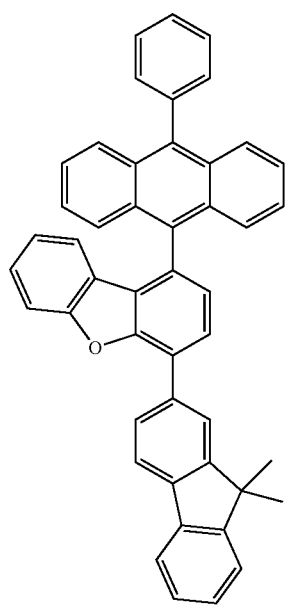
<Compound 43>

<Compound 44>
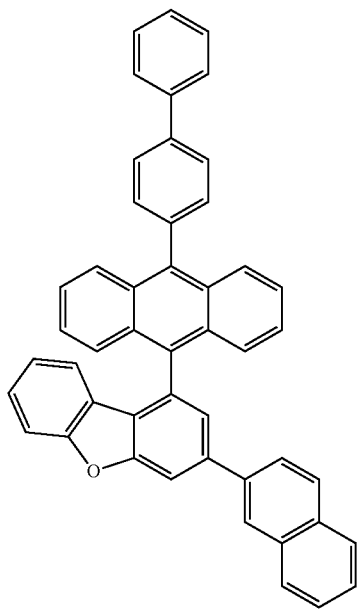
<Compound 46>
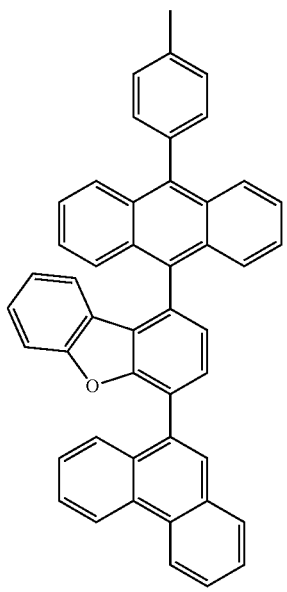
<Compound 61>
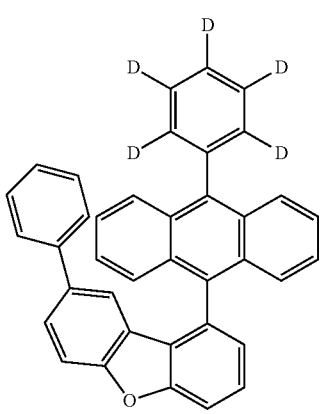
<Compound 45>
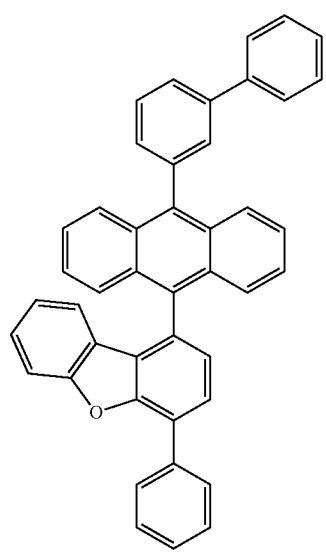
<Compound 62>
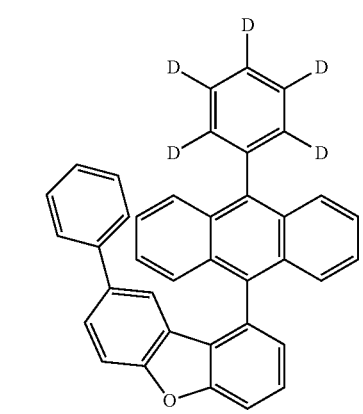

<Compound 63>
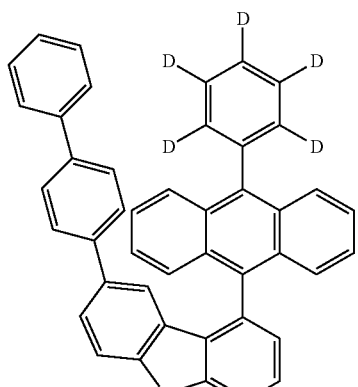
<Compound 66>
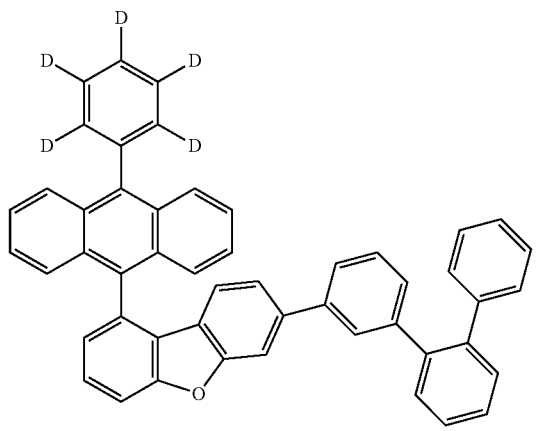
<Compound 64>
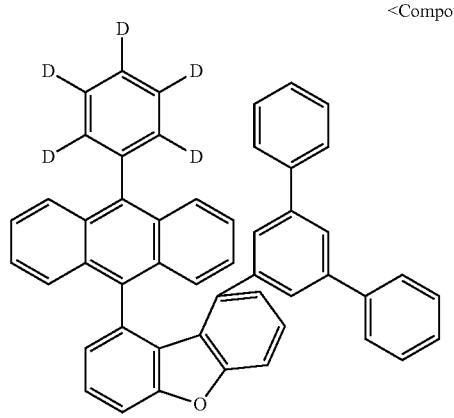
<Compound 67>
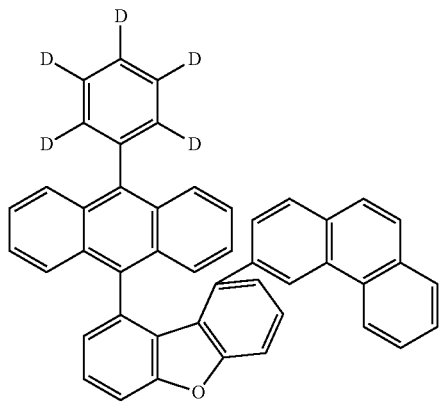
<Compound 65>
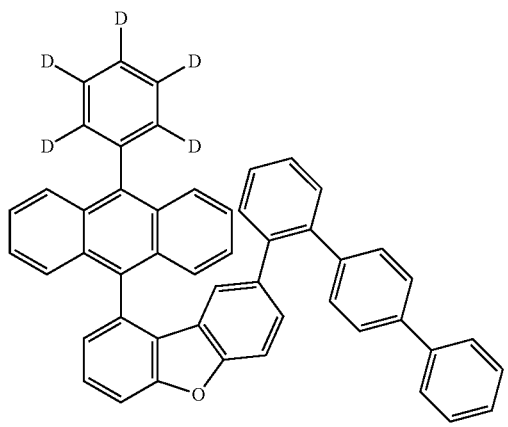
<Compound 68>
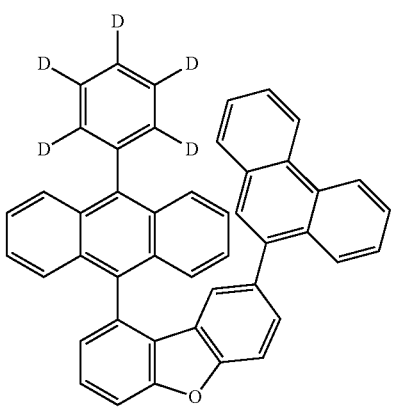

<Compound 69>
<Compound 73>
<Compound 74>
<Compound 75>
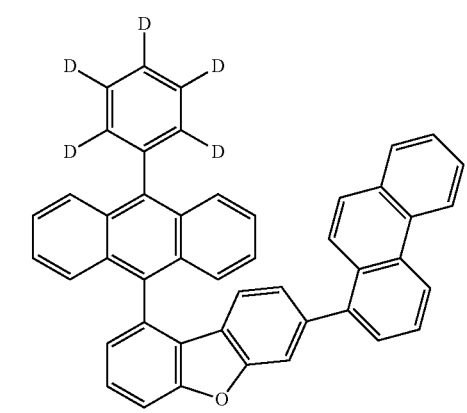
<Compound 79>
<Compound 80>
<Compound 81>
<Compound 103>
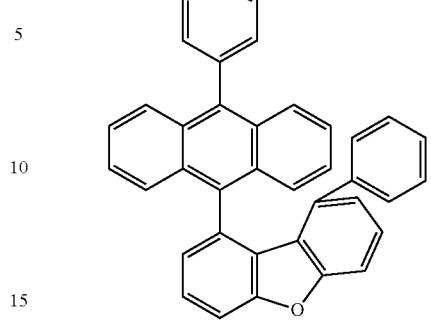
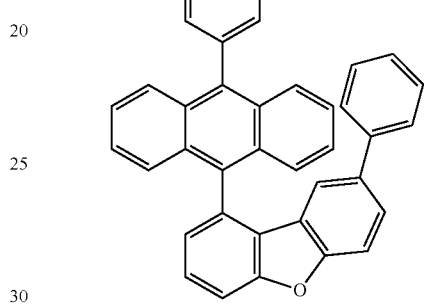
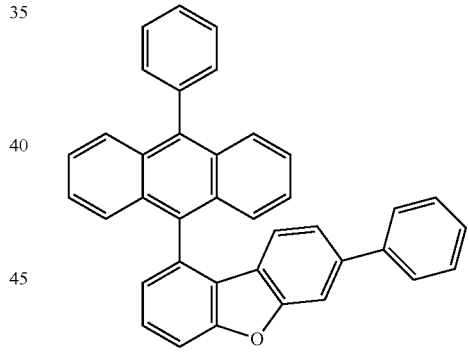
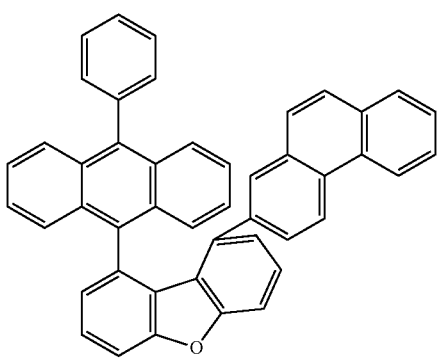

<Compound 104>
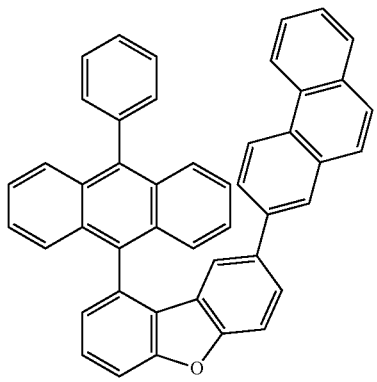
<Compound 105>
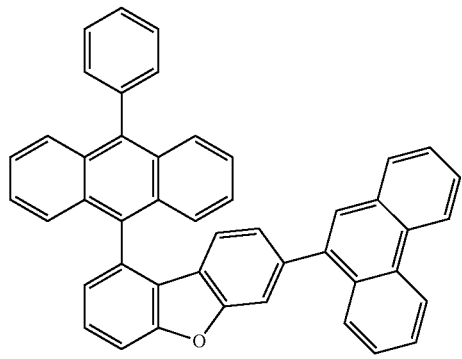
<Compound 106>
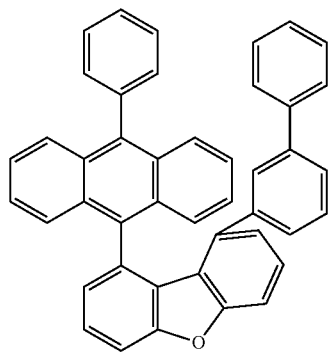
<Compound 107>
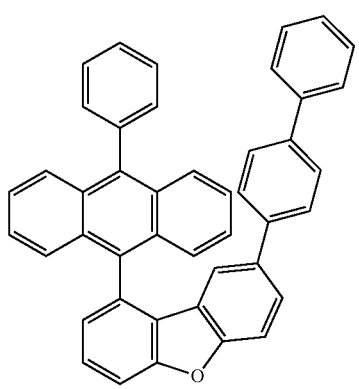
<Compound 108>
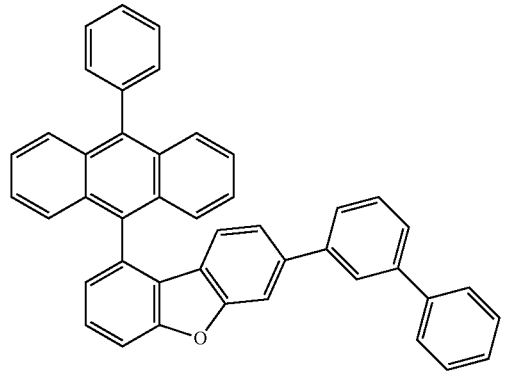
<Compound 109>
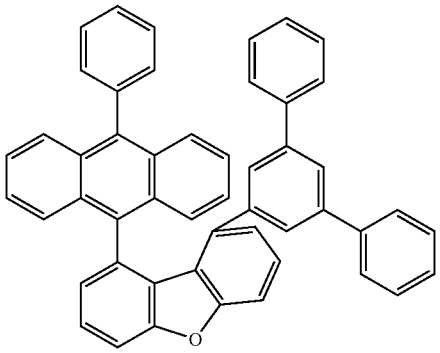
<Compound 110>
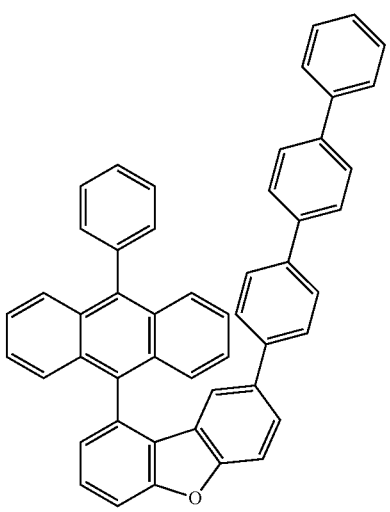

<Compound 111>
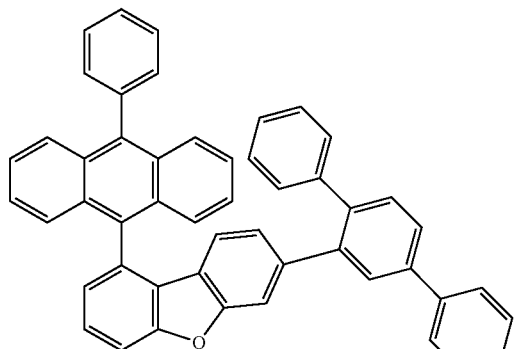
<Compound 112>
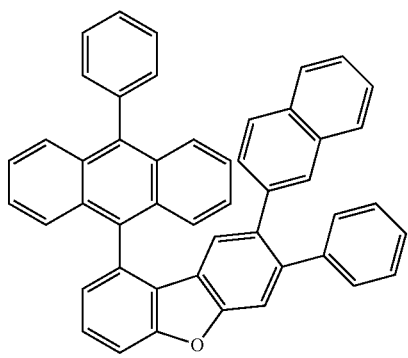
<Compound 113>
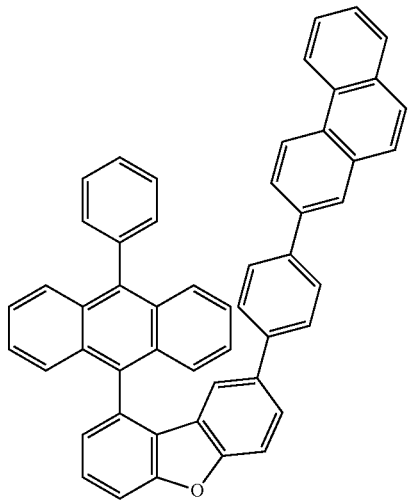
<Compound 114>
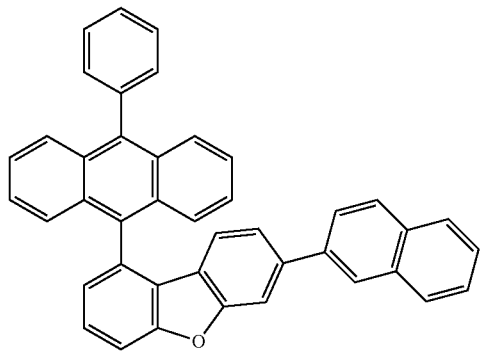
<Compound 139>
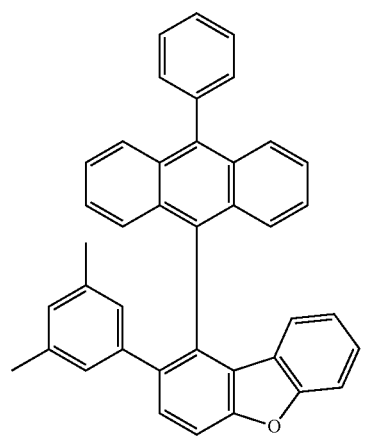
<Compound 140>
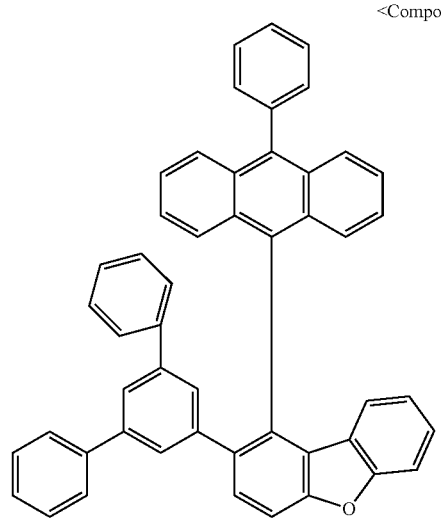
<Compound 141>
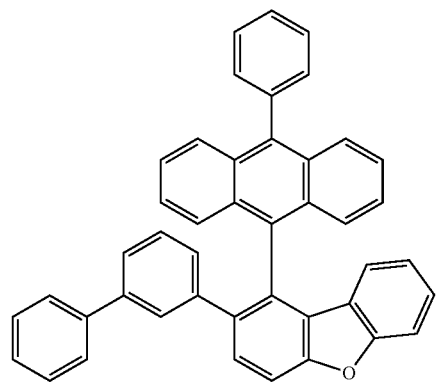

<Compound 145>
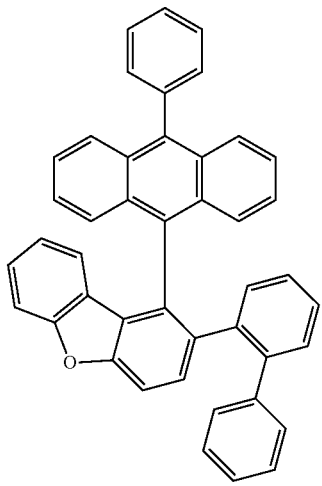
<Compound 146>
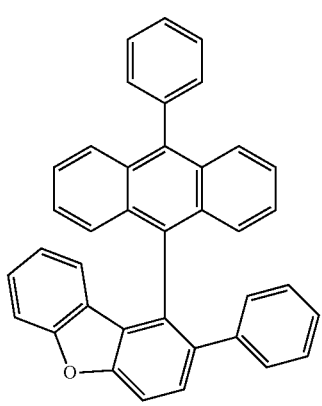
<Compound 147>
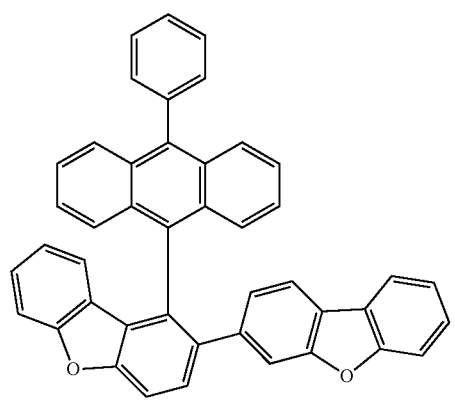
<Compound 150>
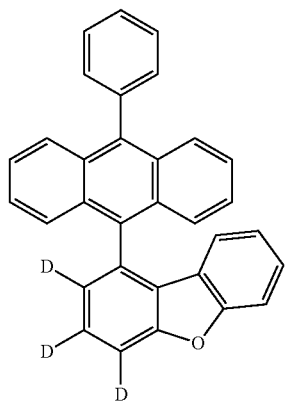
<Compound 151>
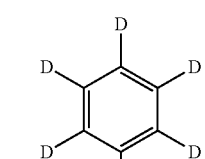
<Compound 152>
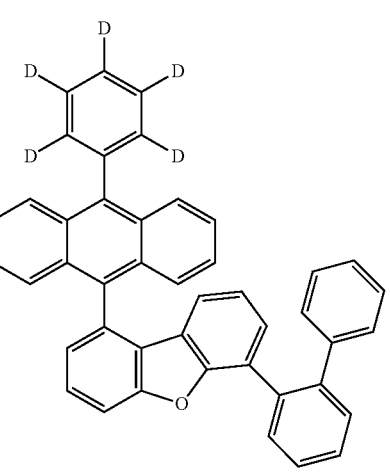

<Compound 153>
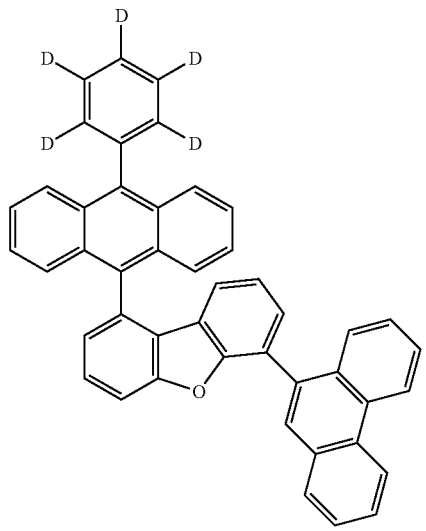
<Compound 154>
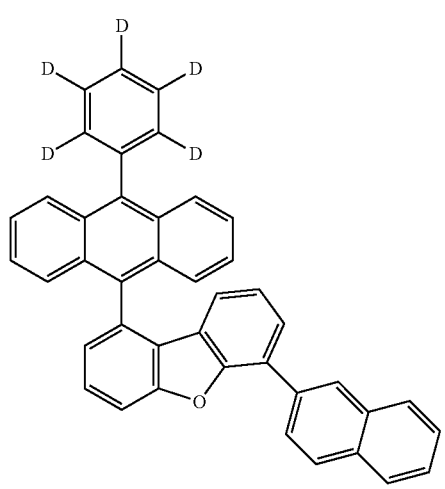
<Compound 155>
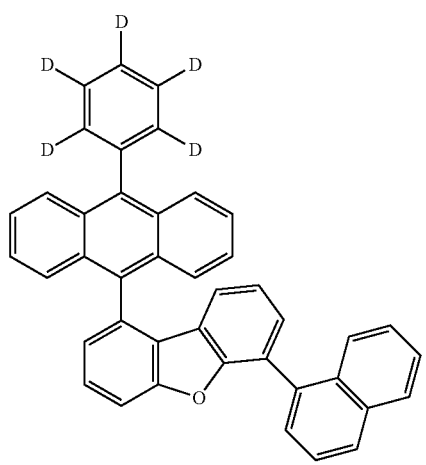
<Compound 156>
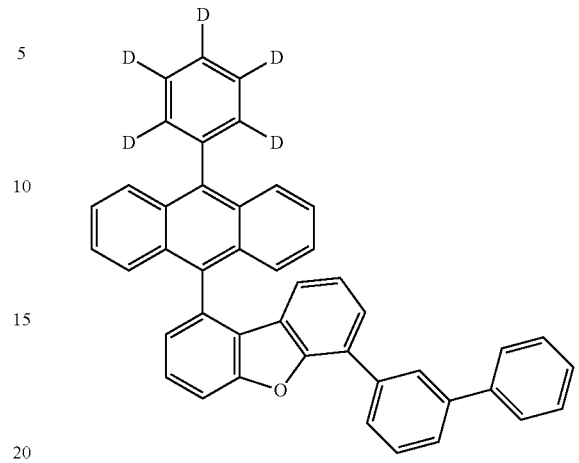
<Compound 157>
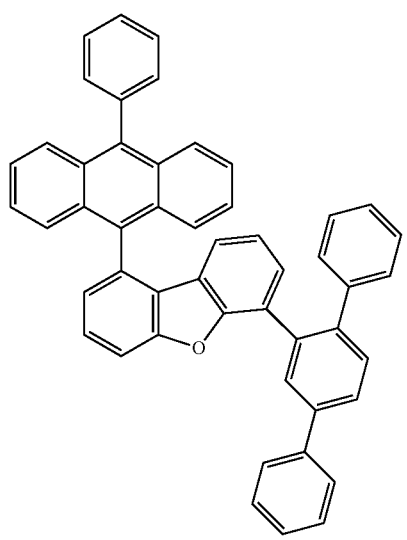
<Compound 158>
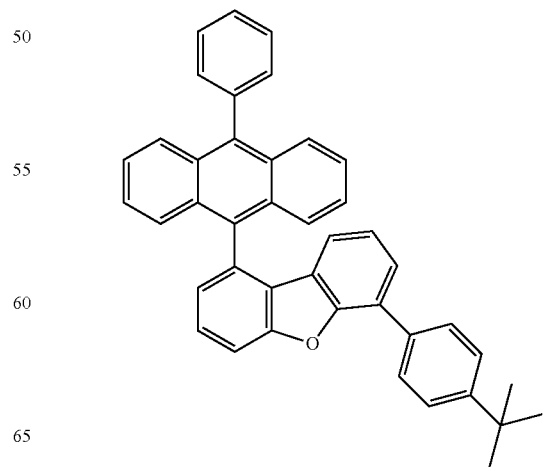

<Compound 161>
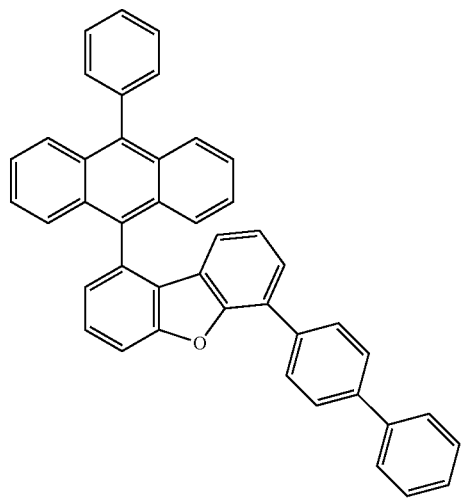
<Compound 162>
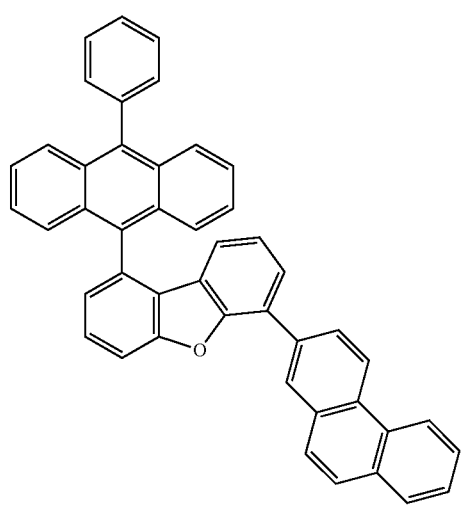
<Compound 163>
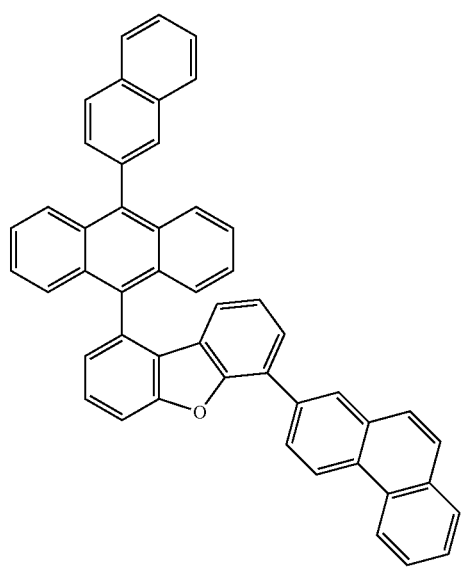
<Compound 164>
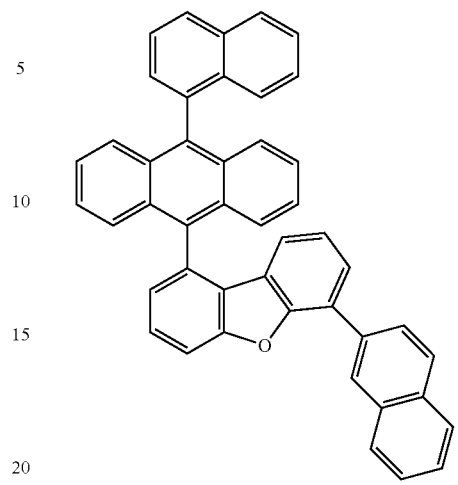
<Compound 165>
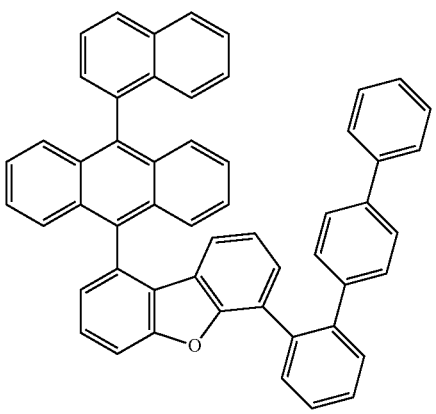
<Compound 166>
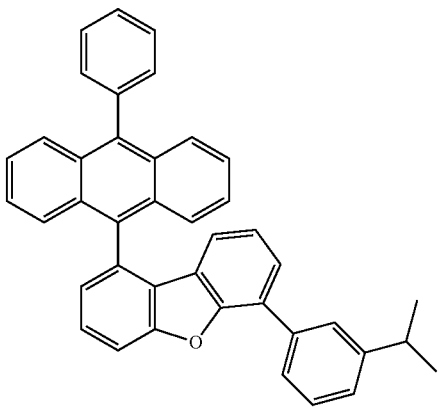

<Compound 167>
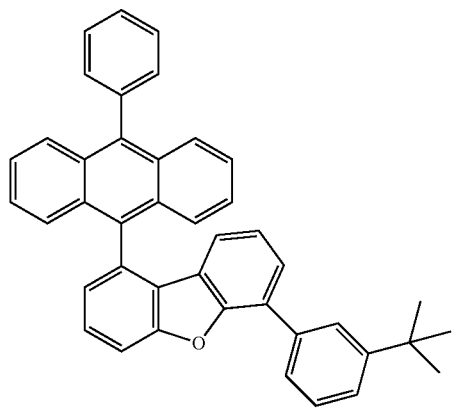
<Compound 168>
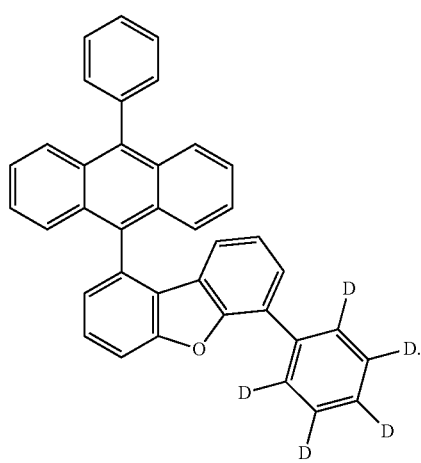
6. The organic light-emitting diode of claim 1, wherein the amine compound represented by Chemical Formula A is one selected from among the following Chemical Formulas:
<Chemical Formula 1>
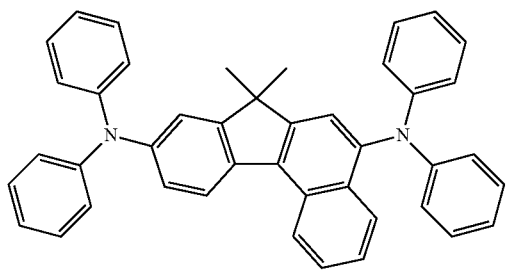
<Chemical Formula 2>
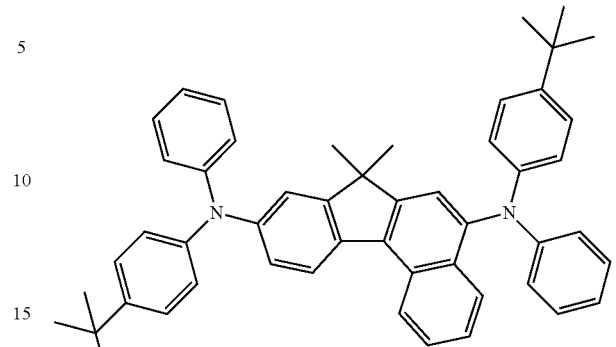
<Chemical Formula 4>
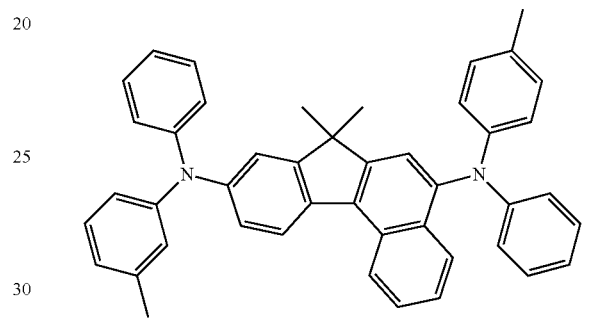
<Chemical Formula 5>
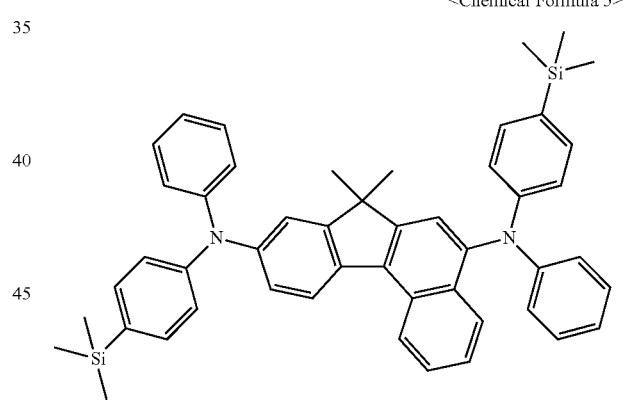
<Chemical Formula 7>
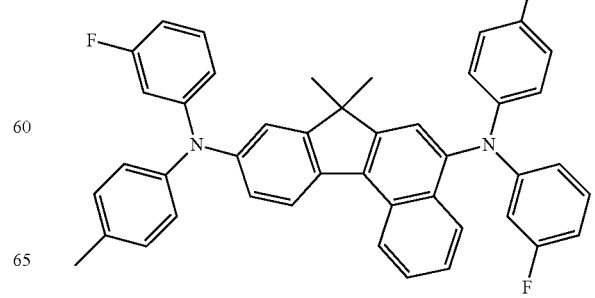

<Chemical Formula 8>
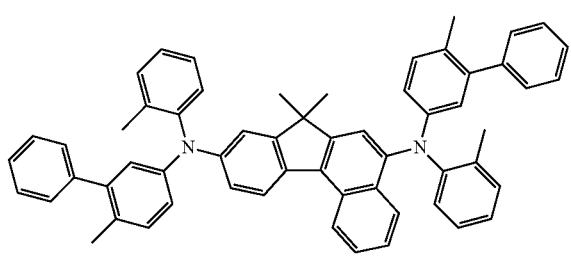
<Chemical Formula 9>
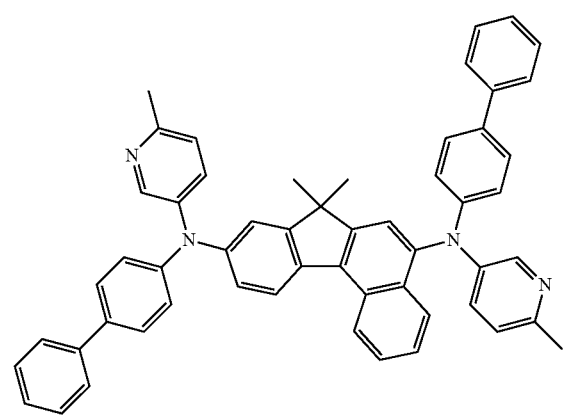
<Chemical Formula 10>
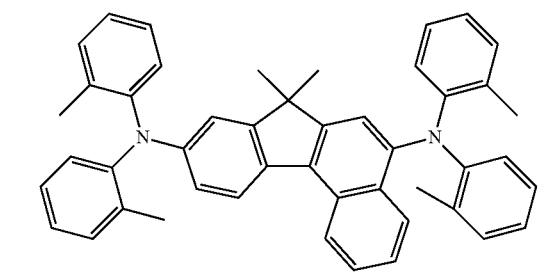
<Chemical Formula 11>
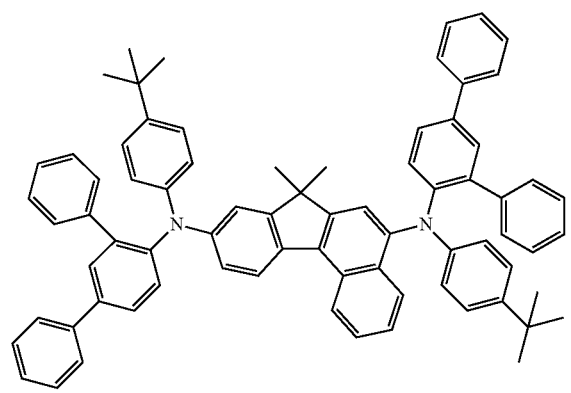
<Chemical Formula 12>
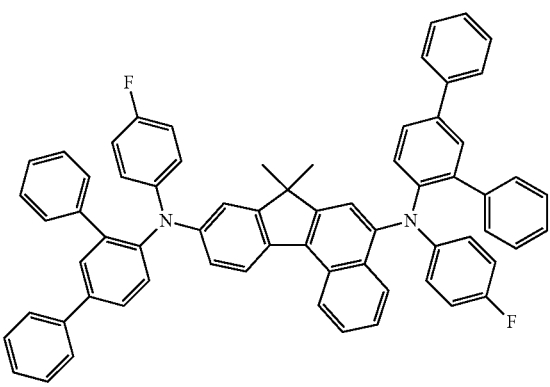
<Chemical Formula 13>
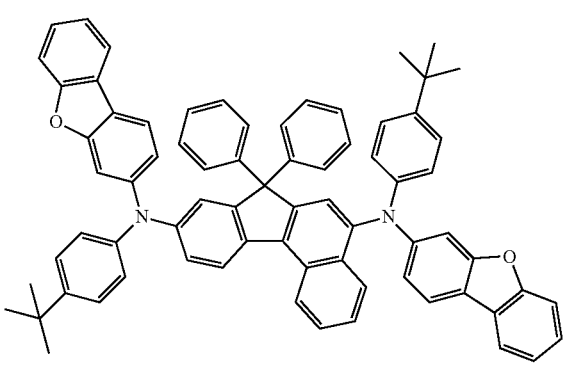
<Chemical Formula 14>
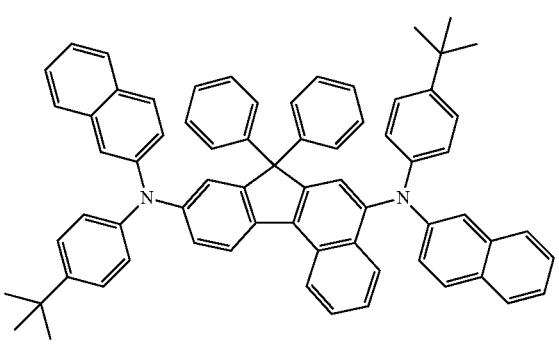
<Chemical Formula 15>
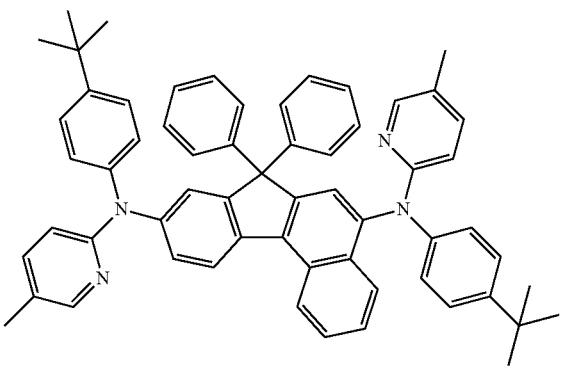

<Chemical Formula 16>
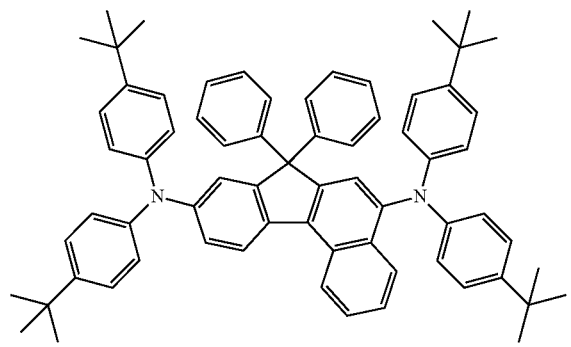
<Chemical Formula 17>
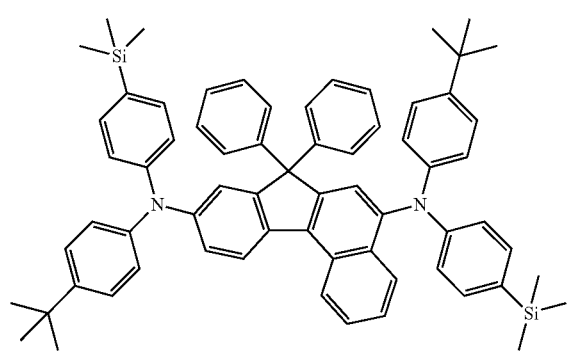
<Chemical Formula 18>
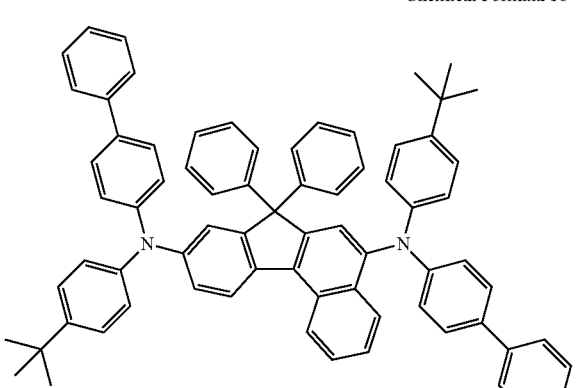
<Chemical Formula 19>
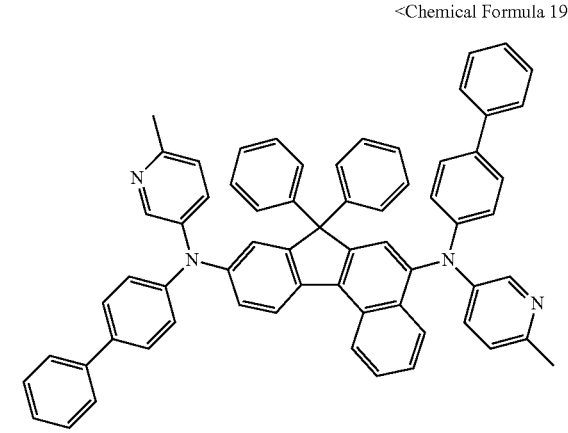
<Chemical Formula 20>
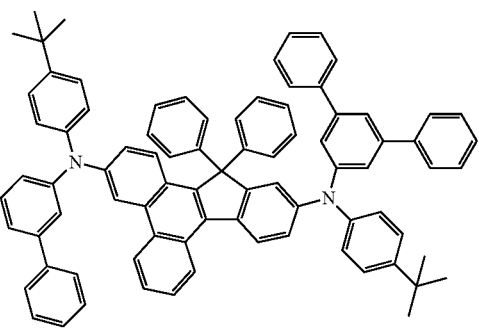
<Chemical Formula 21>
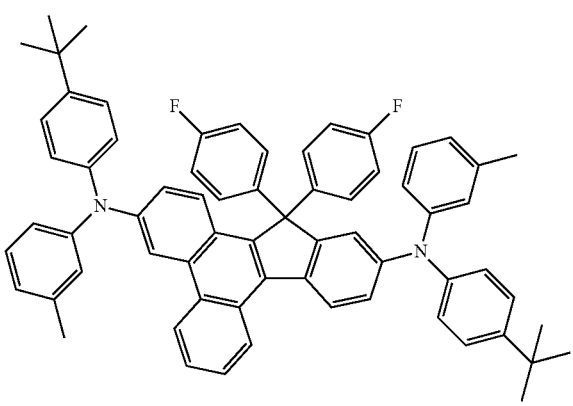
<Chemical Formula 22>
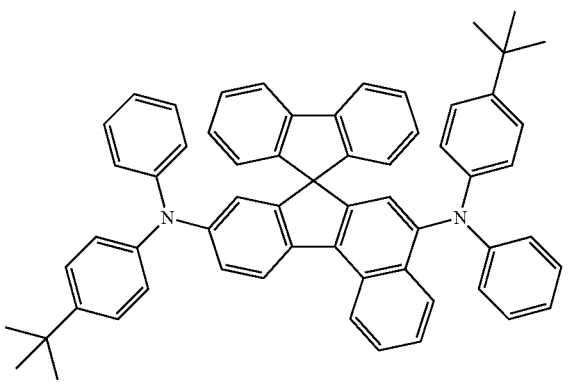
<Chemical Formula 23>
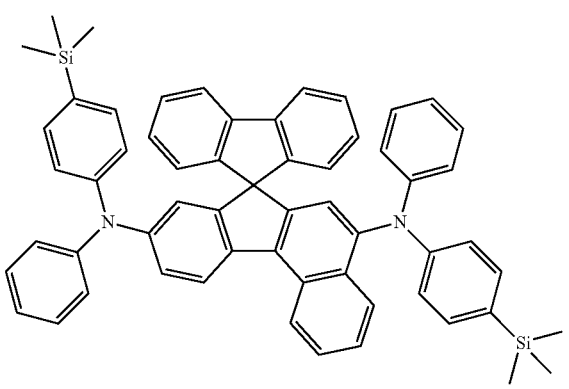

<Chemical Formula 24>
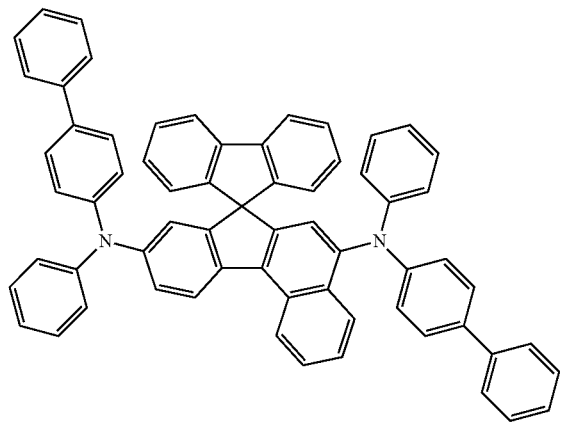
<Chemical Formula 25>
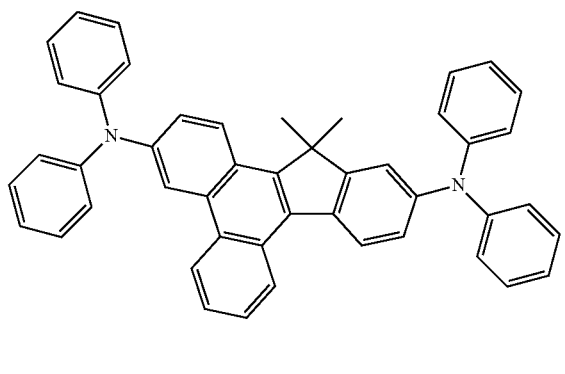
<Chemical Formula 26>
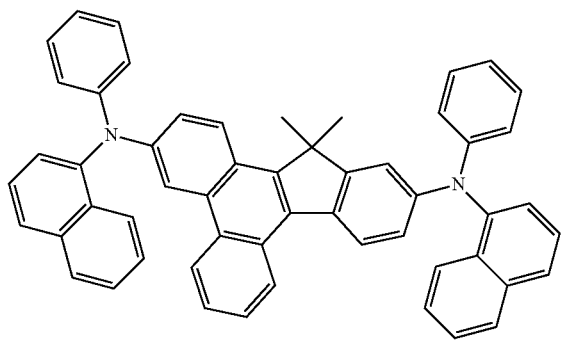
<Chemical Formula 27>
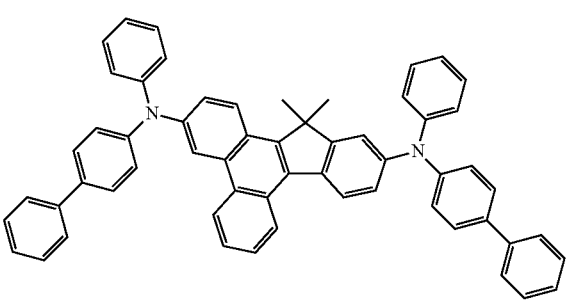
<Chemical Formula 29>
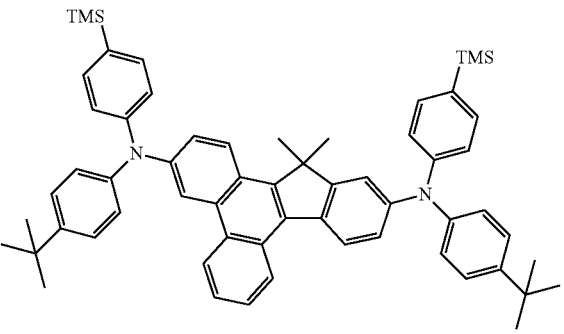
<Chemical Formula 30>
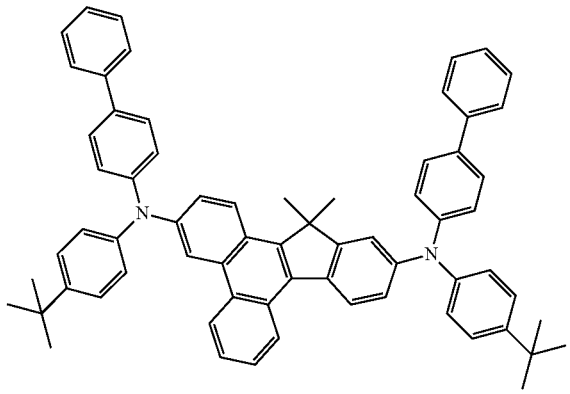
<Chemical Formula 31>
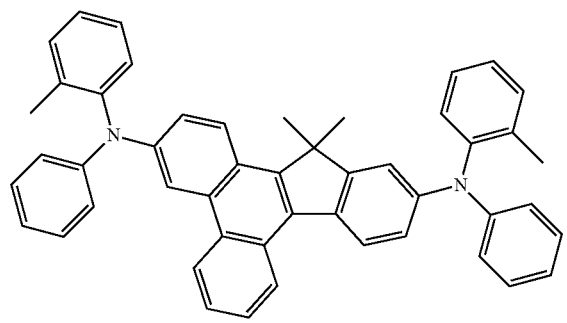
<Chemical Formula 32>
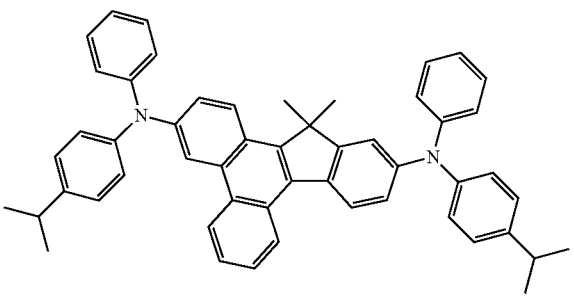

<Chemical Formula 33>
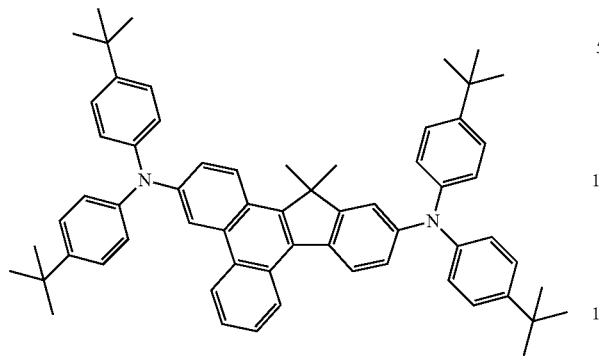
<Chemical Formula 34>
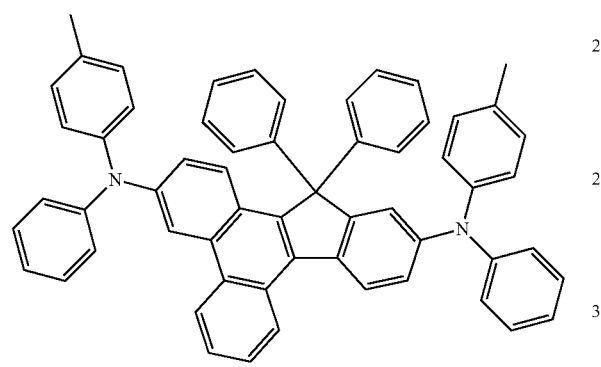
<Chemical Formula 35>
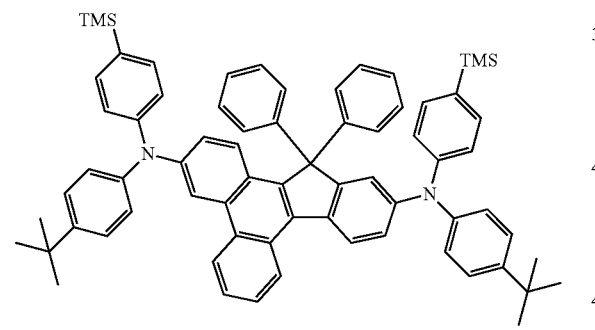
<Chemical Formula 36>
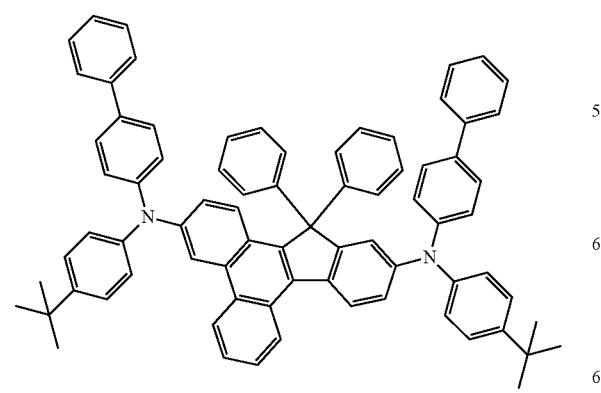
<Chemical Formula 37>
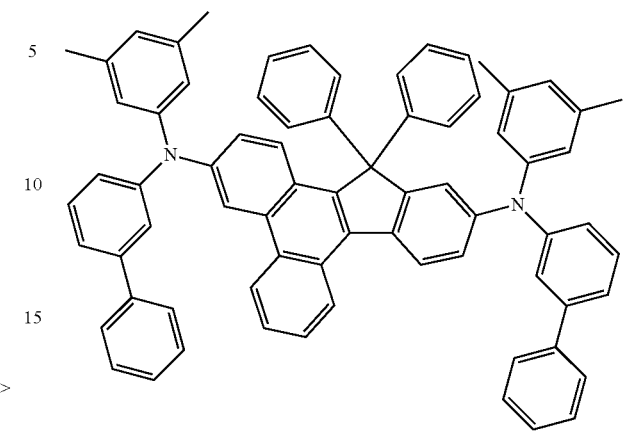
<Chemical Formula 38>
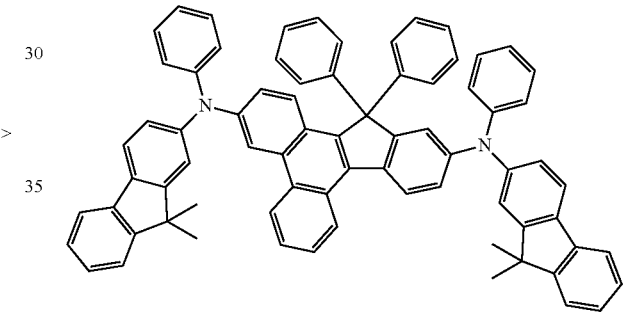
<Chemical Formula 39>
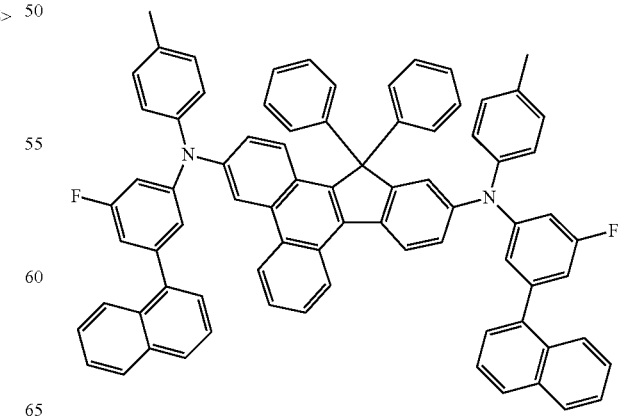

<Chemical Formula 40>

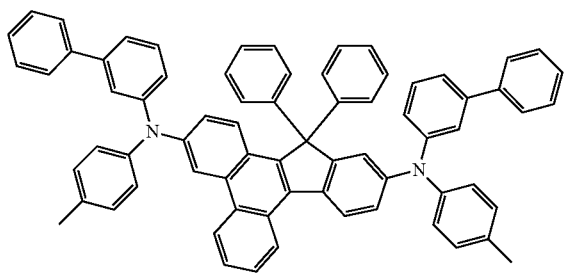

<Chemical Formula 42>

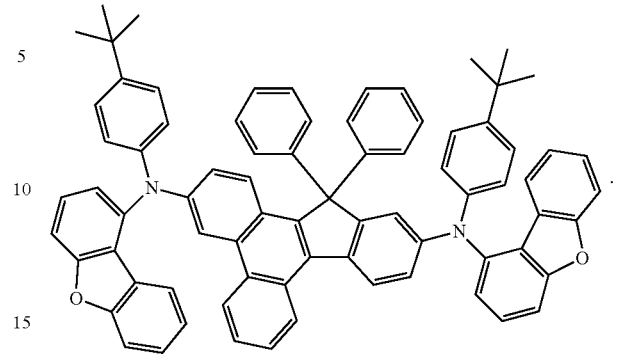

<Chemical Formula 41>

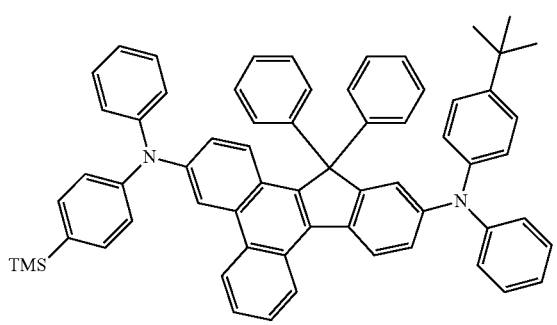

7. The organic light-emitting diode of claim 1, further comprising at least one of a hole injection layer, a hole transport layer, a functional layer capable of both hole injection and hole transport, an electron transport layer, and an electron injection layer in addition to the light-emitting layer.

8. The organic light-emitting diode of claim 7, wherein at least one selected from among the layers is deposited using a deposition process or a solution process.

9. The organic light-emitting diode of claim 1, wherein the organic light-emitting diode is used for a device selected from among a flat display device, a flexible display device, a monochrome or grayscale flat illumination device, and a monochrome or grayscale flexible illumination device.

* * * * *